(12) United States Patent
Berenson et al.

(10) Patent No.: US 11,207,385 B2
(45) Date of Patent: Dec. 28, 2021

(54) MELANOCORTINS AND METHODS OF USE THEREOF

(71) Applicant: Aequus Biopharma, Inc., Seattle, WA (US)

(72) Inventors: Ronald Berenson, Seattle, WA (US); Christopher H. Clegg, Seattle, WA (US)

(73) Assignee: Aequus Biopharma, Inc., Seattle, WA (US)

( * ) Notice: Subject to any disclaimer, the term of this patent is extended or adjusted under 35 U.S.C. 154(b) by 0 days.

(21) Appl. No.: 16/077,710

(22) PCT Filed: Dec. 14, 2016

(86) PCT No.: PCT/US2016/066711
§ 371 (c)(1),
(2) Date: Aug. 13, 2018

(87) PCT Pub. No.: WO2017/106378
PCT Pub. Date: Jun. 22, 2017

(65) Prior Publication Data
US 2019/0054150 A1 Feb. 21, 2019

Related U.S. Application Data

(60) Provisional application No. 62/422,024, filed on Nov. 14, 2016, provisional application No. 62/364,255, filed on Jul. 19, 2016, provisional application No. 62/318,717, filed on Apr. 5, 2016, provisional application No. 62/267,282, filed on Dec. 14, 2015.

(51) Int. Cl.
| | | |
|---|---|---|
| *A61K 38/33* | (2006.01) | |
| *A61K 47/55* | (2017.01) | |
| *A61K 47/65* | (2017.01) | |
| *A61K 47/64* | (2017.01) | |
| *A61P 19/02* | (2006.01) | |
| *A61K 9/00* | (2006.01) | |

(52) U.S. Cl.
CPC ............. *A61K 38/33* (2013.01); *A61K 9/006* (2013.01); *A61K 9/0019* (2013.01); *A61K 9/0024* (2013.01); *A61K 9/0043* (2013.01); *A61K 9/0073* (2013.01); *A61K 47/55* (2017.08); *A61K 47/64* (2017.08); *A61K 47/65* (2017.08); *A61P 19/02* (2018.01); *C07K 2319/00* (2013.01); *C07K 2319/01* (2013.01)

(58) Field of Classification Search
None
See application file for complete search history.

(56) References Cited

U.S. PATENT DOCUMENTS

2013/0259875 A1* 10/2013 Somera-Molina ...... A61P 21/00
424/173.1

FOREIGN PATENT DOCUMENTS

WO 2015/018827 2/2015

OTHER PUBLICATIONS

Anonymous. UniProtKB-P01189 (Coli_Human). (Year: 1991).*
Wardlaw S "Hypothalamic proopiomelanocortin processing and the regulation of energy balance" Eur. J. Pharmacol. 660:213-219. ( Year: 2011).*
Catania et al., "Targeting Melanocortin Receptors as a Novel Strategy to Control Inflammation," *Pharmacol. Rev.* 56(1):1-29, 2004.
Catania et al., "The Melanocortin System in Control of Inflammation," *TheScientificWorldJournal* 10:1840-1853, 2010.
Daoussis et al., "ACTH as a treatment for acute crystal-induced arthritis: update on clinical evidence and mechanisms of action," *Semin. Arthritis. Rheum.* 43(5):648-653, 2014.
Getting, "Targeting melanocortin receptors as potential novel therapeutics," *Pharmacol. Ther.* 111(1):1-15, 2006.
Hadley et al., "Melanocortin peptide therapeutics: historical milestones, clinical studies and commercialization," *Peptides* 27(4):921-930, 2006.
Montero-Melendez et al., "Role of melanocortin receptors in the regulation of gouty inflammation," *Curr. Rheumatol. Rep.* 13(2):138-145, 2011.
Montero-Melendez, "ACTH: The forgotten therapy," *Semin. Immunol.* 27(3):216-226, 2015.
Taylor et al., "Corticotropin for Acute Management of Gout," *The Annals Pharmacotherapy* 35:365-368, 2001.
Berenson et al., "A Melanocortin Fusion Peptide (AQB-565) Optimized for Melanocortin Receptor Engagement Significantly Reduces Inflammation in an In Vivo model of Acute Gout," Abstract No. 2266, *Arthritis Rheumatol.* 68(Suppl. 10), 2016, (2 pages).
International Search Report and Written Opinion, dated Mar. 10, 2017, for International Application No. PCT/US2016/066711, 11 pages.
Yang et al., "Novel Binding Motif of ACTH Analogues at the Melanocortin Receptors," *Biochemistry* 48(41):9775-9784, 2009.

* cited by examiner

*Primary Examiner* — Sudhakar Katakam
*Assistant Examiner* — Zachary J Miknis
(74) *Attorney, Agent, or Firm* — Seed Intellectual Property Law Group LLP

(57) ABSTRACT

In some aspects, the present disclosure provides compositions and methods for treating disease, e.g., inflammatory disease. Compositions herein comprise one or more polypeptide fragments of proopiomelanocortin or variants thereof. The one of more polypeptide fragments of proopiomelanocortin or variants thereof may be linked by a linker, e.g., a peptide linker, to form a fusion polypeptide.

22 Claims, 15 Drawing Sheets

Specification includes a Sequence Listing.

MELANOCORTINS AND METHODS OF USE THEREOF

CROSS-REFERENCE

This application claims the benefit of U.S. Provisional Patent Application No. 62/267,282, filed Dec. 14, 2015, U.S. Provisional Patent Application No. 62/318,717, filed Apr. 5, 2016, U.S. Provisional Patent Application No. 62/364,255, filed Jul. 19, 2016, and U.S. Provisional Patent Application No. 62/422,024, filed Nov. 14, 2016, the entire disclosures of which are incorporated by reference herein.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is SEQUENCE_LISTING_120262_401USPC. The text file is 51 KB, was created on Apr. 29, 2021, and is being submitted electronically via EFS-Web.

BACKGROUND

Melanocortins refer to a family of peptides derived from the precursor polypeptide proopiomelanocortin (POMC). Melanocortins include adrenocorticotropic hormone (ACTH) and the melanocyte-stimulating hormones (MSH): α-MSH, β-MSH, and γ-MSH. Proopiomelanocortin (POMC) is the precursor to a number of important peptides in addition to melanocortins, such as the opioid neuropeptide β-endorphin and β-lipotropin.

Melanocortins bind to melanocortin receptors (MCRs) to generate biological effects. There are 5 MCRs, which bind with varying affinity to individual melanocortins. MCRs are G protein-coupled receptors that generate biological effects through the production of cAMP. Each receptor is associated with different biological processes although many have anti-inflammatory effects.

SUMMARY

Described herein are compositions comprising a first polypeptide comprising a fragment of a proopiomelanocortin or a variant thereof; and a second polypeptide comprising a fragment of a proopiomelanocortin or a variant thereof, wherein at least one of the first polypeptide and the second polypeptide binds to a melanocortin receptor. In some instances, the compositions comprise one or more additional polypeptides, wherein each polypeptide comprises a fragment of a proopiomelanocortin or a variant thereof; and wherein at least one of the polypeptides binds a melanocortin receptor.

In some instances, the first polypeptide and the second polypeptide of the compositions described herein independently have a length of at least 3 amino acids and no more than 30 amino acids, at least 3 amino acids and no more than 40 amino acids, at least 3 amino acids and no more than 50 amino acids, at least 5 amino acids and no more than 30 amino acids, at least 5 amino acids and no more than 40 amino acids, at least 5 amino acids and no more than 50 amino acids, at least 10 amino acids and no more than 30 amino acids, at least 10 amino acids and no more than 40 amino acids, or at least 10 amino acids and no more than 50 amino acids.

In some instances, the first polypeptide and the second polypeptide are covalently linked as fusion polypeptides. In some instances, the compositions described herein further comprise a linker covalently linking the first polypeptide and the second polypeptide.

In some cases, the fusion polypeptides are an acyclic polypeptide. In some aspects, the fusion polypeptides are linear polypeptides. In some aspects, the first polypeptide of the compositions described herein is α-MSH, and the second polypeptide is not β-MSH.

In some respects, the fusion polypeptides have a length of at least 5 amino acids and no more than 100 amino acids, at least 5 amino acids and no more than 75 amino acids, at least 10 amino acids and no more than 75 amino acids, at least 20 amino acids and no more than 75 amino acids, at least 20 amino acids and no more than 60 amino acids, or at least 30 amino acids and no more than 60 amino acids.

In some instances, the compositions comprise a plurality of copies of the first polypeptide in the fusion polypeptide. In some instances, the compositions also comprise a plurality of copies of the second polypeptide in the fusion polypeptide.

In some aspects, each polypeptide of the compositions described herein is covalently linked to a separate polypeptide through a linker.

In some aspects, the stoichiometric molar ratio between the first polypeptide and the second polypeptide in the compositions is selected from 0.1:1, 0.25:1, 0.33:1, 0.5:1, 1:1, 2:1, 3:1, 4:1, 5:1, or 10:1.

In some aspects, the first polypeptide of the compositions comprises a melanocyte stimulating hormone (MSH), ACTH, γ-LPH, or β-endorphin. In some aspects, the first polypeptide comprises an MSH selected from α-MSH, β-MSH, or γ-MSH. In some aspects, the first polypeptide of the compositions described herein is α-MSH. In some aspects, the first polypeptide is at least 75%, 80%, 85%, 90%, or 95% identical to SEQ ID NO. 11 (α-MSH).

In various aspects, the first polypeptide comprises an MSH variant comprising at least one of an amino acid mutation, an amino acid analogue, a non-natural amino acid, an amino acid isomer, and truncation compared to a wild-type sequence. In some aspects, the MSH variants are NDP-α-MSH. In some aspects, the MSH variants are an acetylated form (e.g., Ac-NDP-α-MSH) or a non-acetylated form (e.g., NDP-α-MSH).

In some aspects, the first polypeptides are at least 75%, 80%, 85%, 90%, or 95% identical to SEQ ID NO. 12 (NDP-α-MSH) or SEQ ID NO. 72 (Ac-NDP-α-MSH). In some aspects, the first polypeptide of compositions described herein is γ-MSH. In some aspects, the first polypeptide of compositions described herein is at least 75%, 80%, 85%, 90%, or 95% identical to SEQ ID NO. 20 (γ-MSH). In some aspects, the MSH variant is NDP-γ-MSH. In some aspects, the first polypeptide of compositions described herein is at least 75%, 80%, 85%, 90%, or 95% identical to SEQ ID NO. 18 (NDP-γ-MSH). In some aspects, the first polypeptide of compositions described herein comprises adrenocorticotropic hormone (ACTH) or a fragment thereof. In some aspects, the first polypeptide of compositions described herein is at least 75%, 80%, 85%, 90%, or 95% identical to SEQ ID NO. 19 (ACTH$_{1-39}$) or a fragment thereof. In some aspects, the first polypeptide of compositions described herein is at least 75%, 80%, 85%, 90%, or 95% identical to SEQ ID NO. 10 (ACTH$_{1-24}$) or a fragment thereof. In some aspects, the first polypeptide of compositions described herein is SEQ ID NO. 31.

In various aspects, the second polypeptide comprises a melanocyte stimulating hormone (MSH), ACTH, γ-LPH, or β-endorphin. In some aspects, the second polypeptide comprises a second MSH selected from α-MSH, β-MSH, or γ-MSH. In some aspects, the second polypeptide comprises an MSH variant comprising at least one of an amino acid mutation, an amino acid analogue, a non-natural amino acid, an amino acid isomer, and truncation compared to a wild-type sequence. In some aspects, the second polypeptide is at least 75%, 80%, 85%, 90%, or 95% identical to SEQ ID NO. 12 (NDP-α-MSH). In some aspects, the second polypeptide comprises adrenocorticotropic hormone (ACTH) or a fragment thereof. In some aspects, the second polypeptide is at least 75%, 80%, 85%, 90%, or 95% identical to SEQ ID NO. 19 ($ACTH_{1-39}$) or a fragment thereof. In some aspects, the second polypeptide is at least 75%, 80%, 85%, 90%, or 95% identical to SEQ ID NO. 10 ($ACTH_{1-24}$), SEQ ID NO. 47 (NDP-$ACTH_{1-24}$) or a fragment thereof. In some aspects, the second polypeptide is an ACTH variant comprising at least one of an amino acid mutation, an amino acid analogue, a non-natural amino acid, an amino acid isomer, and truncation compared to wild-type ACTH. In some aspects, the second polypeptide of compositions described herein can be SEQ ID NO. 31. In some aspects, the MSH is acetylated. In some cases, the MSH is terminally acetylated.

In various aspects, each polypeptide of a plurality of polypeptides comprises a melanocyte stimulating hormone (MSH), ACTH, γ-LPH, or β-endorphin. In some aspects, each polypeptide of a plurality of polypeptides comprises a second MSH selected from α-MSH, β-MSH, or γ-MSH. In some aspects, each polypeptide of a plurality of polypeptides comprises an MSH variant or ACTH variant comprising at least one of an amino acid mutation, an amino acid analogue, a non-natural amino acid, an amino acid isomer, and truncation compared to a wild-type sequence.

In certain aspects, the first and second polypeptide are two identical or different melanocortin or variants thereof. In certain aspects, at least one or both of the first and second polypeptide do not comprise ACTH. In certain aspects, at least one or both of the first and second polypeptide are not ACTH.

In various aspects, the fusion polypeptide has an arrangement of formula (I):

first polypeptide—linker—second polypeptide     Formula (I).

In other aspects, the fusion polypeptide has an arrangement of formula (II):

second polypeptide—linker—first polypeptide     Formula (II).

In some aspects, the linkers described here are selected from KR, RRKR (SEQ ID NO. 73), KKRR (SEQ ID NO. 74), RRNSSSGSSGAGQKR (SEQ ID NO. 75), ERLKRAVGS (SEQ ID NO. 76), SRSRRSAGS (SEQ ID NO. 77), ERSKRAVGS (SEQ ID NO: 78), ERLKRAAGS (SEQ ID NO. 79), GGGGSGGGGS (SEQ ID NO. 80), GGGS (SEQ ID NO. 92), GGGGSGG (SEQ ID NO. 93), PLGLWA (SEQ ID NO. 81), PQALVA (SEQ ID NO. 82), PANLVG (SEQ ID NO: 83), PAELIG (SEQ ID NO. 84), PANLVA (SEQ ID NO. 85), PAGLVG (SEQ ID NO. 86), or PAGLVA (SEQ ID NO. 87).

In some aspects, the linkers comprise a cleavage site. In various aspects, the cleavage site is cleavable by a protease. In various aspects, the protease is a metalloproteinase, a proconvertase, or a cathepsin. In various aspects, the protease is a metalloproteinase or a proconvertase. In various aspects, the protease is a metalloproteinase. In various aspects, the protease is an endoprotease. In various aspects, the endoprotease is furin. In various aspects, the linker comprises a sequence native to humans. In other aspects, the linker comprises a sequence non-native to humans. In various aspects, the linker is non-immunogenic to humans. In some aspects the compositions described herein further comprise a plurality of linkers within the fusion polypeptide that are the same or different from one another.

In various aspects, the compositions described herein further comprise a half-life extending moiety covalently linked to the fusion polypeptide. In some aspects, the half-life extending moiety is selected from a glycopolymer, albumin, an Fc portion of immunoglobulin, a glycopeptide, a glycopolymer, polyethylene glycol, hetastarch, half-life extending polypeptides, or a combination thereof. In some aspects, the half-life extending moiety is a glycopolymer.

In some aspects, the compositions described herein further comprise a targeting moiety covalently linked to the fusion polypeptide.

In some aspects, the first polypeptides described herein are at least 75%, 80%, 85%, 90%, or 95% identical to a sequence selected from SEQ ID NO. 9, SEQ ID NO. 10, SEQ ID NO. 11, SEQ ID NO. 12, SEQ ID NO. 16, SEQ ID NO. 17, SEQ ID NO. 18, SEQ ID NO. 19, SEQ ID NO. 20, SEQ ID NO. 30, SEQ ID NO. 31, SEQ ID NO. 35, SEQ ID NO. 36 or a fragment thereof.

In some aspects, the second polypeptides described herein are at least 75%, 80%, 85%, 90%, or 95% identical to a sequence selected from SEQ ID NO. 9, SEQ ID NO. 10, SEQ ID NO. 11, SEQ ID NO. 12, SEQ ID NO. 16, SEQ ID NO. 17, SEQ ID NO. 18, SEQ ID NO. 19, SEQ ID NO. 20, SEQ ID NO. 30, SEQ ID NO. 31, or SEQ ID NO. 35, SEQ ID NO. 36 or a fragment thereof.

In some aspects, the compositions described herein comprise a fusion polypeptide that is at least 75%, 80%, 85%, 90%, or 95% identical to SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 13, SEQ ID NO. 14, SEQ ID NO. 15, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 32, SEQ ID NO. 34, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 46, SEQ ID NO. 51, SEQ ID NO. 52, SEQ ID NO. 53, SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72 or a fragment thereof.

In some aspects, the compositions described herein are less steroidogenic than ACTH, wherein a steroidogenic response includes increased production of progestogens, corticosteroids, mineralocorticoids, or estrogens.

Described herein are methods of treating subjects in need thereof, the methods comprising administering to the subject a composition comprising: a first polypeptide comprising a fragment of a proopiomelanocortin or a variant thereof; and a second polypeptide comprising a fragment of a proopiomelanocortin or a variant thereof, wherein at least one of the first polypeptide and the second polypeptide binds to a melanocortin receptor. In various aspects, the treating comprises reducing inflammation and the administering reduces inflammation in the subject. In some aspects, the composition is less steroidogenic than ACTH. In various aspects, the treating is prophylactic.

Described herein are methods of reducing inflammation in subjects, the methods comprising administering to the subject a composition comprising: a first polypeptide comprising a fragment of a proopiomelanocortin or a variant thereof; and a second polypeptide comprising a fragment of a proopiomelanocortin or a variant thereof, thereby reducing inflammation in the subjects.

Described herein are methods of reducing inflammation in subjects, the method comprising administering a single therapeutically effective dose of a composition to the subjects, the composition comprising: a first polypeptide comprising a fragment of a proopiomelanocortin or a variant thereof; and a second polypeptide comprising a fragment of a proopiomelanocortin or a variant thereof that provides a maximum plasma cortisol concentration following administration that is less than 6 times the basal level concentration, less than 5.5 times the basal level concentration, less than 5 times the basal level concentration, less than 4.5 times the basal level concentration, less than 4 times the basal level concentration, less than 3.5 times the basal level concentration, less than 3 times the basal level concentration, less than 2 times the basal level concentration, or less than 1.5 times the basal level concentration or any intermediate numbers or ranges derived therefrom.

In various aspects, the methods described herein further comprise administering a single dose to a human subject of at least 0.1 nanomoles per kilogram (kg) and not more than 300 nanomoles per kg; at least 0.3 nanomoles per kilogram and not more than 100 nanomoles per kg; at least 0.5 nanomoles per kilogram and not more than 50 nanomoles per kg; at least 1 nanomole per kilogram and not more than 30 nanomoles per kg; at least 2 nanomoles per kilogram and not more than 20 nanomoles per kg of the composition; or any ranges or values derived therefrom. In various aspects, the methods described herein reduce inflammation associated with an inflammatory disease or condition, or a disease or condition of the immune system. The inflammation can be acute, chronic, or a combination thereof.

Described herein are methods of reducing inflammation in subjects, the method comprising administering a single dose of at least 0.1 nanomoles per kilogram and not more than 300 nanomoles per kilogram, the composition comprising: a first polypeptide comprising a fragment of a proopiomelanocortin or a variant thereof; and a second polypeptide comprising a fragment of a proopiomelanocortin or a variant thereof.

In some aspects, the methods of reducing inflammation in human subjects comprise administering a single dose of at least 0.3 nanomoles per kilogram (kg) and not more than 100 nanomoles per kg; at least 0.5 nanomoles per kilogram and not more than 50 nanomoles per kg; at least 1 nanomole per kilogram and not more than 30 nanomoles per kg; at least 2 nanomoles per kilogram and not more than 20 nanomoles per kg of the composition; or any ranges or values derived therefrom.

In some aspects, the treating comprises modulating the receptor activity of MC2R. In other aspects, the treating comprises modulating the receptor activity of MC1R, MC3R, MC4R, MC5R, or a combination thereof. In some aspects, the modulating comprises agonizing the receptor. In some aspects, the treating comprises decreasing production of a pro-inflammatory molecule, increasing production of an anti-inflammatory molecule, or a combination thereof. In some aspects, the treating can comprise modulating the inflammasome. In some aspects, the treating comprises modulating cytokine production. In some aspects, the treating is prophylactic. In some aspects, the cytokines are selected from: tumor necrosis factor-α (TNF-α), transforming growth factor β (TGF-β), Interleukin-1β (IL-1β), Interleukin-2 (IL-2), Interleukin-4 (IL-4), Interleukin-6 (IL-6), Interleukin-8 (IL-8), interferon-γ (IFN-γ), Interleukin-10 (IL-10), Interleukin-12 (IL-12), Interleukin-17 (IL-17), granulocyte-macrophage colony-stimulating factor (GM-CSF), keratinocyte chemoattractant (KC), latency associated peptide (LAP), monocyte chemoattractant protein-1 (MCP-1), macrophage inflammatory protein (MIP-1α or MIP-1β), or a combination thereof. In some aspects, the treating according to the present disclosure comprises modulating chemokine production. In some aspects, the treating according to the present disclosure comprises decreasing neutrophil count at a site of inflammation, inhibiting neutrophil migration and their phagocytosis, or a combination thereof. In some aspects, the first polypeptide and the second polypeptide are covalently linked as a fusion polypeptide. In some aspects, the fusion polypeptide further comprises a linker covalently linking the first polypeptide and the second polypeptide. In some aspects, the treating is associated with a disease or condition of the immune system. In some aspects, the treating is associated with a bone formation disease or condition. In some aspects, the treating comprises neuroprotection.

In some aspects, the inflammation is associated with an autoimmune condition. In some aspects, the inflammation is associated with a bone formation disease or condition. In some aspects, the inflammation is acute, chronic, or a combination thereof. In some aspects, the inflammation is a systemic inflammatory response, a local inflammatory response, an acute inflammatory condition, or a combination thereof.

In some aspects, the inflammation is associated with a disease or condition selected from: an arthritic condition, an allergic inflammatory response, a fibrotic condition, a sclerotic condition, a dermatologic condition, an ocular condition, a renal condition, a hepatic condition, a cardiac condition, a pancreatic condition, a cancer, a bone condition, a skin condition, asthma, an ischemic condition, a reperfusion injury, a central nervous system injury, a peripheral nervous system injury, an immunodeficiency or a combination thereof. In some aspects, the inflammation is associated with asthma.

The disease or condition treated according to the present methods can be selected from: solar urticaria, xeroderma pigmentosa, gingivitis, mucositis, diabetic retinopathy, retinopathy of prematurity, pancreatitis, juvenile rheumatoid arthritis, rheumatoid arthritis, osteoarthritis, acute gout, psoriatic arthritis, gout, pseudo gout, systemic lupus erythematosus, discoid lupus erythematosus, drug-induced lupus erythematosus, neonatal lupus erythematosus, erythropoietic protophyria, multiple sclerosis, polymyositis, dermatomyositis, autoimmune thrombocytopenia, autoimmune hemolytic anemia, drug-induced antibodies, drug reactions from administration of biologics, sarcoidosis, fibrosis, cirrhosis, renal failure, systemic sclerosis, idiopathic pulmonary fibrosis, hepatitis including toxic hepatitis, cardiac fibrosis, scarring, keloids, nephritis such as glomerulonephritis and interstitial nephritis, nephrotic syndrome, multiple sclerosis, infantile spasms, epilepsy, ulcerative colitis, uveitis, irritable bowel syndrome, solar urticaria, xeroderma pigmentosum, Crohn's disease, asthma, diabetes, vasculitis, retinal vasculitis, burns, dermatitis, radiation injury, thyroiditis, meningitis, encephalitis, peritonitis, pleuritis, endometriosis, peripheral neuropathy, shock, hypovolemic shock, septic shock, acute respiratory distress syndrome (ARDS), cerebrovascular disease, muscular dystrophy, cystic fibrosis, multiple myeloma, bone metastases, osteoporosis, osteopenia, psoriasis, stroke, cerebrovascular disease, amyotrophic lateral sclerosis, muscular dystrophy, myocardial infarction, myocardial ischemia, reperfusion injury, peripheral vascular disease, graft versus host disease, graft rejection, or a combination thereof. In some aspects, the disease or condition is selected from arthritis, which can include gout.

In some aspects, the administering according to the present disclosure comprises injecting the composition. In some aspects, the composition is administered topically, parenterally, intravenously, subcutaneously, via depot, intra-lesionally, intra-articularly, intramuscularly, intrathecally, intra-arterially, intranasally, intratracheally, via inhalation, sublingually, intranasally, intratracheally, or a combination thereof. In some aspects, the composition can be injected intra-articularly. In some aspects, the composition is injected locally at the site of inflammation.

Described herein are methods of making the compositions of the present disclosure, the method comprising recombinantly expressing the first polypeptide and the second polypeptide.

Described herein are methods of making the compositions of the present disclosure, the method comprising synthetically preparing the first polypeptide and the second polypeptide.

Described herein are methods of making the compositions of the present disclosure, the methods comprising synthetically preparing each polypeptide of a plurality of polypeptides. Described herein are methods of making the compositions of the present disclosure, the methods comprising expressing each polypeptide of a plurality of polypeptides.

Described herein are pharmaceutical compositions of the present compositions comprising the compositions and a pharmaceutically acceptable carrier. In some aspects, the pharmaceutical composition is formulated for injection. In some aspects, the pharmaceutical composition is formulated for subcutaneous injection. In some aspects, the pharmaceutical composition is formulated for intravenous injection. In some aspects, the pharmaceutical composition is formulated for intra-articular injection, injection into a tendon, or injection into a bursa. In some aspects, the pharmaceutical composition is formulated for oral administration. In some aspects, the pharmaceutical composition is formulated for sublingual administration. In some aspects, the pharmaceutical composition is formulated for intranasal administration. In some aspects, the pharmaceutical composition is formulated for intratracheal administration. The pharmaceutical composition can be formulated for administration via inhalation. In some aspects, the pharmaceutical composition is formulated for depot administration. In some aspects, the pharmaceutical composition is formulated for local injection. In various aspects, the depot administration is in the form of a microparticle, a nanoparticle, a liposome, a carbon nanotube, a micelle, or a thermosensitive hydrogel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
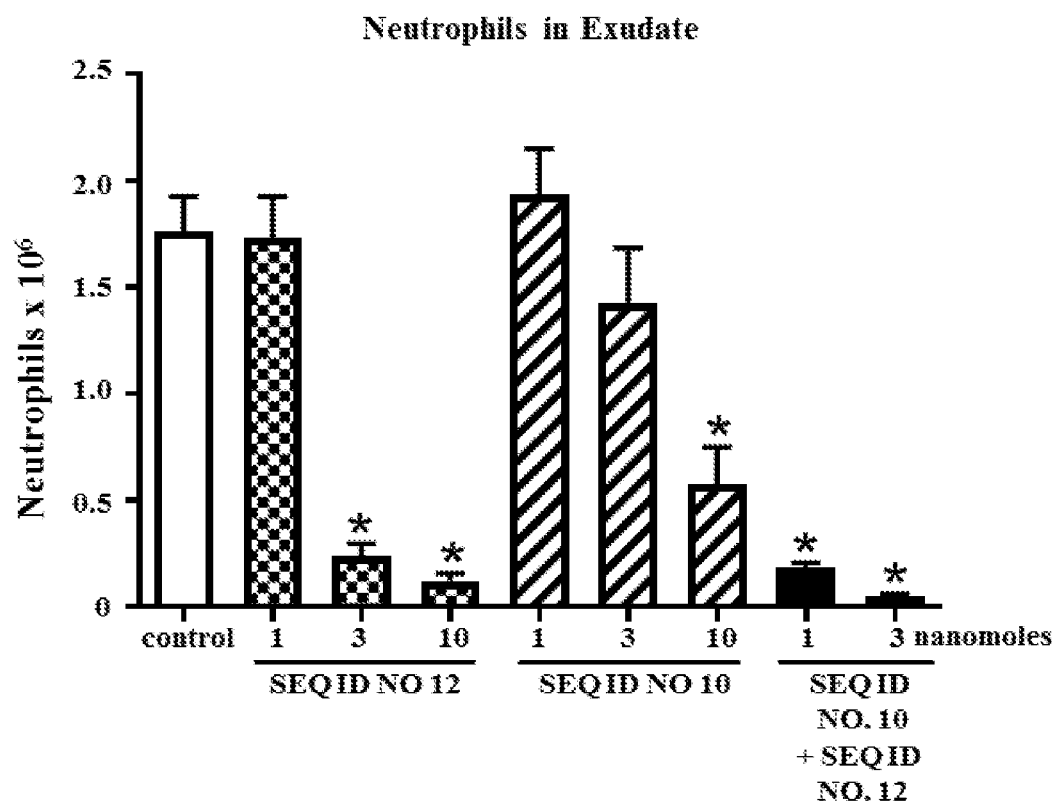
FIG. 1 shows neutrophil counts in collected exudate from murine models of gout treated with compositions disclosed herein.

The present disclosure provides compositions and methods for the treatment of inflammatory conditions and diseases and/or disorders that may be responsive to ACTH treatment. Compositions and methods herein disclose combinations of melanocortins, e.g., ACTH and at least one additional melanocortin, that may have enhanced therapeutic effects compared to ACTH alone, and may have decreased steroidogenic effects relative to ACTH.

ACTH has been used to treat a variety of inflammatory conditions, including chronic autoimmune diseases, such as systemic lupus erythematosus, polymyositis and glomerulonephritis as well as acute conditions such as acute attacks of gout and acute flares of multiple sclerosis, juvenile rheumatoid arthritis, and rheumatoid arthritis. ACTH stimulates the secretion of glucocorticoid steroid hormones, which can reduce inflammation, from adrenal cortex cells by binding melanocortin receptor type 2 (MC2R).

Melanocortins have been demonstrated to have significant therapeutic effects in neuroinflammation. Recently, it has been shown that inflammation may play a major role in epilepsy. ACTH has been shown to be effective in the treatment of subjects (e.g., patients) with a form of epilepsy in infants, infantile spasms. In some respects, treatment of subjects with proopiomelanocortin-derived melanocortins or variants thereof (e.g., compositions described herein, such as ACTH or MSH and variants thereof) can be used to treat various forms of epilepsy, including infantile spasms. In some respects, the treatment of epilepsy with compositions described herein may involve melanocortin receptor (e.g., MC2R) binding by the composition(s) and subsequent modulation (e.g., increase) of glucocorticoid production.

Although ACTH is effective in treating several disorders, improved clinical efficacy is desirable to increase response rates and patient outcomes. In addition, ACTH carries the risk of steroidogenic effects that may lead to complications associated with steroids, such as hypertension, Cushingoid appearance, weight gain, diabetes, infections, cataracts, edema, psychiatric disturbances, and osteoporosis. The increased efficacy of the melanocortin combinations described herein may decrease the dosage of ACTH necessary for a desired therapeutic effect, thereby reducing or eliminating the steroidogenic effects of ACTH.

The combinations of melanocortins disclosed herein may, in some cases, be provided as fusion polypeptides, e.g., ACTH covalently linked to a non-ACTH melanocortin, a melanocyte stimulating hormone (MSH) which can be a proopiomelanocortin-derived melanocortin and can include α-MSH, β-MSH, or γ-MSH, or a non-ACTH melanocortin linked to another non-ACTH melanocortin. A fusion polypeptide can comprise two polypeptides that are joined together (e.g., via chemical linkage, as in a covalent bond). A fusion polypeptide can comprise a plurality of polypeptides that are joined together (e.g., via chemical linkage, as in a covalent bond). The ACTH or non-ACTH melanocortin and MSH polypeptides may be joined by a peptide linker comprising a cleavage site recognized by endogenous proteases, e.g., serine proteases, cysteine proteases, aspartate proteases, threonine proteases, glutamic acid proteases, metalloproteinases, proprotein convertases, asparagine peptide lyases, trypsin, chymotrypsin, cathepsin, etc. These cleavage sites may be specific to proteases that are involved with pathological processes such as inflammation (e.g., proprotein convertases and metalloproteinases). Cleavage sites may be specific to proteases that are present throughout the body or selectively expressed at sites of a disease or disorder, e.g., a site of inflammation. The fusion polypeptides can be administered locally or systemically, and cleavage at a target site, e.g., a site of inflammation, can release the melanocortins locally. This can reduce off-target toxicity associated with individual melanocortin peptides. Additionally, the fused polypeptides may have longer half-lives compared to the individual peptides due to increased size and, in some cases, may be more efficiently manufactured. Alternatively, they can be attached to moieties that prolong their half-life, such as Fc domains of immunoglobulins.

Melanocortin Peptides and Receptors

The melanocortin system consists of five receptors, which have been identified to date (MC1-5R), melanocortin agonists derived from the proopiomelanocortin prohormone (POMC) and two naturally existing antagonists.

Named originally for their effects on the first discovered cellular target, the melanocyte, the melanocortin system controls a diverse set of physiological processes through a series of five G-protein-coupled receptors (MC1-5R) and several sets of small peptide ligands. More recently, the melanocortin system has been shown to participate in the regulation of the immune system, including inflammatory responses.

Melanocortin agonists, herein also referred to as "melanocortins," are peptides derived from proteolytic cleavage of proopiomelanocortin (POMC). This pro-hormone, as well as melanocortins, were first thought to be expressed only within the pituitary but later found to also be expressed by many other cells and tissues. The terms "polypeptide" and "peptide" are used interchangeably to refer to a sequence of two or more amino acids joined together by peptide bonds or non-peptide linkers such as chemical linkage. This term does not connote a specific length of a polymer of amino acids, nor is it intended to imply or distinguish whether the polypeptide is produced using recombinant techniques, chemical or enzymatic synthesis, or is naturally occurring. The terms "amino acid" and "amino acids," as used herein, generally refer to natural and non-natural amino acids, including, but not limited to, modified amino acids and amino acid analogs. Modified amino acids can include natural amino acids and non-natural amino acids, which have been chemically modified to include a group, groups, or a chemical moiety not naturally present on the amino acid. Amino acid analogs may refer to amino acid derivatives. The term "amino acid" includes both D-amino acids and L-amino acids.

Proopiomelanocortin (POMC, herein also referred to as "pro-opiomelanocortin") is a precursor polypeptide synthesized from the polypeptide precursor pre-proopiomelanocortin (pre-POMC). During translation, POMC is formed by removing a signal peptide from pre-POMC. The enzymes proprotein convertase 1 (PC1) and 2 (PC2), which belong to a conserved family of serine proteinases of the subtilisin/kexin-type, act upon single and/or pairs of dibasic residues within the POMC sequence to generate melanocortin peptides, including adrenocorticotropic hormone (ACTH) and the melanocyte stimulating hormones (MSHs): α-MSH, β-MSH, and γ-MSH. PC1 leads to generation of full-length pro-$ACTH_{1-39}$ and β-lipotropin. PC1 can then further cleave β-lipotropin to generate γ-lipotropin and β-endorphin (SEQ ID NO. 16), and pro-ACTH to generate N-pro-opiocortin (POC), joining peptide (JP), and ACTH. The down-stream actions of PC2 result in production of $ACTH_{1-17}$ and corticotrophin-like intermediate lobe peptide (CLIP, from ACTH), γ-MSH (from N-POC), and β-MSH (from γ-lipotropin). Alpha-MSH (αMSH) is generated by the combined actions of carboxypeptidase (CPE), peptidylglycine alpha-amidating mono-oxygenase (PAM), and N-acetyltransferase (N-AT) on $ACTH_{1-17}$.

The biological activity of melanocortins such as adrenocorticotropic hormone (ACTH) and melanocyte stimulating hormone (MSH), which are derivatives of proopiomelanocortins, occurs through activation of melanocortin receptors (MCRs) of which five have been cloned (e.g., MC1R, MC2R, MC3R, MC4R, and MC5R). The melanocortin receptors are G protein-coupled receptors that signal via the cyclic AMP (cAMP) pathway, activating adenylate cyclase that results in increased intracellular cyclic AMP. MC1R is commonly expressed on melanocytes. MC1R is also reported to be expressed in various other cells, including those involved in immune responses, such as monocytes, neutrophils, lymphocytes, dendritic cells, natural killer (NK)

cells and endothelial cells. MC2R is expressed on adrenal cells and involved in glucocorticoid synthesis and release. The biological functions of MC3R, MC4R, and MC5R, have been defined in part. For example, MC1R and MC3R have been shown to have a major role in host inflammatory responses, and is expressed in a variety of white blood cells. Recent studies of MC5R show that it plays a role in inflammation and immunoregulation. Adrenocorticotropic hormone (ACTH) is a 39 amino acid polypeptide (e.g., $ACTH_{1-39}$) hormone having the amino acid sequence SYSMEHFRWGKPVGKKRRPVKVYPNGAEDESAEAFPLEFKR (SEQ ID NO. 19). ACTH can exist in a truncated form as $ACTH_{1-24}$ (SEQ ID NO. 10). In the adrenal gland, ACTH binding to MC2R can stimulate the production of glucocorticoids and mineralocorticoids. In addition to stimulating glucocorticoid production, ACTH, may also be involved in anti-inflammatory effects, independent of glucocorticoids. The combined effects of glucocorticoids and other anti-inflammatory effects make ACTH peptides useful as therapeutics for inflammatory conditions.

The melanocyte-stimulating hormones (e.g., α-MSH, β-MSH, and γ-MSH) were originally identified as products of cells in the pars intermedia of the pituitary gland. More recently, they have been documented to be produced in many other tissues and organs, including several types of white blood cells. Alpha-MSH (α-MSH) is a polypeptide 13 amino acids in length having the amino acid sequence SYSMEHFRWGKPV-NH2 (SEQ ID NO. 11). Alpha-MSH (α-MSH) is naturally acetylated at the N-terminus and generated as a proteolytic cleavage product from ACTH. Alpha-MSH (α-MSH) acts as an agonist for the receptors MC1R, MC3R, MC4R and MC5R. Synthetic analogues have been developed as receptor agonists and antagonists. Examples of α-MSH analogues include the linear synthetic peptide Afamelanotide (also known as melanotan I or NDP-α-MSH) and the cyclized synthetic peptides melanotan II and Bremelanotide. The synthetic peptide NDP-α-MSH is a potent analog having the amino acid sequence SYS-Nle-EH-DPhe-RWGKPV-NH2 (SEQ ID NO. 12), wherein Nle is a norleucine amino acid and DPhe is a D-phenylalanine. Beta-MSH is a polypeptide that is 22 amino acids in length with the amino acid sequence AEKKDEGPYRMEHFRWGSPPKD (SEQ ID NO. 17). Beta-MSH (β-MSH) also acts as a non-selective agonist, and binds with low affinity to the receptors MC1R, MC3R, MC4R and MC5R. Gamma1-MSH (γ1-MSH, herein also referred to as γ-MSH) is a polypeptide that is 12 amino acids in length having the amino acid sequence YVMGHFRWDRFG (SEQ ID NO. 20). Gamma-MSH (γ-MSH) primarily binds to MC3R. It can exist in two alternative forms, γ2-MSH and γ3-MSH. Gamma2-MSH (γ2-MSH) exists as a polypeptide, which is 11 amino acids in length. It has the amino acid sequence YVMGHFRWDRF (SEQ ID NO. 88) while γ3-MSH has an extended C-terminus. Synthetic analogues of γ1-MSH have been developed as receptor agonists and antagonists. Examples of γ-MSH analogues include cyclic lactam analogues of γ-MSH and the synthetic peptide having the amino acid sequence YV-Nle-GH-DPhe-RWDRFG (SEQ ID NO. 18), also referred to as NDP-γ-MSH.

Acetylation of proopiomelanocortin fragments or variants thereof can increase the solubility of a composition through, for example, the process of conjugation. In some cases, increased drug solubility can affect excretion of the composition by the kidneys and/or secretion in bile. In some respects, acetylation of proopiomelanocortin fragments or variants thereof can affect plasma half-life of the composition.

In some respects, amino acid substitution can improve aspects of NDP-MSH function. For example, substitution of Nle for Met at position 4 in α-MSH (as in SEQ ID NO. 12) can result in reduced oxidation at position 4 Similarly, the plasma half-life of the NDP α-MSH can be improved over natural α-MSH by incorporating Nle and DPhe in α-MSH at positions 4 and 7, respectively, as in SEQ ID NO. 12. As a result, the compositions disclosed herein can result in drugs with improved efficacy through reduced oxidation and/or increased plasma half-life. Fragments of ACTH (and analogously α-MSH), such as amino acid residues 4-10 of SEQ ID NO. 19 or SEQ ID NO. 11 (MEHFRWG) and amino acid residues 11-13 of SEQ ID NO. 19 or SEQ ID NO. 11 (KPV) have various degrees of anti-inflammatory activity. The tetrapeptide sequence HFRW (SEQ ID NO. 35), or amino acid residues 6-9 of SEQ ID NO. 19, can be found in ACTH, α-MSH, β-MSH, and γ-MSH. The sequence HFRW may be involved in MCR binding and activation.

A steroidogenic response, in which cholesterol is delivered to the mitochondria and converted into steroids of the progestogen, corticosteroid, androgen, and estrogen classes in a process catalyzed by the activity of a side chain cleavage enzyme P450scc (also known as Cyp11a1), can be induced by ACTH. ACTH can also stimulate the production of mineralocorticoids. Rapid effects of steroidogenesis induced by ACTH can include increased lipoprotein uptake in cortical cells and bioavailability of cholesterol in the adrenal cortex, while longer effects can include increased transcription of steroidogenic enzymes, 11b-hydroxylase, electron transfer proteins, and mitochondrial oxidative phosphorylation system subunits. Increased production of glucocorticoids is known to affect immune cell activation and function and can impact immune system function and inflammatory responses. In some respects, production of steroid hormones, such as mineralocorticoids, can affect fluid retention through modulation of electrolyte and water balance.

Half-Life Extending Moieties

Polypeptides of the compositions herein may be conjugated or linked to half-life extending moieties. The term "half-life extending moiety" refers to a pharmaceutically acceptable moiety, domain, or "vehicle" that can be linked to a peptide, e.g., via a linker. Mechanisms by which the half-life extending moiety positively influences pharmacokinetic or pharmacodynamic behavior may include (i) preventing or mitigating in vivo proteolytic degradation or other activity-diminishing chemical modifications, (ii) improving half-life or other pharmacokinetic properties by reducing renal filtration, decreasing receptor-mediated clearance or increasing bioavailability, (iii) reducing toxicity, (iv) improving solubility, (v) increasing biological activity and/or target selectivity. In addition, a half-life extending moiety may have positive effects on manufacturability and/or reducing immunogenicity compared to an unconjugated form of the peptide. Non-limiting examples of half-life extending moieties include non-proteinaceous moieties such as polyethylene glycol (PEG) and hydroxyethyl starch (HES), and proteinaceous moieties such as albumin (e.g., serum albumin), glycopeptides, glycopolymers, transferrin, and Fc domains of immunoglobulins.

Glycopolymers refer to therapeutically useful polypeptides and fragments, or variants thereof, conjugated to one or more amino acid extensions of variable length. The amino acid extensions may comprise a block copolymer arrangement of repeating glycan acceptor motifs separated by spacer motifs, (or "glycosylated amino acid block copolymer-based polypeptides"). Accordingly, these polypeptides may comprise at least two glycan acceptor motifs separated by a spacer motif. The glycosylated amino acid block copolymer-based polypeptides-conjugated therapeutically useful peptides may possess half-lives that are increased when compared to their corresponding unmodified therapeutically useful peptides.

Modulation of Melanocortin Receptor Activity for Therapeutic Effects

Provided herein are compositions comprising two or more peptides derived from POMC, or variants thereof, for the treatment of diseases and disorders, e.g., disorders associated with inflammation. The terms "treat," "treating" and "treatment," as used herein, refer to an action that occurs while a patient is suffering from the specified disease or disorder, which reduces the severity of the disease or disorder. The terms "prophylactically treat," "prophylactically treating" and "prophylactic treatment," as used herein, refer to an action that occurs before a patient is suffering from symptoms of a specified disease or disorder, which either prevents the occurrence of the disease or disorder or reduces the severity of the disease or disorder if there is subsequent onset. Compositions herein may be delivered in a therapeutically effective amount for a curative effect and/or prophylactic effect. The term "therapeutically effective amount" refers to the amount of a composition herein sufficient to elicit a biological or medical response in the subject that is being treated. In some respects, compositions herein may be delivered to an infant or a child, and the administration of such compositions to an infant or a child can comprise an action that occurs while the infant or child is suffering from a specified disease or disorder. In some embodiments, such administration of a composition described herein can reduce the severity of the disease or disorder.

Compositions herein for the treatment or prophylactic treatment of diseases and disorders, e.g., inflammatory diseases and disorders, may comprise two or more peptides derived from POMC for the modulation of two or more MCRs. For example, a composition herein may modulate MC1R and at least one of MC2R, MC3R, MC4R, and MC5R. As an alternative, a composition herein may modulate MC2R and at least one of MC1R, MC3R, MC4R and MC5R. In some cases, compositions modulate MC3R and at least one of MC1R, MC2R, MC4R, and MC5R. A composition herein may, in some cases, modulate MC4R and at least one of MC1R, MC2R, MC3R, and MC5R. For further example, a composition herein may modulate MC5R and at least one of MC1R, MC2R, MC3R, and MC4R. In compositions disclosed herein, ACTH, or variants thereof, may be supplied for the modulation of MC2R. At least one of α-MSH, β-MSH, γ-MSH, or variant thereof, can be used for the modulation of MC1R, MC3R, MC4R and MC5R. Compositions herein can modulate melanocortin receptors (e.g., MC1R, MC2R, MC3R, MC4R, and/or MC5R) by affecting the affinity or bioactivity of a receptor.

In some cases, a composition herein comprises an ACTH peptide, or variant thereof, and an α-MSH peptide, or a variant thereof. An ACTH peptide of any composition or method disclosed herein may refer to a full length peptide (e.g., $ACTH_{1-39}$) or a truncated variant (e.g., $ACTH_{1-24}$, $ACTH_{1-17}$, $ACTH_{4-10}$, $ACTH_{4-9}$, $ACTH_{6-9}$, and $ACTH_{11-13}$) An ACTH variant may have a sequence that is at least 50% identical (e.g., at least 55%, 60%, 65%, 70%, 75%, 80%, 85%, 90%, 95% identical or greater) to SEQ ID NO. 19, SEQ ID NO. 10 or SEQ ID NO. 47 or may have a sequence of a truncated variant, e.g., SEQ ID NO. 35 and SEQ ID NO. 36. In some cases, the variant may be acetylated. A variant may comprise at least one of an amino acid mutation compared to the wild-type sequence, an amino acid analogue, a non-natural amino acid, an amino acid isomer, or combinations thereof. An ACTH variant may have a sequence of any one of $ACTH_{1-39}$, $ACTH_{1-24}$, $ACTH_{1-17}$, $ACTH_{4-10}$, $ACTH_{4-9}$, $ACTH_{6-9}$, and $ACTH_{11-13}$ and at least one amino acid mutation or modification (e.g., at least two, at least three or more than three amino acid mutations and/or modifications). For example, an ACTH variant may comprise the amino acid sequence MEHFRW (SEQ ID NO. 30) and one or more amino acid mutations and/or analogues such as the variant provided in SEQ ID NO. 31 (Nle-EH-dPhe-RW). As α-MSH is generated as a proteolytic cleavage product from ACTH and also contains the sequence MEHFRW, a truncated α-MSH variant may also refer to MEHFRW (SEQ ID NO. 30) and a variant thereof may refer to SEQ ID NO. 31.

An α-MSH peptide of any composition or method disclosed herein may refer to a full length peptide or a truncated variant. An α-MSH variant may have a sequence that is at least 50% identical (e.g., at least 55%, 60%, 65%, 70%, 75%, 80%, 85%, 90%, 95% identical or greater) to SEQ ID NO. 11. An α-MSH variant may comprise at least of an amino acid mutation compared to the wild-type sequence, an amino acid analogue, a non-natural amino acid, an amino acid isomer, or combinations thereof, e.g. NDP-α-MSH (SEQ ID NO. 12) or Ac-NDP-α-MSH (SEQ ID NO. 72). ACTH (e.g., $ACTH_{1-39}$, $ACTH_{1-24}$, NDP-$ACTH_{1-24}$, $ACTH_{1-17}$, $ACTH_{4-10}$, $ACTH_{4-9}$, NDP-$ACTH_{4-9}$, $ACTH_{6-9}$, and $ACTH_{11-13}$) and α-MSH (e.g., NDP-α-MSH or Ac-NDP-α-MSH) may be provided in any suitable amount and at any suitable ratio for a desired therapeutic effect. A dosage, e.g., a therapeutic dosage, may comprise the two peptides provided at approximately equal amounts (e.g., about 1 nanomole (nmole) ACTH:1 nmole NDP-α-MSH or Ac-NDP-α-MSH, about 5 nmole ACTH:5 nmole NDP-α-MSH or Ac-NDP-α-MSH, about 10 nmole ACTH:10 nmole NDP-α-MSH or Ac-NDP-α-MSH, about 15 nmole ACTH:15 nmole NDP-α-MSH or Ac-NDP-α-MSH, about 25 nmole ACTH:25 nmole NDP-α-MSH or Ac-NDP-α-MSH, about 35 nmole ACTH:35 nmole NDP-α-MSH or Ac-NDP-α-MSH, about 45 nmole ACTH:45 nmole NDP-α-MSH or Ac-NDP-α-MSH, about 50 nmole ACTH:50 nmole NDP-α-MSH or Ac-NDP-α-MSH, about 60 nmole ACTH:60 nmole NDP-α-MSH or Ac-NDP-α-MSH, about 75 nmole ACTH:75 nmole NDP-α-MSH or Ac-NDP-α-MSH, about 85 nmole ACTH:85 nmole NDP-α-MSH or Ac-NDP-α-MSH, etc, about 95 nmole ACTH:95 nmole NDP-α-MSH or Ac-NDP-α-MSH, about 100 nmole ACTH:100 nmole NDP-α-MSH or Ac-NDP-α-MSH.). In some cases, the two peptides are not provided at approximately equal amounts. For example, the two peptides may be provided at a stoichiometric molar ratio of about 0.1:1, 0.25:1, 0.33:1, 0.5:1, 1:1, 2:1, 3:1, 4:1, 5:1, or 10:1. In some cases, the stoichiometric molar ratio may be at least 10:1 (e.g., at least 15:1, 20:1, 25:1 or greater). Therapeutic dosage may be optimized to account for various parameters, including, but not limited to, the pharmaceutical formulation and/or route of administration; the age of the patient and/or the severity of the disease; and the stability of the peptides and/or serum half-life. A composition herein may, as an alternative, comprise a combination of an ACTH peptide, or variant thereof, and a γ-MSH peptide, or a variant thereof. A γ-MSH peptide of any composition or method disclosed herein may refer to a full length peptide or a truncated variant. A γ-MSH variant may have a sequence that is at least 50% identical (e.g., at least 55%, 60%, 65%, 70%, 75%, 80%, 85%, 90%, 95% identical or greater) to SEQ ID NO. 19 or SEQ ID NO. 20. A γ-MSH variant may comprise at least one of an amino acid mutation compared to the wild-type sequence, an amino acid analogue, a non-natural amino acid, an amino acid isomer, or combinations thereof, e.g., NDP-γ-MSH.

TABLE 1

Melanocortin variants and fusion polypeptides.

| SEQ ID NO. | Description | Sequence |
|---|---|---|
| 1 | γ-MSH-ACTH$_{1-24}$ | YVMGHFRWDRFGKRSYSMEHFRWGKPVGKKRRPVKVYP |
| 2 | γ-MSH-ACTH$_{1-24}$ with natural linker | YVMGHFRWDRFGRRNSSSSGSSGAGQKRSYSMEHFRWGKPVGKKRRPVKVYP |
| 3 | NDP-γ-MSH-ACTH$_{1-24}$ | YV-Nle-GH-DPhe-RWDRFGKRSYSMEHFRWGKPVGKKRRPVKVYP |
| 4 | γ-MSH-α-MSH | YVMGHFRWDRFGKRSYSMEHFRWGKPV-NH2 |
| 5 | γ-MSH-α-MSH with natural linker | YVMGHFRWDRFGRRNSSSSGSSGAGQKRSYSMEHFRWGKPV-NH2 |
| 6 | NDP-γ-MSH-α-MSH | YV-Nle-GH-DPhe-RWDRFGKRSYSMEHFRWGKPV-NH2 |
| 7 | γ-MSH-NDP-α-MSH | YVMGHFRWDRFGKRSYS-Nle-EH-DPhe-RWGKPV-NH2 |
| 8 | NDP-γ-MSH-NDP-α-MSH | YV-Nle-GH-DPhe-RWDRFGKRSYS-Nle-EH-DPhe-RWGKPV-NH2 |
| 9 | γ-MSH with linker | YVMGHFRWDRFGRRNSSSSGSSGAGQKR |
| 10 | ACTH$_{1-24}$ | SYSMEHFRWGKPVGKKRRPVKVYP |
| 11 | α-MSH | SYSMEHFRWGKPV-NH2 |
| 12 | NDP-α-MSH | SYS-Nle-EH-DPhe-RWGKPV-NH2 |
| 13 | γ-MSH-ACTH$_{1-39}$ without linker | YVMGHFRWDRFGKRSYSMEHFRWGKPVGKKRRPVKVYPNGAEDESAEAFPLEFKR |
| 14 | γ-MSH-ACTH$_{1-24}$ linker without cleavable site | YVMGHFRWDRFGRRNSSSSGSSGAGQSYSMEHFRWGKPVGKKRRPVKVYP |
| 15 | γ-MSH-ACTH$_{1-24}$ without linker and cleavage site | YVMGHFRWDRFGSYSMEHFRWGKPVGKKRRPVKVYP |
| 16 | β-endorphin | YGGFMTSEKSQTPLVTLFKNAIIKNAYKKGE |
| 17 | β-MSH | AEKKDEGPYRMEHFRWGSPPKD |
| 18 | NDP-γ-MSH | YV-Nle-GH-(DPhe)-RWDRFG |
| 19 | ACTH$_{1-39}$ | SYSMEHFRWGKPVGKKRRPVKVYPNGAEDESAEAFPLEFKR |
| 20 | γ-MSH | YVMGHFRWDRFG |
| 21 | Delta POMC glycopolymer | SYSMEHFRWGKPVGKKRRPVKVYPNGAEDESAEAFPLEFKRELTGQRLREGDGPDGPADDGAGAQADLEHSLLVAAEKKDEGPYRMEHFRWGSPPKDKRYGGFMGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGSGGSNNTGGSGGS |

TABLE 1-continued

Melanocortin variants and fusion polypeptides.

| SEQ ID NO. | Description | Sequence |
|---|---|---|
| 22 | γ-MSH-ACTH$_{1-39}$ fusion protein | EVRGWCLESSQCQDLTTESNLLECIR ACKPDLSAETPMFPGNGDEQPLTENP RKYVMGHFRWDRFGRRNSSSSGSSG AGQKREDVSAGEDCGPLPEGGPEPRS DGAKPGPREGKRSYSMEHFRWGKPV GKKRRPVKVYPNGAEDESAEAFPLE FKRAEKKDEGPYRMEHFRWGSPPKD GGSGGS |
| 23 | NDP-α-MSH-linker-linker-ACTH$_{1-24}$ | Ac-SYS-Nle-EH-DPhe-RWGKPV-GGGGSGGGGS SYSMEHFRWGKPVGKKRRPVKVYP |
| 24 | NDP-α-MSH-linker-Furin site-linker-ACTH$_{1-24}$ | Ac-SYS-Nle-EH-DPhe-RWGKPV-GGGGSRRKRGGGGS-SYSMEHFRWGKPVGKKRRPVKVYP |
| 25 | NDP-α-MSH-linker-MMP site-linker-ACTH$_{1-24}$ | Ac-SYS-Nle-EH-DPhe-RWGKPV-GGGGSPLGLWAGGGGS-SYSMEHFRWGKPVGKKRRPVKVYP |
| 26 | ACTH$_{1-24}$-linker-linker-NDP-α-MSH | SYSMEHFRWGKPVGKKRRPVKVYP-GGGGSGGGGS-SYS-Nle-EH-DPhe-RWGKPV |
| 27 | ACTH$_{1-24}$-linker-Furin site-linker-NDP-α-MSH | SYSMEHFRWGKPVGKKRRPVKVYP-GGGGSRRKRGGGGS-SYS-Nle-EH-DPhe-RWGKPV |
| 28 | ACTH$_{1-24}$-linker-MMP site-linker-NDP-α-MSH | SYSMEHFRWGKPVGKKRRPVKVYP-GGGGSPLGLWAGGGGS-SYS-Nle-EH-DPhe-RWGKPV |
| 29 | ACTH$_{1-24}$-linker-MMP (broad) site-linker-NDP-α-MSH | SYSMEHFRWGKPVGKKRRPVKVYP-GGGGSPAGLVAGGGGS-SYS-Nle-EH-DPhe-RWGKPV |
| 30 | ACTH$_{4-9}$ | MEHFRW |
| 31 | NDP-ACTH$_{4-9}$ | Nle-EH-dPhe-RW |
| 32 | NDP-α-MSH-linker-MMP (broad) site-linker-ACTH$_{1-24}$ | Ac-SYS-Nle-EH-DPhe-RWGKPV-GGGGSPAGLVAGGGGS-SYSMEHFRWGKPVGKKRRPVKVYP |
| 33 | Acetylated α-MSH | Ac-SYSMEHFRWGKPV-NH2 |
| 34 | HFRWKPV-NH2 | HFRWKPV-NH2 |
| 35 | HFRW | HFRW |
| 36 | KPV-NH2 | KPV-NH2 |
| 37 | KPVHFRW | KPVHFRW |
| 38 | ACTH$_{1-24}$-proconvertase-NDP-α-MSH | SYSMEHFRWGKPVGKKRRPVKVYP-GGGGSRRKR-SYS-Nle-EH-DPhe-RWGKPV |
| 39 | ACTH$_{1-24}$-natural N-terminal spacer-NDP-α-MSH | SYSMEHFRWGKPVGKKRRPVKVYP-PLPEGGPEPRSDGAKPGPREGKR-SYS-Nle-EH-DPhe-RWGKPV |
| 40 | ACTH$_{1-24}$-natural C-terminal space-NDP-α-MSH | SYSMEHFRWGKPVGKKRRPVKVYP-ELTGQRLREGDGPDGPADDGAGA-SYS-Nle-EH-DPhe-RWGKPV |
| 41 | ACTH$_{1-24}$-proconvertase-α-MSH | SYSMEHFRWGKPVGKKRRPVKVYP GGGGSRRKR-SYSMEHFRWGKPV |
| 42 | ACTH$_{1-24}$-natural N-terminal spacer-α-MSH | SYSMEHFRWGKPVGKKRRPVKVYP-PLPEGGPEPRSDGAKPGPREGKR-SYSMEHFRWGKPV |

TABLE 1-continued

Melanocortin variants and fusion polypeptides.

| SEQ ID NO. | Description | Sequence |
|---|---|---|
| 43 | ACTH$_{1-24}$-natural C-terminal spacer-α-MSH | SYSMEHFRWGKPVGKKRRPVKVYP-ELTGQRLREGDGPDGPADDGAGA-SYSMEHFRWGKPV |
| 44 | NDP-ACTH$_{4-9}$-βAla-G-β-Ala-NDP-ACTH$_{4-9}$ | Nle-EH-dPhe-RW-β-Ala-G-β-Ala-Nle-EH-dPhe-RW |
| 45 | NDP-ACTH$_{4-9}$-βAla-G-β-Ala-ACTH$_{1-24}$ | Nle-EH-dPhe-RW-β-Ala-G-β-Ala-SYSMEHFRWGKPVGKKRRPVKVYP |
| 46 | NDP-ACTH$_{4-9}$-ACTH$_{1-24}$ | Nle-EH-dPhe-RWSYSMEHFRWGKPVGKKRRPVKVYP |
| 47 | NDP-ACTH | SYS-Nle-EH-DPhe-RWG KPVGKKRRPV KVYP |
| 48 | ACTH$_{1-24}$-point-5 | SYSMEHFRWGKPVGKKRRAVKVYP |
| 49 | ACTH$_{1-24}$-point-1-2 | SYSMEHFRWGKPVGAARRPVKVYP |
| 50 | ACTH$_{1-24}$-point-3-5 | SYSMEHFRWGKPVGKKAAAVKVYP |
| 51 | ACTH$_{1-24}$-NDP-α-MSH | SYSMEHFRWGKPVGKKRRPVKVYPS YS-Nle-EH-DPhe-RWGKPV |
| 52 | ACTH$_{1-24}$-point-5-NDP-α-MSH | SYSMEHFRWGKPVGKKRRAVKVYP SYS-Nle-EH-DPhe-RWGKPV |
| 53 | ACTH$_{1-24}$-point-1-2-NDP-α-MSH | SYSMEHFRWGKPVGAARRPVKVYPS YS-Nle-EH-DPhe-RWGKPV |
| 54 | ACTH$_{1-24}$-point-3-5-NDP-α-MSH | SYSMEHFRWGKPVGKKAAAVKVYP SYS-Nle-EH-DPhe-RWGKPV |
| 55 | ACTH$_{1-24}$-4aa-NDP-α-MSH | SYSMEHFRWGKPVGKKRRPVKVYP-GGGS-SYS-Nle-EH-DPhe-RWGKPV |
| 56 | ACTH$_{1-24}$-point-5-4aa-NDP-α-MSH | SYSMEHFRWGKPVGKKRRAVKVYP-GGGS-SYS-Nle-EH-DPhe-RWGKPV |
| 57 | ACTH$_{1-24}$-point-1-2-4aa-NDP-α-MSH | SYSMEHFRWGKPVGAARRPVKVYP-GGGS-SYS-Nle-EH-DPhe-RWGKPV |
| 58 | ACTH$_{1-24}$-point-3-5-4aa-NDP-α-MSH | SYSMEHFRWGKPVGKKAAAVKVYP-GGGS-SYS-Nle-EH-DPhe-RWGKPV |
| 59 | ACTH$_{1-24}$-7aa-NDP-α-MSH | SYSMEHFRWGKPVGKKRRPVKVYP-GGGGSGG-SYS-Nle-EH-DPhe-RWGKPV |
| 60 | ACTH$_{1-24}$-point-5-7aa-NDP-α-MSH | SYSMEHFRWGKPVGKKRRAVKVYP-GGGGSGG-SYS-Nle-EH-DPhe-RWGKPV |
| 61 | ACTH$_{1-24}$-point-1-2-7aa-NDP-α-MSH | SYSMEHFRWGKPVGAARRPVKVYP-GGGGSGG-SYS-Nle-EH-DPhe-RWGKPV |
| 62 | ACTH$_{1-24}$-point-3-5-7aa-NDP-α-MSH | SYSMEHFRWGKPVGKKAAAVKVYP-GGGGSGG-SYS-Nle-EH-DPhe-RWGKPV |
| 63 | ACTH$_{1-24}$-point-5-10aa-NDP-α-MSH | SYSMEHFRWGKPVGKKRRAVKVYP-GGGGSGGGGS-SYS-Nle-EH-DPhe-RWGKPV |
| 64 | ACTH$_{1-24}$-point-1-2-10aa-NDP-α-MSH | SYSMEHFRWGKPVGAARRPVKVYP-GGGGSGGGGS-SYS-Nle-EH-DPhe-RWGKPV |
| 65 | ACTH$_{1-24}$-point-3-5-10aa-NDP-α-MSH | SYSMEHFRWGKPVGKKAAAVKVYP-GGGGSGGGGS-SYS-Nle-EH-DPhe-RWGKPV |

TABLE 1-continued

Melanocortin variants and fusion polypeptides.

| SEQ ID NO. | Description | Sequence |
|---|---|---|
| 66 | NDP-ACTH$_{4-9}$-βAla-G-βAla-ACTH$_{1-24}$-βAla-G-βAla-NDP-ACTH$_{4-9}$ | (Nle-EH-dPhe-RW)-(βAla-Gly-βAla)-SYSMEHFRWGKPVGKKRRPVKVYP-(βAla-Gly-βAla)-(Nle-EH-dPhe-RW) |
| 67 | NDP-ACTH$_{4-9}$-βAla-G-βAla-NDP-ACTH$_{4-9}$-βAla-G-βAla-ACTH$_{1-24}$-βAla-G-βAla-NDP-ACTH$_{4-9}$-βAla-G-βAla-NDP-ACTH$_{4-9}$ | (Nle-EH-dPhe-RW)-(βAla-Gly-βAla)-(Nle-EH-dPhe-RW)-(βAla-Gly-βAla)-SYSMEHFRWGKPVGKKRRPVKVYP-(βAla-Gly-βAla)-(Nle-EH-dPhe-RW)-(βAla-Gly-βAla)-(Nle-EH-dPhe-RW) |
| 68 | NDP-ACTH$_{4-9}$-βAla-G-βAla-ACTH$_{1-24}$-βAla-G-βAla-NDP-ACTH$_{4-9}$-βAla-G-βAla-NDP-ACTH$_{4-9}$ | (Nle-EH-dPhe-RW)-(βAla-Gly-βAla)-SYSMEHFRWGKPVGKKRRPVKVYP-(βAla-Gly-βAla)-(Nle-EH-dPhe-RW)-(βAla-Gly-βAla)-(Nle-EH-dPhe-RW) |
| 69 | NDP-ACTH$_{4-9}$-βAla-G-βAla-NDP-ACTH$_{4-9}$-βAla-G-βAla-ACTH$_{1-24}$-βAla-G-βAla-NDP-ACTH$_{4-9}$ | (Nle-EH-dPhe-RW)-(βAla-Gly-βAla)-(Nle-EH-dPhe-RW)-(βAla-Gly-βAla)-SYSMEHFRWGKPVGKKRRPVKVYP-(βAla-Gly-βAla)-(Nle-EH-dPhe-RW) |
| 70 | ACTH$_{1-24}$-βAla-G-βAla-NDP-ACTH$_{4-9}$ | SYSMEHFRWGKPVGKKRRPVKVYP-(βAla-Gly-βAla)-(Nle-EH-dPhe-RW) |
| 71 | Ac-NDP-ACTH$_{4-9}$-βAla-G-βAla-ACTH$_{1-24}$ | Ac-(Nle-EH-dPhe-RW)-(βAla-Gly-βAla)-SYSMEHFRWGKPVGKKRRPVKVYP |
| 72 | Ac-NDP-α-MSH | Ac-SYS-Nle-EH-DPhe-RWGKPV |

A truncated variant of any one of ACTH, α-MSH, β-MSH, and γ-MSH may refer to the tetrapeptide sequence HFRW (SEQ ID NO. 35) as this sequence can be found in all four peptides. A composition herein may comprise a combination of the tetrapeptide HFRW linked to an ACTH peptide or a variant thereof (e.g., ACTH$_{1-39}$, ACTH$_{11-24}$, NDP-ACTH$_{1-24}$, ACTH$_{1-17}$, ACTH$_{4-10}$, ACTH$_{4-9}$, NDP-ACTH$_{4-9}$, ACTH$_{6-9}$, and ACTH$_{11-13}$) as a fusion polypeptide, such as provided in SEQ ID NO. 34 and SEQ ID NO. 37.

A composition herein may comprise a combination of ACTH peptide, or variant thereof, and one or more MSH peptides (e.g., α-MSH, β-MSH, and γ-MSH), or variant thereof, provided as a fusion polypeptide. An MSH peptide may refer to a full length peptide or a truncated variant. A MSH peptide of any composition or method disclosed herein may have a sequence that is at least 50% identical (e.g., at least 55%, 60%, 65%, 70%, 75%, 80%, 85%, 90%, 95% identical or greater) to SEQ ID NO. 11, SEQ ID NO. 17, SEQ ID NO. 9, or SEQ ID NO. 20. An MSH variant may comprise at least one of an amino acid mutation compared to a wild-type sequence, an amino acid analogue, a non-natural amino acid, an amino acid isomer, or combinations thereof. The ACTH peptide and one or more MSH peptides may be joined directly via a peptide bond. For example, a composition herein may comprise a γ-MSH and ACTH$_{1-24}$ linked directly by chemical linkage (e.g., a peptide bond as shown in SEQ ID NO. 15). In some cases, a composition herein may comprise a combination of an ACTH peptide and two or more MSH peptides. For example, a composition herein may comprise γ-MSH, ACTH$_{1-39}$, and β-MSH as a fusion polypeptide as shown in SEQ ID NO. 22. In some cases, γ-MSH may be a variant of γ-MSH, e.g., NDP-γ-MSH. A composition herein, in some cases, may comprise an ACTH peptide (e.g., ACTH$_{1-24}$), γ-LPH, and β-MSH. As shown in SEQ ID NO. 21, a fusion polypeptide comprising ACTH$_{1-39}$, γ-LPH, and β-MSH may be further linked to a half-life extending moiety, e.g., a glycopolymer (GCP) which can be a synthetic polymer with pendant carbohydrates, such as sugars or derivatives thereof, that can behave in a manner similar to natural glycoproteins, further described elsewhere herein. In some cases, a γ-LPH peptide may be a truncated γ-LPH or variant of γ-LPH.

A composition herein may comprise a combination of two or more ACTH peptides or variants thereof provided as a fusion polypeptide. A composition may comprise a combination of a variant of ACTH, such as NDP-ACTH$_{4-9}$ (SEQ ID NO. 31), and an ACTH peptide (e.g., ACTH$_{1-39}$, ACTH$_{1-24}$, NDP-ACTH$_{1-24}$, ACTH$_{1-17}$, ACTH$_{4-10}$, ACTH$_{4-9}$, NDP-ACTH$_{4-9}$, ACTH$_{6-9}$, and ACTH$_{11-13}$) such as provided in SEQ ID NO. 46.

As an alternative, the polypeptides may be joined by a linker to form a fusion polypeptide. The polypeptides may be joined in any order. For example, the first peptide can be joined at the N-terminal end or the C-terminal end of the polypeptide. The second peptide can be joined at the N-terminal end or the C-terminal end of the polypeptide. In some respects, each of a plurality of peptides can be independently joined or joined in tandem at the N-terminal end or the C-terminal end of the polypeptide. As used herein, the term "linker" refers to a molecule that joins at least two other molecules either covalently or non-covalently, e.g., through hydrogen bonds, ionic or van der Waals interactions, e.g., a nucleic acid molecule that hybridizes to one complementary sequence at the 5' end and to another complementary sequence at the 3' end, thus joining two non-complementary sequences. A linker connects a first polypeptide with at least a further polypeptide. The second polypeptide may be the same as the first polypeptide or it may be different. The first polypeptide and the second polypeptide can be of any suitable length. The first polypeptide and the second polypeptide may independently have a length of at least 10 amino acids and no more than 30 amino acids, at least 10 amino acids and no more than 40 amino acids, at least 10 amino acids and no more than 50 amino acids, at least 5 amino acids and no more than 30 amino acids, at least 5 amino acids and no more than 40 amino acids, at least 5 amino acids and no more than 50 amino acids, at least 3 amino acids and no more than 30 amino acids, at least 3 amino acids and no more than 40 amino acids, or at least 3 amino acids and no more than 50 amino acids.

In some embodiments, a plurality of a single type of melanocortin can be linked to one or more additional melanocortins of another type in the same fusion polypeptide. In other embodiments, a plurality of different types of melanocortin can be linked together. In certain embodiments the composition can comprise a first polypeptide comprising a fragment of a proopiomelanocortin or a variant thereof, a second polypeptide comprising a fragment of a proopiomelanocortin or a variant thereof, and one or more additional polypeptides, wherein each additional polypeptide comprises a fragment of a proopiomelanocortin or a variant thereof wherein at least one of the first polypeptide and the second polypeptide and additional polypeptides binds to a melanocortin receptor.

The first polypeptide, the second polypeptide, and the one or more additional polypeptides can independently have a length of at least 3 amino acids and no more than 30 amino acids, at least 3 amino acids and no more than 40 amino acids, at least 3 amino acids and no more than 50 amino acids, at least 5 amino acids and no more than 30 amino acids, at least 5 amino acids and no more than 40 amino acids, at least 5 amino acids and no more than 50 amino acids, at least 10 amino acids and no more than 30 amino acids, at least 10 amino acids and no more than 40 amino acids, or at least 10 amino acids and no more than 50 amino acids.

Any combination of the first polypeptide, the second polypeptide, or the at least one additional polypeptides can be covalently linked as a fusion polypeptide. Any combination of the first polypeptide, the second polypeptide, or the at least one additional polypeptides can further comprise a linker covalently linking the first polypeptide and the second polypeptide. The fusion polypeptide comprising the first polypeptide, the second polypeptide, and the at least one additional polypeptides can be an acyclic polypeptide. The fusion polypeptide comprising the first polypeptide, the second polypeptide, and the at least one additional polypeptides can be a linear polypeptide.

The fusion polypeptide comprising the first polypeptide, the second polypeptide, and, optionally, at least one additional polypeptides can have a length of at least 5 amino acids and no more than 100 amino acids, at least 5 amino acids and no more than 75 amino acids, at least 10 amino acids and no more than 75 amino acids, at least 20 amino acids and no more than 75 amino acids, at least 20 amino acids and no more than 60 amino acids, or at least 30 amino acids and no more than 60 amino acids.

Linkers can be classified into about 3 categories—flexible linkers, rigid linkers, and in vivo cleavable linkers. In addition to linking functional domains together (e.g., flexible and rigid linkers) or releasing free functional domains in vivo (e.g., cleavable linkers), linkers may offer other advantages (e.g., improving biological activity, increasing expression yield, and achieving desirable pharmacokinetic profiles). Linkers may refer to "peptide linkers", in which an amino acid sequence or peptide connects a first polypeptide with a second polypeptide, or non-peptide linkers such as chemical cross-linker. A chemical cross-linker may be a multi-functional cross-linker, e.g., a bifunctional or a trifunctional cross-linker. A cross-linker may comprise various functional groups for reactive chemistry, such as primary amines, sulfhydryls, acids, alcohols, and bromides. The peptide linker can be connected to the first polypeptide and to the second polypeptide by peptide bonds. A peptide linker may preferably be non-immunogenic to a subject, e.g., a human patient. The term "immunogenic," as used herein, generally refers to the ability of a substance, for example a therapeutic protein, to induce a response from the immune system. The immune response can be a cell or antibody mediated response. In vitro and in vivo tools can be used to identify sequences within a therapeutic protein that, when processed by T-cells, may elicit an immune response. Immunogenicity may be determined by various methods including enzyme-linked immunosorbent assays (ELISA), bridging ELISA, radioimmunoprecipitation assays (RIPA), surface plasmon resonance (SPR), and bridging electrochemiluminescence assays. A peptide linker can be of any suitable length. For example, a peptide linker may be between about 1 and 100 amino acids in length (e.g. between about 6 and 90, about 20 and 80, about 30 and 70, or about 40 and 60 amino acids in length). A peptide linker can be at least 100 amino acids in length (e.g., at least 125, 150, 175, 200, 300, 400, 500 amino acids or longer). A peptide linker can be 6-12 amino acids in length. A peptide linker can also be 9 amino acids in length. A fusion polypeptide comprising a peptide linker can be of any suitable length. A fusion polypeptide may have a length of at least 5 amino acids and no more than 100 amino acids, at least 5 amino acids and no more than 75 amino acids, at least 10 amino acids and no more than 75 amino acids, at least 20 amino acids and no more than 75 amino acids, at least 20 amino acids and no more than 60 amino acids, or at least 30 amino acids and no more than 60 amino acids.

A flexible linker, e.g., a flexible peptide linker, may be used to join domains requiring a certain degree of movement or interaction. For example, a peptide linker may comprise predominantly glycine (G) and serine (S) amino acids, e.g., $(GGS)_n$, $(GGGS)_n$ (SEQ ID NO. 89), $(GGGGS)_n$ (SEQ ID NO. 90), or $(GSG)_n$ where n represents any suitable number of repeats. In some embodiments, the number of repeats (e.g., the value of n) can be 1, 2, 3, 4, 5, 6, 7, 8, 9, or 10. Thus, in some embodiments, the linker can be 3 amino acids to 50 amino acids. Glycine and serine are relatively small, non-polar amino acids that have shown little interaction with linked proteins and can lack secondary structure, thereby having minimal or no effect on the structure and the function of the linked proteins. For example, a composition herein may comprise a glycine and serine based linker having an amino acid sequence $(GGS)_n$ wherein n is any suitable number of repeats. A composition herein may also comprise a glycine and serine based linker having an amino acid sequence $(GGGGS)_n$ (SEQ ID NO. 90) wherein n is any suitable number of repeats. A composition herein may comprise an α-MSH peptide, or a variant thereof (e.g., NDP-α-MSH), and an $ACTH_{1-24}$ peptide, or variant thereof (e.g., NDP-$ACTH_{1-24}$), linked by a glycine and serine based linker, such as shown in SEQ ID NO. 23. In some cases, the linkage order of the α-MSH peptide, or a variant thereof (e.g., NDP-α-MSH), and the $ACTH_{1-24}$ peptide is reversed as shown in SEQ ID NO. 26.

In some cases, rigid linkers may be preferred to provide desired orientations and separation of the linked domains, maintaining the independent functions of each peptide. Rigid linkers may form secondary structure, e.g., alpha helices. For example, a linker comprising primarily proline residues or the sequence (EAAAK) (SEQ ID NO. 91), where n represents any suitable number of repeats, may be used to provide a more rigid linker compared to glycine and serine based linkers.

In some cases, linkers of intermediate flexibility may be preferred (e.g., having flexibility between that of Gly/Ser-based linkers and Proline-based linkers). To decrease conformational mobility of a spacer, more rigid amide linkages can be built by alternating β and α amino acids. For example, a linker comprising βAla-Gly-βAla can provide intermediate flexibility. A composition herein may comprise two or more ACTH peptides or variants thereof (e.g. $ACTH_{1-39}$, $ACTH_{1-24}$, NDP-$ACTH_{1-24}$, $ACTH_{1-17}$, $ACTH_{4-10}$, $ACTH_{4-9}$, NDP-$ACTH_{4-9}$, $ACTH_{6-9}$, and $ACTH_{11-13}$) linked by one or more linkers (e.g., flexible, rigid, and/or cleavable linkers), such as shown in SEQ ID NO. 44, SEQ ID NO. 45, SEQ ID NO. 66, SEQ ID NO. 67, SEQ ID NO. 68, SEQ ID NO. 69, SEQ ID NO. 70, SEQ ID NO. 71, and SEQ ID NO. 72.

In some cases, a cleavable linker may be preferred to release the functional domains in vivo. The in vivo cleavage of the linkers in fusion polypeptides may be carried out by proteases that are expressed in vivo under normal and pathological conditions (e.g., cancer or inflammation), in specific cells or tissues, or constrained within certain cellular compartments. In some cases, cleavage may occur when the fusion polypeptide reaches the target area of interest. In some cases, cleavage may occur after the fusion polypeptide is administered, e.g., to a patient or subject. For example, cleavage may occur upon administration. Cleavage, in some cases, may occur at least 1 minute after administration (e.g., at least 20 minutes, 30 minutes, 45 minutes, 1 hour, 2 hours, 3 hours, 4 hours or longer).

In some cases, a peptide linker may comprise an endogenous sequence, or a sequence that is naturally occurring. A peptide linker may be a sequence naturally found in a POMC precursor polypeptide. For example, a composition comprising ACTH, or variant thereof, and γ-MSH, or variant thereof, can be provided as a fusion polypeptide with a peptide linker having the amino acid sequence naturally found in POMC, e.g., SEQ ID NO. 2. In some cases, the composition comprises γ-MSH linked to α-MSH via a natural linker as shown in SEQ ID NO. 5. A composition herein may comprise an ACTH peptide or variant thereof ($ACTH_{1-39}$, $ACTH_{1-24}$, NDP-$ACTH_{1-24}$, $ACTH_{1-17}$, $ACTH_{4-10}$, $ACTH_{4-9}$, NDP-$ACTH_{4-9}$, $ACTH_{6-9}$, and $ACTH_{11-13}$) linked to an MSH peptide (e.g., α-MSH, β-MSH, or γ-MSH) or variant thereof (e.g. NDP-α-MSH or NDP-γ-MSH), by a linker comprising an amino acid sequence naturally found in POMC as shown in SEQ ID NO. 39, SEQ ID NO. 40, SEQ ID NO. 42, and SEQ ID NO. 43. The naturally occurring linker sequence contains a cleavage site that can be recognized. The cleavage site in the linker may allow the fusion polypeptide to be cleaved by endogenous proteases, e.g., serine proteases, cysteine proteases, aspartate proteases, threonine proteases, glutamic acid proteases, metalloproteinases, asparagine lyases, etc, after administration to a subject. For example, the linker may comprise a cleavage site recognized by thrombin, furin, proconvertase 1, matrix metalloproteinase-6 (MMP6), caspase 3, plasmin, cathepsin B, cathepsin G, cathepsin L, elastase-2, neprilysin, trypsin, chymotrypsin or calpain. The naturally occurring linker sequence may have an amino acid sequence that may be recognized by a proconvertase, e.g., KR, RRKR (SEQ ID NO. 73), KKRR (SEQ ID NO. 74), GGGGSGGGGS (SEQ ID NO. 80), GGGS (SEQ ID NO. 92), GGGGSGG (SEQ ID NO. 93), RRNSSSGSSGAGQKR (SEQ ID NO. 75), SRSRRSAGS (SEQ ID NO. 77), ERSKRAVGS (SEQ ID NO. 78), ERLKRAAGS (SEQ ID NO. 79), or ERLKRAVGS (SEQ ID NO. 76). The naturally occurring linker sequence may have an amino acid sequence that may be recognized by a matrix metalloproteinase, e.g., PLGLWA (SEQ ID NO. 81), PQALVA (SEQ ID NO. 82), PANLVG (SEQ ID NO. 83), PAELIG (SEQ ID NO. 84), PANLVA (SEQ ID NO. 85), PAGLVG (SEQ ID NO. 86), and PAGLVA (SEQ ID NO. 87).

For example, a composition herein may comprise a fusion polypeptide of γ-MSH and $ACTH_{1-24}$ joined by a linker sequence comprising KR as shown in SEQ ID NO. 1, γ-MSH and $ACTH_{1-39}$ joined by a linker sequence comprising KR as shown in SEQ ID NO. 13, or γ-MSH and α-MSH joined by a linker sequence comprising KR as shown in SEQ ID NO. 4. In some cases, the γ-MSH is the variant NDP-γ-MSH and the fusion polypeptide comprises NDP-γ-MSH and $ACTH_{1-24}$ joined by a linker sequence comprising KR as shown in SEQ ID NO. 3 or NDP-γ-MSH and α-MSH joined by a linker sequence comprising KR as shown in SEQ ID NO. 6. Alternatively, the fusion polypeptide may comprise the α-MSH variant NDP-α-MSH and have a sequence as shown in SEQ ID NO. 7. In some cases, the fusion polypeptide may comprise both an α-MSH variant, such as NDP-α-MSH, and a γ-MSH variant, such as NDP-γ-MSH. Such a fusion polypeptide may have an amino acid sequence as shown in SEQ ID NO. 8.

Compositions disclosed herein may comprise a linker sequence containing a cleavage site that is recognized by a protease, e.g., a prohormone convertase. A linker sequence may contain a cleavage site that is recognized by a member of the subtilisin/kexin-like proprotein convertases, such as proprotein convertase 1 (PC1) and proprotein convertase 2 (PC2), which are involved in processing of POMC. The linker may alternatively contain a cleavage site that is recognized by other members of the subtilisin/kexin-like proprotein convertase family, such as the proconvertases furin, paired basic amino acid cleaving enzyme 4 (PACE4), PC4, PC5/6 and PC7.

A linker sequence may contain a cleavage site, in some cases, that is recognized by matrix-metalloproteinases (MMPs). MMPs, also referred to as matrixins, are a family of approximately 24 human zinc-containing endopeptidases that are capable of degrading components of the ECM and many other proteins. MMPs have been associated with various pathologies, including various types of arthritis, such as gout, juvenile rheumatoid arthritis, rheumatoid arthritis, psoriatic arthritis, and osteoarthritis; inflammation and autoimmunity; cancer metastasis and tumor invasion; angiogenesis and neovascularization; cardiovascular disease such as atherosclerotic plaques; cerebrovascular disease such as blood-brain barrier breakdown following focal cerebral stroke and cerebral aneurysms; pulmonary disease such as bronchial asthma, pulmonary emphysema, and chronic bronchitis; ocular disease such as age-related macular degeneration, proliferative diabetic retinopathy, retinopathy of prematurity, glaucomatous optic nerve head damage, vitreal liquefaction and vitreoretinopathy; gastrointestinal diseases such as Crohn's disease or mucositis (e.g., gastrointestinal mucositis); hepatic diseases such as hepatitis, renal diseases such as glomerulonephritis, pancreatitis, vasculitis, retinal vasculitis, skin conditions such as psoriasis and dermatitis, and oral diseases (e.g., an oral condition) such as periodontitis, gingivitis, oral mucositis and oral cancer. MMPs are overexpressed in a variety of pathological conditions, e.g., arthritic diseases, cancer, and inflammation. Compositions comprising a MMP cleavable linker can be used, for example, if cleavage is desired at sites of cancer and/or inflammation to treat any of the aforementioned pathologies.

A composition herein, in some cases, may comprise a linker having a site recognized by a proprotein convertase such as furin, paired basic amino acid cleaving enzyme 4 (PACE4), PC4, PC5/6 and PC7. A composition herein may comprise an α-MSH peptide, or variant thereof (e.g., NDP-α-MSH) linked to an ACTH peptide, or variant thereof, by a linker comprising a cleavage site recognized by Furin as shown in SEQ ID NO. 24 and SEQ ID NO. 27. A composition herein may comprise an ACTH peptide or variant thereof (e.g. $ACTH_{1-39}$, $ACTH_{1-24}$, NDP-$ACTH_{1-24}$, $ACTH_{1-17}$, $ACTH_{4-10}$, $ACTH_{4-9}$, NDP-$ACTH_{4-9}$, $ACTH_{6-9}$, and $ACTH_{11-13}$) linked to an MSH peptide (e.g., α-MSH, β-MSH, or γ-MSH) or variant thereof (e.g. NDP-α-MSH or NDP-γ-MSH) by a linker comprising a cleavage site recognized by a proconvertase as shown in SEQ ID NO. 38 and SEQ ID NO. 41. As an alternative, a composition herein, may comprise a linker having a site recognized by an MMP. A composition herein may comprise an α-MSH peptide, or variant thereof (e.g., NDP-α-MSH) linked to an ACTH peptide, or variant thereof, by a linker comprising a cleavage site recognized by an MMP (e.g., PLGLWA (SEQ ID NO. 81)) as shown in SEQ ID NO. 25 and SEQ ID NO. 28. A composition herein may comprise an ACTH peptide (e.g. $ACTH_{1-39}$, $ACTH_{1-24}$, $ACTH_{1-17}$, $ACTH_{4-10}$, $ACTH_{4-9}$, $ACTH_{6-9}$, and $ACTH_{11-13}$) or variant thereof linked to an MSH peptide (e.g., α-MSH, β-MSH, or γ-MSH) or variant thereof (e.g. NDP-α-MSH or NDP-γ-MSH) by a linker comprising a cleavage site recognized by an MMP (e.g., PAGLVA (SEQ ID NO. 87)) as shown in SEQ ID NO. 29 and SEQ ID NO. 32.

In some cases, the linker may not contain a cleavable site. For example, a composition herein may comprise γ-MSH linked to $ACTH_{1-24}$ via a linker without a cleavable site as shown in SEQ ID NO. 14.

A composition herein may comprise a combination of a mutated ACTH peptide and one or more MSH peptides (e.g., α-MSH, β-MSH, and γ-MSH) or variant thereof (e.g., NDP-α-MSH or NDP-γ-MSH), provided as a fusion polypeptide. A mutated ACTH peptide (e.g., SEQ ID NO. 48, SEQ ID NO. 49, and SEQ ID NO. 50) having decreased ability to activate MCR2 may potentially result in decreased steroidogenesis relative to ACTH. A composition herein may comprise a combination of a mutated ACTH peptide and one or more MSH peptides (e.g., α-MSH, β-MSH, and γ-MSH) or variant thereof (e.g., NDP-α-MSH or NDP-γ-MSH), for example such as provided in any one of SEQ ID NOS. 52-54, SEQ ID NOS. 56-58, SEQ ID NOS. 60-65. The ability of a mutated ACTH peptide to decrease MCR2 activation can be assessed by comparing MCR2 activation of compositions comprising mutated ACTH peptide to compositions comprising un-mutated ACTH peptide, such as those provided in SEQ ID NO. 51, SEQ ID NO. 55, and SEQ ID NO. 59.

In various aspects of the present disclosure, peptides having SEQ ID NO. 1-SEQ ID NO. 72 have reduced steroidogenesis relative to ACTH.

The present disclosure provides methods of treating inflammation comprising administering compositions disclosed herein to a subject or patient in need thereof. The administration of compositions disclosed herein may treat inflammation. Administering compositions disclosed herein may reduce inflammation by modulating cytokine and chemokine levels, e.g., increasing the production of anti-inflammatory cytokines, decreasing the production of pro-inflammatory cytokines and chemokines, and/or modulating expression of adhesion molecules, such as vascular cell adhesion molecule-1 (VCAM-1) intercellular adhesion molecule-1 (ICAM-1) and E-selectin. Cytokines are commonly classified as either anti-inflammatory or pro-inflammatory, although some cytokines may act as both pro- and anti-inflammatory cytokines. For example, interleukin-1β (IL-1β), tumor necrosis factor-α (TNF-α), γ-interferon (IFN-γ), IL-2, IL-6, IL-8, IL-12, IL-17, IL-18, IL-23 and granulocyte-macrophage colony stimulating factor (GM-CSF) are generally characterized as pro-inflammatory cytokines. IL-4, IL-10, IL-13, IFN-α, and transforming growth factor-β (TGF-β), which is derived from a latent TGF-β complex comprising latent TGF-β binding protein (LTBP) and latency-associated peptide (LAP), are generally recognized as anti-inflammatory cytokines. Chemokines such as MIP1α, MIP-1β, MCP-1, IL-8 and KC contribute to the inflammatory process by recruiting white bloods cells to the site of inflammation. Expression of the many of these pro-inflammatory cytokines and chemokines is regulated by the transcription factor NF-kB. NF-kB, in addition, stimulates inflammatory mediator production, monocytes, nitric oxide production, heme oxygenase (HO) expression, superoxide dismutase, expression of costimulatory factors, etc. Administration of the compositions described herein can decrease inflammation by inhibiting NF-kB activation. In addition to shifting macrophages from a pro-inflammatory M1 phenotype to an anti-inflammatory/immunosuppressive M2 phenotype, administration of the compositions described herein can cause macrophages to phagocytose neutrophils. This is known as efferocytosis and is critical as to how melanocortins cause resolution of inflammation. Thus, the compositions described herein can contribute to pro-resolution of inflammation (e.g., not solely to inhibition of inflammation).

The compositions herein may also reduce inflammation by reducing white blood cell numbers and functions, e.g. neutrophil counts and migration to sites of inflammation. Neutrophils may have various roles in inflammation and immunity. Neutrophils have been proposed to participate in protection against extracellular pathogens as well as intracellular pathogens such as viruses and mycobacteria. They have been shown to shape the adaptive immune response at various levels, including marginal zone B cells, plasmacytoid dendritic cells and T cell populations, and even to control NK cell homeostasis. Neutrophils have been shown to mediate an alternative pathway of systemic anaphylaxis and to participate in allergic skin reactions. Activated neutrophils at or near sites of inflammation can secrete a variety of pro-inflammatory cytokines, thereby modulating an inflammatory response. Neutrophils are especially important in inflammatory disorders, such as gout and other types of arthritis, because they secrete a variety of molecules that cause tissue damage and destruction to joins and other tissues. The compositions herein can modulate neutrophil migration to sites of inflammation, for example by modulating levels of neutrophil chemo-attractants such as keratinocyte-derived chemokine (KC).

The compositions disclosed herein may also be neuroprotective. For example, the compositions disclosed herein can be neuroprotective for neurons, oligodendrocytes, astrocytes, or oligodendrocyte precursor cells.

In some aspects, the compositions disclosed herein may be useful in treating osteoporosis. For example, the compositions disclosed herein can stimulate osteoblasts and/or inhibit osteoclasts.

Clinical Indications

Treatment of Inflammatory Conditions and Immune Disorders

The compositions and methods disclosed herein can be used for various medical applications As used herein, the term "patient" or "subject" generally refers to any animal, such as human and non-human primates, animal test subjects including, but not limited to, laboratory mice, rats, rabbits, cats, dogs, pigs, sheep, cows, and horses having a condition that may be treated by administering the compositions or applying the methods disclosed herein.

The terms "inflammatory disease" or "inflammatory condition" refer to a disease or condition characterized in part by inflammatory mechanisms, such as specific T lymphocyte reactions or antibody-antigen interactions causing the recruitment of inflammatory cells, changes in the activity or number of other white blood cells, such as neutrophils and monocytes, alterations in the expression level of endogenous mediator chemicals, e.g., increased NF-κB activity, increased TNF-α production, increased IL-1 production and increased IL-6 production as well as other inflammatory cytokines and chemokines such as IL-8 and MIP-alpha.

The compositions and methods disclosed herein may be used to treat or prophylactically treat inflammatory diseases, disorders, and conditions in a subject. An inflammatory condition may result from any disease or disorder, such as, but not limited to, solar urticaria, xeroderma pigmentosa, diabetic retinopathy, retinopathy of prematurity, uveitis, gingivitis, mucositis, peritonitis, pleuritis, endometriosis, peripheral vascular disease, arthritic conditions such as osteoarthritis, juvenile rheumatoid arthritis, rheumatoid arthritis, septic arthritis, psoriatic arthritis, acute gout, gout and pseudogout, juvenile idiopathic arthritis, Still's disease and ankylo sing spondylitis, as well as arthritis secondary to other diseases, such as arthritis secondary to lupus erythematosus, Henoch-Schönlein purpura, psoriasis, reactive arthritis, haemochromatosis, hepatitis including toxic hepatitis, Wegener's granulomatosis, vasculitis syndromes, Lyme disease, familial Mediterranean fever, hyperimmunoglobulinemia D with recurrent fever, TNF receptor-associated periodic syndrome and inflammatory bowel disease, including Crohn's disease and ulcerative colitis. In addition, inflammation conditions can result from joint damage due to sickle cell anemia and bleeding into the joint associated with hemophilia.

An inflammatory condition may result from inflammatory bowel disease, such as Crohn's disease, eosinophilic esophagitis, ulcerative colitis, collagenous colitis, lymphocytic colitis, ischemic colitis, diversion colitis, Behçet's syndrome, infective colitis and indeterminate colitis.

An inflammatory condition may result from an autoimmune disease, including, but not limited to, systemic syndromes such as systemic lupus erythematosus, Sjögren's syndrome, scleroderma, juvenile rheumatoid arthritis, rheumatoid arthritis, psoriatic arthritis, polymyositis, and dermatomyositis. An autoimmune disease may also be a local condition affecting biological subsystems such as the endocrine system (e.g., diabetes mellitus type 1, Hashimoto's thyroiditis, and Addison's disease); the dermatologic system (e.g., pemphigus vulgaris); the hematologic system (e.g., autoimmune hemolytic anemia); the renal system (e.g., nephrotic syndrome and nephritis such as glomerulonephritis and interstitial nephritis); and the neural system (e.g., multiple sclerosis). Additional, non-limiting examples of autoimmune diseases and autoimmune disease related disorders include acute disseminated encephalomyelitis, ankylosing spondylitis, antiphospholipid antibody syndrome, aplastic anemia, autoimmune hepatitis, toxic hepatitis, autoimmune oophoritis, autoimmune thrombocytopenia, autoimmune hemolytic anemia, drug-induced antibodies, drug reactions from administration of biologics, celiac disease, Crohn's disease, gestational pemphigoid, Goodpasture's syndrome, Graves' disease, Guillain-Barré syndrome, Hashimoto's disease, idiopathic thrombocytopenic purpura, irritable bowel disease (IBD), Kawasaki disease, lupus erythematosus, mixed connective tissue disease, multiple sclerosis, myasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, autoimmune hemolytic anemia, Wegener's granulomatosis, spasms, infantile spasms, and epilepsy.

An inflammatory condition may result from a skin condition, such as contact dermatitis, atopic dermatitis, Stevens-Johnson syndrome, burns, and acne.

An inflammatory condition may result from pancreatitis, which can be caused by gallstones, mumps, tumors, pain medication, antibiotics, or from alcohol use.

An inflammatory condition may result from vasculitis, Behcet's Disease, Buerger's disease (thromboangiitis obliterans), eosinophilic granulomatosis with polyangiitis (EGPA or Churg Strauss Syndrome), cryoglobulinemia, giant cell arteritis (or temporal arteritis), Henoch-Schonlein purpura (or IgA vasculitis), microscopic polyangiitis, polyarteritis *nodosa*, polymyalgia rheumatic, rheumatoid vasculitis, Takayasu's arteritis, hypersensitivity vasculitis, Kawasaki disease, isolated aortitis, urticarial vasculitis, retinal vasculitis, and granulomatosis with polyangiitis (GPA or Wegener's granulomatosis).

The inflammation can be associated with an acute inflammatory condition. Non-limiting examples of acute inflammatory conditions include acute flares of inflammatory arthritis, including RA, lupus and other autoimmune diseases, MS flares; acute attacks of gout; acute attacks of asthma; severe acute allergic reactions such as anaphylaxis and shock; acute injuries to tissues such as the skin (e.g., burns, dermatitis, and phototoxic skin reactions), brain (e.g., stroke) or heart (e.g., myocardial infarction), liver, kidney, lungs, and pancreas (e.g., pancreatitis), gastrointestinal tract including esophagus, stomach, intestine (small and large), rectum, all of which could be due to toxic injury, ischemia/infarction, inflammation, or trauma; shock due to hypovolemia, sepsis, or toxic shock syndrome; acute respiratory distress syndrome; vaccine reaction; and cytokine storm secondary to immunotherapy for cancer or other causes.

An inflammatory reaction may result from an immune response to a foreign molecule or cell introduced into the body. This could be a drug such as an anti-hemophilic factor being administered to treat a medical condition. These include proteins, monoclonal antibodies, peptides, polypeptides, and cells. Examples include reactions to monoclonal antibodies, such as rituximab; anti-hemophilic factors, such as Factors VII, VIII, IX, and X; and other proteins, such as interferons including alpha, beta, and gamma. An inflammatory reaction may also be in response to a vaccine.

An inflammatory condition may result from a chronic obstructive pulmonary disease (COPD), also known as chronic obstructive airway diseases. These can include diseases characterized by the pathological limitation of airflow in the airway that is not fully reversible, for example chronic bronchitis, emphysema, pneumoconiosis, pulmonary neoplasms and other lung disorders. Other inflammatory conditions may include upper or lower airway diseases and disorders, such as allergic asthma, eosinophilic pneumonia, alpha-1 anti-trypsin deficiency, allergic rhinitis, vasomotor rhinitis, allergic conjunctivitis, non-allergic conjunctivitis, Wegener's granulomatosis, and sarcoidosis; and airway diseases related to external toxins or substances including various forms of pneumoconiosis (coal worker's pneumoconiosis, asbestosis, silicosis, bauxite fibrosis, berylliosis, or siderosis), byssinosis or hypersensitivity pneumonitis (farmer's lung or bird fancier's lung). Other lung diseases involving an inflammatory condition include acute respiratory distress syndrome.

The inflammatory condition may result from a transplant-related condition or syndrome, such as graft-versus-host disease, hyper-acute rejection, acute rejection, or chronic rejection. Graft-versus-host disease (GVHD) is a common complication of allogeneic bone marrow transplantation, but can occur with other transplantations, particularly those with T-cells present in the graft, either as contaminants or intentionally introduced. GVHD may be characterized as acute or chronic. Hyper-acute, acute or chronic rejection can occur with bodily organs such as kidneys, liver, pancreas, spleen, uterus, heart or lungs, as well as transplantation of bone, cornea, face, hand, penis or skin.

The inflammatory condition may result from a muscular dystrophy, which refers to diseases associated with muscle and the musculoskeletal system. Inflammation can be associated with muscular dystrophies such as Duchenne Muscular Dystrophy and Becker's Muscular Dystrophy. An inflammatory condition may result from sarcopenia, for example sarcopenia due to aging or chronic disease, e.g., cachexia. Inflammation may result from muscle injury.

The inflammatory condition may result from cystic fibrosis, which a hereditary disease associated with a mutation in the gene cystic fibrosis transmembrane conductance regulator.

The inflammatory condition may result from a nervous system condition, such as a central nervous system condition. Non-limiting examples of inflammatory conditions affecting the nervous system include the various types of multiple sclerosis (e.g., relapse-remitting, secondary progressive, primary progressive, and progressive-relapsing); various types of Alzheimer's disease; Parkinson's disease; spinal muscular atrophy; various types of encephalitis and meningitis (e.g., primary encephalitis, secondary encephalitis, bacterial meningitis, viral meningitis, parasitic meningitis, fungal meningitis, and non-infectious meningitis); acute disseminated encephalomyelitis; acute transverse myelitis; neuromyelitis optica; focal demyelinating syndromes (e.g., Balo's concentric sclerosis and Marburg variant of MS); amyotrophic lateral sclerosis; progressive multifocal leukoencephalopathy; subacute sclerosing panencephalitis; acute haemorrhagic leucoencephalitis (Hurst's disease); human T-lymphotropic virus type-1-associated myelopathy/tropical spactic paraparesis; Devic's disease; human immunodeficiency virus encephalopathy; human immunodeficiency virus vacuolar myelopathy; peipheral neuropathies; Guillanin-Barre Syndrome and other immune mediated neuropathies; and myasthenia gravis.

A neural inflammatory condition may be associated with a cerebrovascular accident or a peripheral nerve disorder, such as peripheral neuropathy, autonomic neuropathy, mononeuropathy, sciatica, carpal tunnel syndrome, polyneuropathy, diabetic neuropathy, postherpetic neuralgia, and thoracic outlet syndrome.

The inflammatory condition may result from trauma, such as injury to tissues and organs, including bone, muscle, heart, kidney, spleen, lung, liver, brain, thyroid, bladder, gall bladder, diaphragm, stomach, pancreas, intestine, breast, and rectum.

The inflammatory condition may result from adhesions, including visceral, peritoneal, and pleural, from surgery, trauma or other injuries as well as inflammatory disorders.

The inflammatory condition may result from a skeletal disorder, which comprises a group of heterogeneous diseases affecting cells and tissues of bone, bone marrow, cartilage, tendons, and ligaments. A skeletal disorder may include genetic disorders characterized by abnormal bone metabolism or resorption. Non-limiting examples of skeletal disorders and conditions include osteoporosis (e.g., post-menopausal osteoporosis, glucocorticoid induced osteoporosis, hyperthyroidism-induced osteoporosis, immobilization-induced osteoporosis, heparin-induced osteoporosis and immunosuppressive-induced osteoporosis as well as long term complications of osteoporosis such as curvature of the spine, loss of height and prosthetic surgery), abnormally increased bone turnover, hyper-calcemia including humoral hypercalcemia, hyperparathyroidism, Paget's bone diseases, osteolysis including periprosthetic osteolysis, hypercalcemia of malignancy with or without bone metastases, hypercalcemia of fracture healing, juvenile rheumatoid arthritis, rheumatoid arthritis, osteoarthritis, ostealgia, osteopenia, calculosis, lithiasis including urolithiasis, gout and ankylosing spondylitis, tendonitis, bursitis, malignant bone tumor e.g. osteosarcoma, osteogenesis imperfecta, metastatic bone disease, alveolar bone loss, post-osteomy and childhood idiopathic bone loss.

The inflammatory condition may result from a spinal condition, such as cervical disk rupture, degenerative disc disease, lumbar disc disease, compression fracture, spinal stenosis, myelopathy, lumbar scoliosis, kyphosis, spondylolisthesis, anklylosing spondylitis, and retrolisthesis.

An inflammatory condition may result from immunodeficiencies, including common variable immunodeficiency, selective immunoglobulin deficiency, IgA deficiency, transient hypogammaglobulinemia of infancy, X-linked agammaglobulinemia, chronic mucocutaneous candidiasis, DiGeorge syndrome, X-linked lymphoproliferative syndrome, Ataxia-telangiectasia, hyperimmunoglobulinemia E syndrome, severe combined immunodeficiency, Wiskott-Aldrich syndrome, chronic granulomatous disease, Chediak-Higashi syndrome, cyclic neutropenia, leuckocyte adhesion defects, complement component 1 (C1) inhibitor deficiency (hereditary angioedema), complement component 3 (C3) deficiency, complement component 4 (C4) deficiency, complement component 5 (C5) deficiency, complement component 6 (C6) deficiency, complement component 7 (C7) deficiency, complement component 8 (C8) deficiency, or complement component 9 (C9) deficiency. An inflammatory condition may result from immunodeficiencies that are iatrogenic, such as treatment with corticosteroids, immunosuppressive drugs such as cyclosporine, methotrexate, cytotoxic agents such as cyclophosphamide, and radiation.

Melanocortins can affect an immune response. In some aspects, melanocortins may upregulate regulatory T cell phenotypes (which can include expression of CTLA-4, GITR, LAG-3, CD127, Foxp3, CD25, and/or CD4) and/or production of cells with a regulatory T cell (e.g., Treg) phenotype and/or downregulate Th17, Th2, Th1, and/or T follicular cells.

Accordingly, the compositions and methods disclosed herein may be used to treat immune disorders and conditions and to modulate immune response.

Treatment of Fibrotic and Sclerotic Conditions

Compositions and methods disclosed herein may be used to treat or prophylactically treat fibrotic and sclerotic conditions. Fibrotic and sclerotic diseases may involve an inflammatory response and, in some instances, can be considered an inflammatory condition. Fibrotic and sclerotic conditions may be idiopathic, toxic, hereditary and/or pharmacologically-induced disorders. Fibrotic disorders can generally be characterized by excessive production of extracellular matrix, primarily type I collagen, which may result in loss of organ function. Non-limiting examples of fibrotic and sclerotic conditions that may be treated by the compositions and methods herein include localized scleroderma, systemic sclerosis, sclerodermic graft-versus-host disease of the skin, idiopathic lung fibrosis, idiopathic pulmonary fibrosis, bleomycin-induced lung fibrosis, cyclosporine-induced nephropathy, renal failure, cirrhosis of the liver, hypertrophic scars, adhesions, cardiac fibrosis and keloids.

Treatment of Dermatologic Conditions

Compositions and methods disclosed herein may be used to treat or prophylactically treat dermatologic conditions. Non-limiting examples of dermatologic conditions include acne vulgaris (commonly referred to as acne), cystic acne, folliculitis, dermatitis, contact dermatitis, atopic dermatitis (commonly referred to as atopic eczema or eczema), polymorphous light eruption, psoriasis, rosacea, seborrheic dermatitis, vitiligo, porphyria, porphyria cutanea tarda, erythropoietic protoporphyria, solar urticaria, urticaria pigmentosa, xeroderma pigmentosum, pemphigus, pemphigoid, erysipelas, lichen planus, alopecia areata, mycosis fungoides, Stevens-Johnson syndrome, insect bites, burns, cat scratch fever, discoid lupus, cutaneous non-Hodgkin's lymphoma, dermatomyositis, erythema multiforme, and herpes zoster.

Treatment of Ocular Conditions

Compositions and methods disclosed herein may be used to treat or prophylactically treat ocular conditions. Various ocular conditions may also be characterized by inflammation. Examples of ocular conditions include dry eye disease, uveitis, diabetic retinopathy, retinopathy of prematurity, macular degeneration, and retinitis pigmentosa. Symptoms of dry eye include keratitis, conjunctival and corneal staining, redness, blurry vision, decreased tear film break-up time, decreased tear production, tear volume, and tear flow, increased conjunctival redness, excess debris in the tear film, ocular dryness, ocular grittiness, ocular burning, foreign body sensation in the eye, excess tearing, photophobia, ocular stinging, refractive impairment, ocular sensitivity, and ocular irritation such as itching. Uveitis is an ocular disease involving inflammation of the middle layer or uvea of the eye. Uveitis may be associated with any inflammatory process involving the interior of the eye, including inflammation of the iris and anterior chamber. Uveitis includes anterior, intermediate, posterior and panuveitic forms. Uveitis may be associated with red eye, injected conjunctiva, pain and decreased vision, dilated ciliary vessels, presence of cells and flare in the anterior chamber, keratic precipitates on the posterior surface of the cornea, the presence of inflammatory cells in the vitreous cavity, and inflammation of the retina and choroid. Uveitis may be secondary to any of a number of diseases and disorders, including acute posterior multifocal placoid pigment epitheliopathy, ankylo sing spondylitis, Behçet's disease, birdshot retinochoroidopathy, brucellosis, herpes simplex, herpes zoster, inflammatory bowel disease, juvenile rheumatoid arthritis, Kawasaki disease, leptospirosis, Lyme disease, multiple sclerosis, psoriatic arthritis, Reiter's syndrome, sarcoidosis, syphilis, systemic lupus erythematosus, toxocariasis, toxoplasmosis, tuberculosis, Vogt-Koyanagi-Harada syndrome, Whipple disease and polyarteritis nodosa. In certain aspects, compositions and methods disclosed herein can be used to treat diabetic retinopathy.

Treatment of Ischemic Conditions and Reperfusion Injury

Ischemia generally refers to any decrease or stoppage in the blood supply to any bodily organ, tissue, or cell. Examples include myocardial ischemia and infarction, cerebrovascular ischemia, or infarction manifested as transient ischemic attacks (TIAs) or stroke, peripheral vascular disease, and mesenteric ischemia. Ischemia may result in ischemic damage to the bodily organ, tissue, or cell. Ischemia can result from a constriction or obstruction of the vasculature, or may result from a shock condition such as septic shock or circulatory shock, such as hemorrhagic shock and hypovolemic shock. The decrease or lack of blood flow results in a decrease or lack of oxygen to the affected part of the body, and may also result in an increase of inflammation mediating molecules such as various cytokines.

Ischemia may also result from any of a variety of diseases or conditions including vasculitis, peripheral vascular diseases, atherosclerotic diseases such as atheromata with thrombosis, embolism from the heart or from blood vessel from any organ, vasospasm, hypotension due to heart disease, hypotension due to systemic disease including infection or allergic reactions, or hypotension resulting from administration, ingestion or other exposure to one or more toxic compounds or drugs. Ischemia may also be secondary ischemia, which is ischemia secondary to a disease or condition such as diabetes mellitus, hyperlipidemia, hyperlipoproteinemia, dyslipidemia Buerger's disease, also called thromboangiitis obliterans, Takayasu's arteritis, arteritis temporalis, Kawasaki disease, also called lymph node syndrome, mucocutaneous node disease, infantile polyarteritis, retinal vasculitis, cardiovascular syphilis, and various connective tissue diseases and disorders.

Ischemia-reperfusion generally refers to the interruption of blood flow to bodily tissue and the subsequent and often abrupt restoration of blood flow to the tissue. While restoration of blood flow following ischemia is essential to preserve functional tissue, the reperfusion itself can be harmful to the tissue. For example, in certain surgical procedures such as cardiac surgery and organ transplantation, the flow of blood is stopped temporarily and then resumed (reperfusion), which can result in ischemia-reperfusion injury. Similarly, during a heart attack, the blood that supplies the heart is stopped, potentially resulting in ischemia that may evolve into infarction. Current treatment to relieve heart attacks requires reperfusion of the ischemic area of the heart, such as by using thrombolytic drugs or coronary angioplasty. Both ischemia and reperfusion are known to be important contributors to tissue necrosis. Several mechanisms appear to play a causative role in the generation of tissue damage associated with ischemia-reperfusion injury.

Various methods of limiting reperfusion injury have been described, such as induced hypothermia, controlled reperfusion, and ischemic preconditioning. Induced hypothermia is the induction of moderate hypothermia, thought to suppress many of the chemical reactions associated with reperfusion injury. Controlled reperfusion refers to controlling the initial period of reperfusion by reperfusing the tissue at a low pressure using blood that has been modified to be hyperosmolar, alkalotic, and substrate-enriched. Ischemic preconditioning is the purposeful induction of short ischemic events to generate a protective effect by slowing cell metabolism during a longer ischemic event. Although these treatments may be useful in surgical settings (e.g., before or after planned heart surgery), they may not be possible in emergency settings.

Compositions disclosed herein may be utilized for perfusion of a transplant organ, which perfusion may be prior to, during or subsequent to transplant of the organ. Administering compositions disclosed herein may prevent or limit the severity of reperfusion injury including renal reperfusion injury, lung injury secondary to renal reperfusion, reperfusion heart injuries subsequent to a myocardial infarction, reperfusion brain injuries subsequent to a cardiovascular injury, myocardial infarction, and stroke.

Treatment of Shock

Compositions and methods disclosed herein may be employed for the treatment of shock such as septic shock or circulatory shock in a subject.

The term "septic shock," as used herein, refers to a medical condition that occurs when sepsis, which is organ injury or damage in response to infection, leads to low blood pressure and abnormalities in cellular metabolism.

The term "circulatory shock," as used herein, refers to a medical condition in which organs and/or tissues of the body of the subject do not receive adequate flow of blood. Circulatory shock includes conditions such as hypovolemic shock, cardiogenic shock, vasodilatory shock, etc. These conditions or dysfunctions in circulation can in turn have different causes, such as bacterial blood infection (septic shock or infectious), severe allergic reaction (anaphylactic shock), trauma (traumatic shock), severe bleeding or loss of blood (hemorrhagic shock), neurologic dysfunction causing abnormal opening of blood vessels (neurogenic shock) or endocrine related (endocrine shock). Circulatory shock can further result in ischemia and ischemic damage to bodily organs, tissues, cells or parts. Upon reperfusion, or restoration of blood flow, ischemia-reperfusion injury can occur, also resulting in damage to bodily organs, tissues, or cells.

Compositions and methods disclosed herein may be employed for the treatment of circulatory shock in a subject. Shock can include Stage I shock, Stage II shock and Stage III shock. The compositions herein may be used to treat the initial stage of shock, in which cardiac output is insufficient to meet the body's metabolic needs, but not otherwise low enough to produce significant symptoms.

Compositions and methods disclosed herein may be used to treat cardiogenic shock, hypovolemic shock and vasodilatory shock. Cardiogenic shock refers to low blood flow or perfusion caused by heart malfunction, in which the heart does not adequately pump adequate blood. This can be caused by any condition that interferes with ventricular filling or emptying, such as embolism, ischemia, regurgitation and valve malfunction. Hypovolemic shock is associated with decreased intravascular volume. Hemorrhage from conditions such as ulcers, gastrointestinal injury, trauma, accidents, surgery, and aneurysm may cause hypovolemic shock. Loss of other body fluids, such as renal fluid, intravascular fluid, and peritoneal fluid, may also cause hypovolemic shock. Vasodilatory shock refers to inadequate blood flow caused by severe venous or arteriolar dilation. Vasodilatory shock may result from cerebral trauma, drug or poison toxicity, anaphylaxis, liver failure, bacteremia and sepsis.

Circulatory shock, including hemorrhagic shock, may also result from partially controlled or uncontrolled bleeding within one or more internal organs or vessels of a patient. Bleeding may result from any cause, including by way of example a ruptured aneurysm, dissected aorta, an ulcer, trauma or other gastrointestinal bleeding. Compositions herein may be administered to protect the heart, brain or other organs of a patient against injury caused by circulatory shock.

Treatment of Cancer

Compositions and methods disclosed herein may be used to treat cancers which are associated with leukocytes, inflammation, or metastases to the bone or other tissues and organs. Non-limiting examples of cancer include adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, thyroid cancer, oral cancer, nasopharyngeal cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplasia syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine cancer (e.g. uterine sarcoma), vaginal cancer, vulvar cancer, and Waldenstrom's macroglobulinemia. Compositions and methods disclosed herein may be used to treat radiation injury resulting from, for example, cancer treatment.

Combination Therapy

Compositions disclosed herein may be administered in combination with one or more other therapeutic agents, such as chemotherapy drugs, radiation, monoclonal antibodies, immune cells such as T cells, immunosuppressive agents including cyclosporine, tacrolimus, CTLA-4Ig, TNF inhibitors, IL-1 receptor blockers, anti-CD20 antibodies, inhibitors of IL-6, inhibitors of IL-17, inhibitors of IL-23, immune checkpoint drugs, cyclophosphamide, methotrexate, azathioprine, glucocorticoids, anabolic steroids, anti-inflammatory agents including non-steroidal anti-inflammatory drugs, aspirin, colchicine, indomethacin, phenylbutazone, drugs that decrease plasma uric acid levels, volume repleting agents, anti-epileptics, drugs to treat diabetes, drugs to treat hypovolemic shock, drugs to multiple sclerosis, drugs to treat kidney disease, drugs to treat asthma, drugs to treat gout, drugs to treat arthritis, drugs to treat immunodeficiencies, and drugs to treat osteoporosis. Such combination administration may be by means of a single dosage form which includes both a composition disclosed herein and one more other pharmaceutically active compounds, for example in a tablet, capsule, spray, inhalation powder, injectable liquid or the like. Alternatively, combination administration may be by means of administration of two different dosage forms, with one dosage form containing a composition disclosed herein, and the other dosage form including another pharmaceutically active compound. In this instance, the dosage forms may be the same or different. The term "co-administer" indicates that each of at least two compounds in the combination therapy are administered during a time frame wherein the respective periods of biological activity or effects overlap. Thus the term includes sequential as well as concurrent administration of compounds where one compound is one or more of the peptides of the present invention. In some embodiments, compositions disclosed herein can be chemically linked to other therapeutic agents prior to or for the purpose of co-administration. For example, compositions can be linked to, e.g., a monoclonal antibody or other protein, such as CTLA-4 Ig or etanercept. If more than one compound is co-administered, the routes of administration of the two or more compounds need not be the same.

Targeting Moieties

Polypeptides of the compositions herein may be conjugated or linked to targeting moieties. Targeting moieties (e.g., antibodies, peptibodies, dibodies, single-chain variable fragments (ScFv), or other modified antibodies) can target polypeptides of the compositions herein to specific sites, e.g., sites of inflammation or disease (e.g., cancer).

Methods of Administration

The method of administration and use may vary depending on the specific polypeptides of the compositions disclosed herein; the disease, indication, condition or syndrome to be treated; and other factors known to those in the art.

Compositions disclosed herein may be formulated for administration intranasally or to the respiratory tract, e.g., inhalation, in the form of an aerosol or solution for a nebulizer, or as a microfine powder for insufflation or inhalation (e.g., topically to the lung and/or airways), alone or in combination with one or more inert carriers or additional active pharmaceutical ingredients, and in the form of a solution, a suspension, an aerosol or a dry powder formulation. A formulation for inhalation may comprise a suitable powder base, diluent or carrier substance such as lactose, glucose, dextran, mannitol or another sugar or starch. The composition may be used in any of a variety of dry powder devices, such as a reservoir dry powder inhaler, a multi-dose dry powder inhaler, or a metered dose inhaler. The composition may include additional excipients, such as an alcohol, a surfactant, a lubricant, an anti-oxidant or a stabilizing agent. Suitable propellants include hydrocarbon, chlorofluorocarbon and hydrofluoroalkane propellants, or mixtures of any such propellants. Inhalation solutions also can be formulated in a liquefied propellant for aerosol delivery, such as with a pressurized metered dose inhaler.

Compositions disclosed herein may be formulated for subcutaneous injection. A pharmaceutical composition formulated for injection may be formulated for sustained release. Formulations may comprise a polyethylene glycol, such as polyethylene glycol 3350, and optionally one or more additional excipients and preservatives, including excipients such as salts, polysorbate 80, sodium hydroxide or hydrochloric acid to adjust pH, and the like. Any of a number of injectable and biodegradable polymers, which are preferably also adhesive polymers, may be employed in a sustained release injectable formulation.

Compositions disclosed herein may be formulated for local injection, such as local injection into the intra-articular space of a joint or intramuscularly or to other sites of inflammation. A pharmaceutical composition formulated for local injection may be optimized for delivery via, e.g., syringe, needle, catheter, infusion pump, pen device, microneedles, and the like.

For ocular applications, compositions described herein may be formulated in an ophthalmic dosage form and administered in the form of eye drops, eye washes or by means of other ocular delivery systems. Emulsions, ointments, gels, ocular inserts, biodegradable ocular inserts, liposomes, micro-particles, nanoparticles, nanospheres or ion pairing formulations may also be employed, which may, in some instances, result in increasing the ocular residence.

Compositions disclosed herein may be formulated for sublingual administration, wherein compositions herein are in contact with the mucous membrane beneath the tongue. A composition administered sublingually, for example, can be formulated as a tablet, pill, pellet, powder, or spray. Suitable formulations may include ointments, pastes, creams, capsules, solutions, syrups, drops, and granules.

Compositions disclosed herein may be formulated for depot administration. The depot administration may be a subcutaneous, intradermal, or intramuscular injection. The composition may be formulated as either solid or oil-based that allows for gradual absorption of the composition over a time period of hours, days, weeks, months, or years. In some aspects, suitable formulations may include zinc phosphate and PLGA polymer. In various aspects, depot formulation may be in the form of a natural or synthetic microparticle, a nanoparticle, a liposome, a carbon nanotube (CNT), a micelle, and/or a thermosensitive hydrogel. Natural or synthetic microparticles can possess high protein loading capacity and encapsulation efficiency, and can provide sustained release and controlled systemic delivery of biologically active peptides and proteins. For example, microparticles can be starch, alginate, collagen, poly (lactide-co-glycolide) (PLGA), or polycaprolactones (PCL). Nanoparticles can be colloidal carriers with sizes ranging from 10 to 1000 nm. Nanoparticles can protect the protein or peptide from degradation, prolong in vivo half-life, and provide long-term drug release. Additionally, nanoparticles can be fabricated from lipids, polymers or metal such as chitosan, alginate, PCL, polylactic acid (PLA), poly (glycolide), or PLGA. Liposomes can be bilayered vesicles with an aqueous core enclosed by phospholipid membrane of either synthetic or natural origin, and can vary in size from 20 nm to several hundred micrometers. Liposomes can protect a peptide or protein from in vivo degradation, which can prolong half-life, increase systemic circulation time, and increase bioavailability of the peptide or protein. Carbon nanotubes (CNTs) can be hollow cylindrical nano structures consisting of hexagonal arrangements of sp2-hybridized carbon atoms. A peptide or protein encapsulated in a CNT can have a prolonged half-life with sustained release over time. Micelles can be nano-scaled constructs formed by self-assembly of amphiphilic molecules and comprised of an inner hydrophobic core and an outer hydrophilic corona. Micelles can encapsulate a peptide or protein in their core, which can improve chemical and physical stability of the peptide or protein. Thermosensitive hydrogels can be an alternative particulate delivery approaches. Thermosensitive hydrogels can be polymeric solutions, which undergo sol-gel phase transition to form viscoelastic gel in response to changes in temperature. They can form temperature-dependent micellular aggregates, which can undergo gelation after further temperature increment due to aggregation or packing. For delivery, a peptide or protein can be mixed with polymer in a solution state. This solution, following administration, can form an in situ gel depot at physiological temperature such that the peptide or protein can remain entrapped and this entrapped cargo can be released from the depot over a period of time, providing extended release.

Formulations

Depending on the desired route of administration, the formulation of a composition may be varied. Thus the formulation may be suitable for subcutaneous injection, intravenous injection, intra-articular injection, topical applications, ocular applications, nasal spray applications, depot applications, intratracheal applications, inhalation applications, other transdermal applications and the like.

Pharmaceutical Compositions

The present disclosure provides a pharmaceutical composition comprising compositions disclosed herein and a pharmaceutically acceptable carrier. The carrier may be a liquid formulation, such as a buffered, isotonic, aqueous solution. Pharmaceutically acceptable carriers may also include excipients, such as diluents, carriers and the like, and additives, such as stabilizing agents, preservatives, solubilizing agents, buffers and the like.

Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents may be preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients may constitute the greater part, by weight or volume, of the preparation. For pharmaceutical formulations, it is also contemplated that any of a variety of measured-release, slow-release or sustained-release formulations and additives may be employed so that the dosage may be formulated so as to effect delivery of a composition disclosed herein over a period of time.

The therapeutic dose administered to a patient may vary between wide ranges, depending on the mode of administration, the formulation used, the patient's weight or mass, the patient's metabolism, the patient's age, the patient's health, and the response desired. In some embodiments, therapeutic doses may be administered to infants, children, young adults, adults, or elderly patients, and doses administered to patients may vary between wide ranges, depending on body mass, percent body fat, and/or clearance of administered compositions.

Because of the ease of administration, tablets and capsules may represent an advantageous oral dosage unit form. If desired, tablets may be coated by standard aqueous or non-aqueous techniques. The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Compositions herein may also be administered parenterally. Solutions or suspensions can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use can include sterile aqueous solutions or dispersions and sterile powders for the extemporaneous preparation of sterile injectable solutions or dispersions. The form may be sterile and fluid to the extent that it can be administered by syringe. The form preferably is stable under the conditions of manufacture and storage and is preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The pharmaceutical forms suitable for administration intranasally, intratracheally, or to the respiratory tract and lungs via inhalation can include an aerosol or solution for a nebulizer, or as a microfine powder for insufflation or inhalation (e.g., topically to the lung and/or airways), alone or in combination with one or more inert carriers or additional active pharmaceutical ingredients, and in the form of a solution, a suspension, an aerosol or a dry powder formulation. Compositions may be therapeutically applied by means of nasal administration, which refers to any form of intranasal administration. The compositions may be in an aqueous solution, such as a solution including saline, citrate or other common excipients or preservatives. The compositions may also be in a dry or powder formulation.

The pharmaceutical composition may also be delivered via topical drug delivery to the skin, conjunctiva, ear, mouth, and vaginal cavities, using formulations, including aqueous topical solutions, lotions, creams, pastes, ointments, gels, foams, powders, or pastes, either applied directly or in conjunction with methods and devices such as iontophoresis, microneedles, or a transdermal patch.

If in an aqueous solution, the compositions may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

Compositions may be therapeutically administered by means of an injection of a sustained release formulation or via depot administration. Compositions herein may be formulated for administration by a deep intramuscular injection, such as in the gluteal or deltoid muscle, comprising a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. Alternatively, other sustained release formulations may be employed for subcutaneous injection or local injection, e.g., intra-articular injection. Formulations may include one or more of nano/microspheres (such as compositions including PLGA polymers), liposomes, emulsions (such as water-in-oil emulsions), gels, zinc phosphate, insoluble salts or suspensions in oil.

The solutions can also contain conventional, pharmaceutically acceptable preservatives, stabilizers, cosolvents and/or penetration enhancers as well as viscoelastic substances included in artificial tear preparations. Pharmaceutically acceptable preservatives include quaternary ammonium compounds such as benzalkonium chloride, benzoxonium chloride or the like; alkyl-mercury salts of thiosalicylic acid such as thiomersal, phenylmercuric nitrate, phenylmercuric acetate or phenylmercuric borate; sodium perborate; sodium chlorite; parabens, such asmethylparaben or propylparaben; alcohols such as chlorobutanol, benzyl alcohol or phenyl ethanol; guanidine derivatives such as chlorohexidine or polyhexamethylene biguanide; sorbic acid; boric acid; or peroxide forming preservatives, or combinations of two or more of the foregoing. Pharmaceutically acceptable antioxidants and chelating agents may be used including various sulphites (such as sodium metabisulphite, sodium thiosulphate, sodium bisulfite, or sodium sulfite), α-tocopherol, ascorbic acid, acetylcysteine, 8-hydroxyquinolome, antipyrine, butylated hydroxyanisole or butylated hydroxytoluene, EDTA, and others. Cosolvents such as alcohols and others may also be used. Various substances can also be used to enhance formulation stability, such as cyclodextrins.

Compositions disclosed herein can be formulated for various methods of administration (e.g., intranasal, subcutaneous, intravascular, local injection, ocular, sublingual, topical, intra-articular, intratracheal, inhalation, other transdermal routes of administration). These formulations can also comprise delayed release or controlled release formulations. Delayed release of compositions can involve providing a coating or outer erodible (e.g., dissolvable) barrier for a composition (e.g., with an enteric coating) that delays the composition from disintegrating, dissolving, or otherwise releasing prior to an intended time of administration. For example, an enteric coating can be applied to oral medication in order to delay release until the composition has reached the intestines. In some embodiments, a plurality of coatings or outer barrier layers can be used to modulate or to delay release of the composition. The coating or outer barrier of the composition to be used in delayed or time-controlled can be selected based on the rate of erosion of the coating or barrier in the presence of physical agitation, enzymes, elevated or depressed pH, detergents, lipids, or solvents (e.g., aqueous solvents, organic solvents, inorganic solvents, etc.) and on the intended route of administration. In some embodiments, compositions can be delivered in or along with excipients suitable for delayed release administration of compositions described herein.

In some embodiments, a delayed release excipient or composition can comprise a polymer or a co-polymer. For example, a composition or delayed release excipient can comprise polylactic acid (PLA) and derivatives thereof, poly-L-lactide (PLLA), poly-D-lactide (PLDA), polyglycolic acid (PGA), poly(lactic-co-glycolic) acid, other polyglycolides and derivatives thereof, polylactide glycolide, polyanhydrides, polyorthoesters, polyacetals, poly(dioxanone), polyalkylcyanoacrylates, polyethylene glycol (PEG), polyglyconate, polycarbonates, polyacrylates, polycaprolactones (PCL), polyvaleroactone, polypropiolactone, polybutyrolactone, polypivalolactone, multiblock poly(ether ester urethane)s, poly(propylene glycol), chitosan, PEG-grafted chitosan polymer, PLGA-PEG-PLGA triblock copolymer, methoxy poly(ethylene glycol)-poly(sebacic acid-D, L-lactic acid)-methoxy poly(ethylene glycol) triblock copolymer, PCL-PEG-PCL triblock copolymer, polyester amides, or polyether esters.

A composition or delayed release excipient can also comprise cellulose derivatives, gelatin or its derivatives, saccharides or their derivatives, cyclodextrins, or any combination thereof. Delayed release excipients can also comprise direct compression diluents, such as direct compression sugars.

In some embodiments, a delayed release composition can comprise an emulsion, such as an oil-in-water emulsion. A delayed release composition comprising an emulsion can comprise a pharmaceutically active ingredient (e.g., one or more fragment of a proopiomelanocortin, a derivative thereof, a plurality of fragments of a proopiomelanocortin or plurality of derivatives thereof, or a combination thereof), a lipophilic phase, a hydrophilic phase, poorly water-soluble salt formulations, fatty acid esters, decanoic acid esters, and/or a gelling agent. In some respects, a pharmaceutically active ingredient can be insoluble in the lipophilic phase or it can be insoluble in a hydrophilic phase of a delayed release composition. In some embodiments the lipophilic phase can be an external phase with a hydrophilic phase incorporated therein. In some embodiments, the hydrophilic phase can be an external phase with a lipophilic phase incorporated therein.

Compositions to be used for delayed release administration can also comprise suspensions, injectable or topically applicable polymer matrices, injectable or topically applicable microspheres (e.g., polymer-based microspheres), oil-based injections, or injectable in situ systems. In some embodiments, compositions disclosed herein can comprise polymer-based microspheres or in situ-forming implants. An in situ-forming implant can comprise biodegradable products, which can be injected and designed to congeal in the body. In situ-forming implants can comprise thermally induced gelling systems (including pluronic gels or organogels, which can comprise lecithin), thermoplastic pastes (including reversible thermoplastic materials), in situ cross-linked polymer systems, in situ polymer precipitation systems, and in situ solidifying organogels. In some embodiments, materials used to comprise a delayed release composition described herein can be chosen or designed such that the sol/gel point is at or about body temperature, skin temperature, or room temperature. In some embodiments, materials used to comprise a delayed release composition described herein can be chosen or designed such that the sol/gel point is 1, 2, 3, 4, or 5 degrees Celsius above or below body temperature, skin temperature, or room temperature. In some aspects, room temperature can be from 19 degrees Celsius to 26 degrees Celsius. In some aspects, body temperature can be from 35 degree Celsius to 40 degrees Celsius. In some aspects, skin temperature can be from 31 degrees Celsius to 37 degrees Celsius.

A delayed or sustained release formulation of the compositions described herein can be active in therapeutically relevant concentrations for a period of at least 1 hour, at least 2 hours, at least 6 hours, at least 12 hours, at least 24 hours, at least 2 days, at least 5 days, at least 7 days, at least 10 days, at least 14 days, at least 21 days, or at least 28 days.

Methods of Administration

Administration may include various means of administration including through the skin, mucous membranes, sublingual administration, buccal administration, oral administration, dermal administration, inhalation administration, nasal administration, urethral administration, vaginal administration, and the like. Formulations may be administered by injection, e.g., intravenous, subcutaneous, intramuscular, intra-articular, intraperitoneal, intracerebral, intra-arterial, intrathecal, within the spine, and other means known in the art (e.g., injection into the bursa or tendon). Formulations may be administered as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art.

Drug delivery through the skin can be accomplished via any of a variety of creams, ointments, gels, lotions and the like as well as through the use of iontophoresis, microneedles, or a transdermal patch. In the case of iontophoresis, drug delivery, either individually or as a combination of two or more drugs, via a semi-dry patch may be applied to the skin followed by a local electrical current, inducing transdermal flux of the drug through the stratum corneum, sweat ducts, or sebaceous capillary ducts. In the case of microneedle drug delivery through the skin, a device with at least one needle with a diameter on the order of tens to hundreds of micrometers in diameter may be used to puncture the skin and to deliver a drug from a reservoir in the form of a solid, semi-solid, or liquid. In the case of transdermal patches, an adhesive patch may be used to dispense drug directly for absorption across the skin via a reservoir and release membrane, which is in contact with the skin.

Therapeutically Effective Amounts

A therapeutic dosage of compositions described herein may vary between wide ranges depending upon the mode of administration, the formulation used, and the response desired. The dosage for treatment or prophylactic treatment is administration, by any of the foregoing means or any other means known in the art, of an amount sufficient to bring about the desired therapeutic effect, e.g. therapeutically alleviate an inflammatory condition, or prophylactic effect, respectively.

Compositions to be therapeutically administered to human patients can comprise a single dose of at least 0.1 nanomoles per kilogram (kg) and not more than 300 nanomoles per kg, at least 0.3 nanomoles per kilogram and not more than 100 nanomoles per kg, at least 0.5 nanomoles per kilogram and not more than 50 nanomoles per kg, at least 1 nanomole per kilogram and not more than 30 nanomoles per kg, at least 2 nanomoles per kilogram and not more than 20 nanomoles per kg. For example, single doses therapeutically administered to a human patient weighing 70 kg can range from at least 140 nanomoles to at least 1,400 nanomoles and singles doses therapeutically administered to a human patient weighing 90 kg can range from at least 180 nanomoles to at least 1,800 nanomoles.

Compositions to be therapeutically administered as a method of reducing inflammation can comprise a single dose that provides a maximum plasma cortisol concentration (e.g., causes the patient to exhibit a maximum plasma cortisol concentration) following administration of the composition that is less than 6 times the basal level concentration, less than 5.5 times the basal level concentration, less than 5 times the basal level concentration, less than 4.5 times the basal level concentration, less than 4 times the basal level concentration, less than 3.5 times the basal level concentration, less than 3 times the basal level concentration less than 2.5 times the basal level concentration, less than 2 times the basal level concentration, or less than 1.5 times the basal level concentration.

Protein Production

Recombinant Protein Production

Polypeptides of the compositions and methods disclosed herein can be produced recombinantly using cell-based or cell-free systems. When using cell-based systems, host cells, or the cells in which the protein is produced, can be selected with various factors in mind, e.g., post-translational modifications, molecular folding, and multi-domain eukaryotic proteins synthesis. DNA encoding the peptide of interest, which would serve as the template for protein production, can be introduced into the host cell using various methods, such as electroporation and viral delivery. The DNA may stably integrate into the host cell genome. In some cases, stable integration is not required. Many different host cells are available, including those derived from bacteria, yeast, insect, and mammalian cells. Cell-based systems may utilize bacterial hosts, such as *E. coli, C. glutamicum*, or *P. fluorescens*, or eukaryotic hosts such as yeast cells including *S. cerevisiae* and *Pichia pastoris*; insect cells including Sf9 and Sf21 cells; and mammalian cells (e.g., adherent and suspension cells) including mouse myeloma-derived NS0 cells, baby hamster kidney (BHK) cells, human embryonic kidney (HEK) cells, and Chinese hamster ovary (CHO) cells. Proteins expressed in cell-based systems may be constitutively or continually expressed. Alternatively, protein expression may be inducible, wherein transcriptional activation is regulated by an additional molecule, such as doxycycline in a tetracycline inducible expression system.

As an alternative, cell-free systems can be used for protein synthesis. Cell-free protein synthesis generally refers to the production of polypeptides and proteins using biological machinery, e.g., ribosomes, aminoacyl-tRNA synthetases, translation initiation and elongation factors, nucleases, etc., without the use of living cells. The biological machinery for cell-free protein expression can be harvested from bacteria such as *E. coli*; insect cells such as Sf9 and Sf21; yeast; mammalian cells such as rabbit reticulocytes; and wheat germ extracts. Reaction solutions comprising the biological machinery (e.g., ribosomes, aminoacyl-tRNA synthetases, translation initiation and elongation factors, nucleases, etc), DNA template, amino acids, and other necessary supplements can be incubated together to facilitate the in vitro translation of protein. Cell-free protein synthesis enables direct access to and control of the translation environment, which may be advantageous for the optimization of protein production and incorporation of non-natural amino acids, amino acid analogues, modified amino acids, etc.

Synthetic Peptide Production

Polypeptides of the compositions and methods herein can be produced synthetically, e.g., via solid-phase peptide synthesis or liquid-phase peptide synthesis. SPPS involves covalently linking amino acids in an ordered manner to form a synthetic peptide with a desired amino acid sequence. Solid supports, e.g., polystyrene resin, polyamide resin, polyethylene (PEG) hybrid polystyrene resin, or PEG-based resin, are provided as a structural support for the elongation of the peptide, generally from the C-terminus to the N-terminus. Amino acids with "temporary" protecting groups, e.g., 9-fluorenylmethyloxycarbonyl group (Fmoc) or t-butyloxycarbonyl (Boc) protecting groups, are added to the N-terminus of a growing peptide chain through iterations of various steps including deprotection, e.g., removal of protecting groups, and reaction steps, e.g., formation of peptide bonds.

Liquid-phase peptide synthesis similarly adds amino acids to a growing peptide chain in an ordered fashion, however, without the aid of a solid support. Liquid-phase peptide synthesis generally requires that the C-terminus of the first amino acid be protected and the growing peptide chain be isolated from the reaction reagents after each amino acid addition so that one amino acid is not unintentionally incorporated two or more times into the peptide chain.

Solid-phase and liquid-phase peptide synthesis can allow the incorporation non-natural amino acids, amino acid analogues, modified amino acids, etc, not found in endogenous peptides to form synthetic peptide variants. Synthetic peptide synthesis can also allow for better control of peptide uniformity, e.g., glycosylation patterns, as liquid-phase and solid-phase peptide synthesis systems tack the machinery for protein post-translational modifications.

Following synthesis, peptides can be purified using various strategies based on a combination of separation methods that exploit the physiochemical characteristics of peptides, including size, charge and hydrophobicity. Purification techniques include size-exclusion chromatography (SEC), ion exchange chromatography (IEC), partition chromatography, high-performance liquid chromatography (HPLC), and reverse-phase chromatography (RPC).

EXAMPLES

The invention is further illustrated by the following non-limiting examples.

Example 1

Murine Air Pouch Study

An air pouch was formed by injecting 6 mL of sterile air subcutaneously into a shaved skin site on the dorsal surface of mice on Day 0. The pouches settle for 3 days to permit healing of the wound. The pouch is then re-inflated with 3 mL of sterile air on Day 3. Three days after re-inflation on Day 6, mice are treated with compositions described herein prior to the administration of monosodium urate crystals (MSU) to drive an inflammatory response.

General clinical observations, body weight, cytokine profiling in blood, and inflammatory cell characterization are performed. Four hours after injection of MSU, exudate is collected for total white blood cell (WBC) analysis, WBC subpopulation analysis, and cytokine profiling. Total WBC counts are determined. Counts for WBC subpopulations, including neutrophils, lymphocytes, monocytes, eosinophils, and basophils, are also determined. The levels of cytokines, such as Interleukin-1β (IL-1β), tumor necrosis factor-alpha (TNF-α), transforming growth factor β (TGF-β), Interleukin-6 (IL-6), Interleukin-8 (IL-8), Interleukin-10 (IL-10), Interleukin-12 (IL-12), and Interleukin-17 (IL-17); and chemokines such as keratinocyte chemoattractant (KC), macrophage inflammatory protein-1β (MIP-1β) and monocyte chemoattractant protein-1 (MCP-1) are determined.

Example 2

Administration of Compositions in Murine Air Pouch Models of Gout

An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The pouches settled for 3 days to permit healing of the wound. The pouch was then re-inflated with 3 mL of sterile air on Day 3. Three days after re-inflation on Day 6, compositions described herein were administered via subcutaneous injection 1 hour prior to the administration of 30 mg monosodium urate crystals (MSU) directly into the air pouch to drive an inflammatory response. Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include total white cell count, differential white blood cell (WBC) population, and levels of cytokines and chemokines. The following treatment groups were tested:
1) Vehicle (control)
2) NDP-α-MSH, SEQ ID NO. 12 (administered at 1, 3, and 10 nmole/mouse for individual mice)
3) ACTH$_{1-24}$, SEQ ID NO. 10 (administered at 1, 3, and 10 nmole/mouse for individual mice)
4) NDP-α-MSH+ACTH$_{1-24}$ mixture, SEQ ID NO. 10 and SEQ ID NO. 12 (administered at
    two dosages, (a) [1 nmole NDP-α-MSH+1 nmole ACTH$_{1-24}$)]/mouse and (b) [3 nmole NDP-α-MSH+3 nmole ACTH$_{1-24}$]/mouse)

Figure 2:
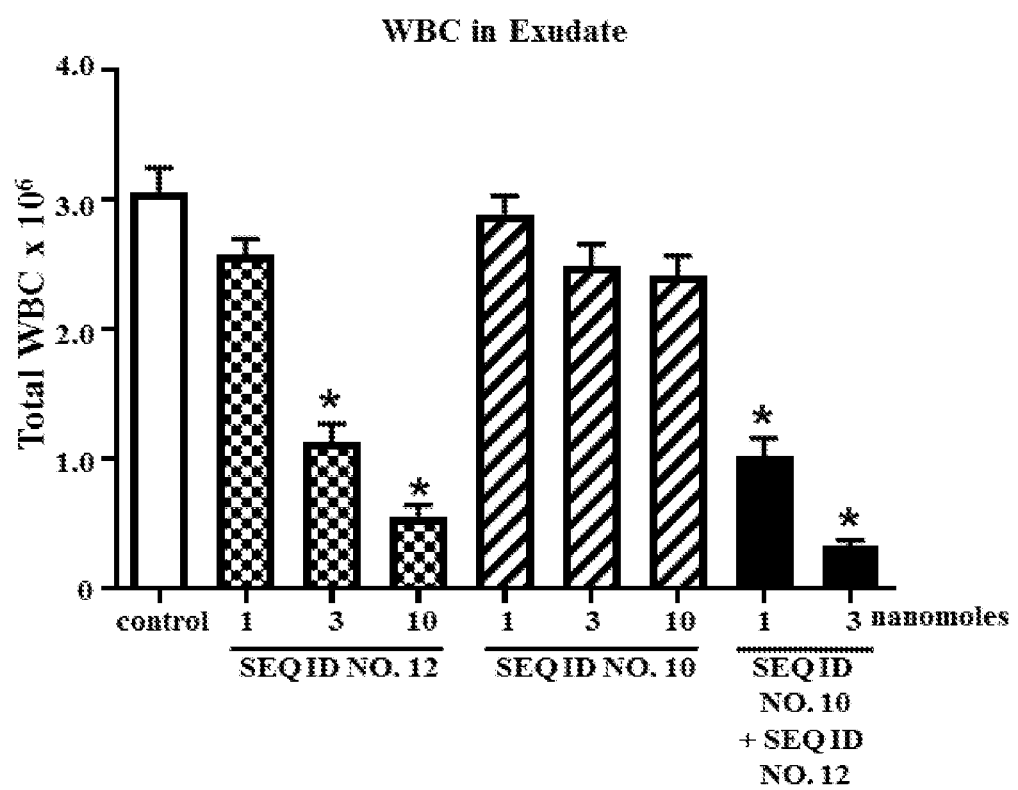
FIG. 2 shows white blood cell counts in collected exudate from murine models of gout treated with compositions disclosed herein.
Figure 3:
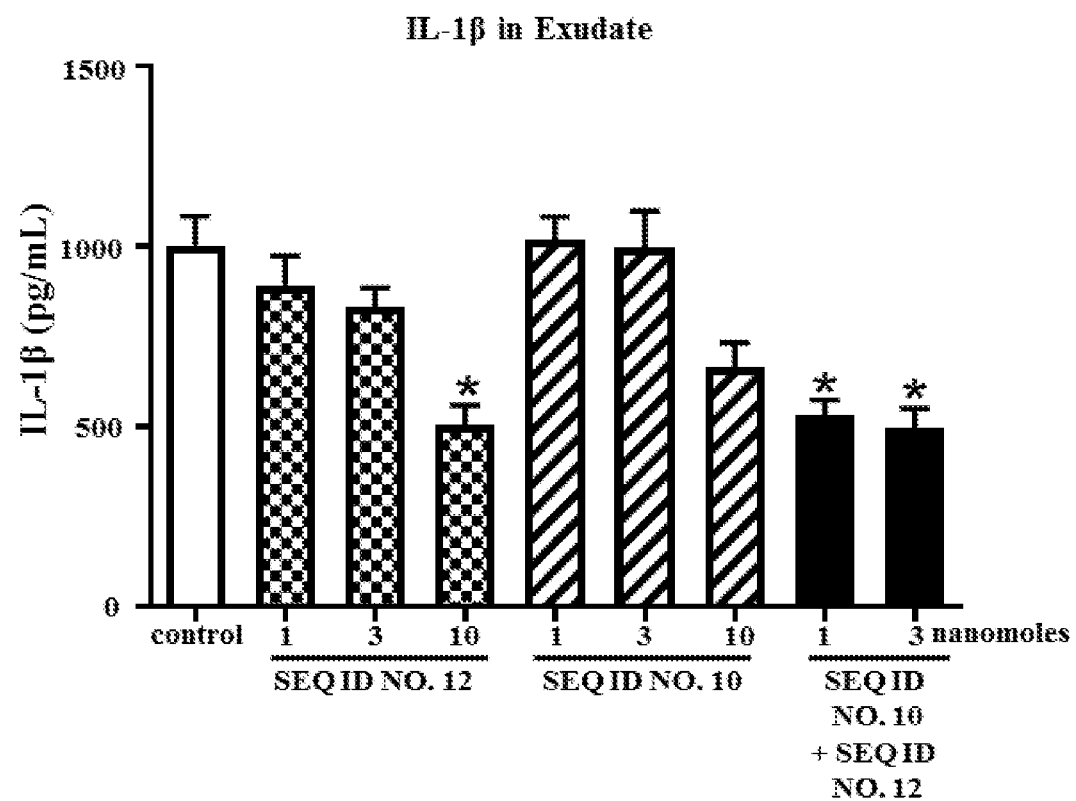
FIG. 3 shows concentrations of IL-1$\beta$ measured by ELISA in collected exudate from murine models of gout treated with compositions disclosed herein.
Figure 4A:
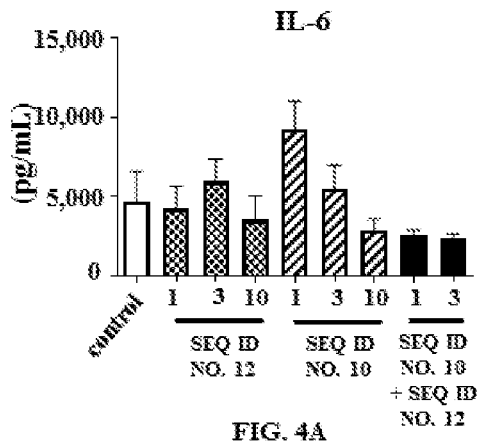
FIG. 4 shows concentrations of additional cytokines and chemokines in exudate involved in the inflammatory response as measured by Luminex (Biorad 23-Plex)
Figure 4B:
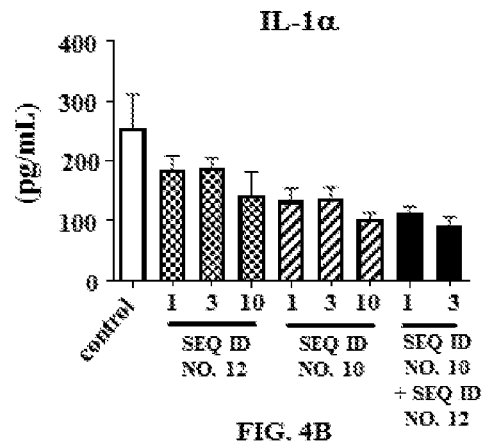
Figure 4C:
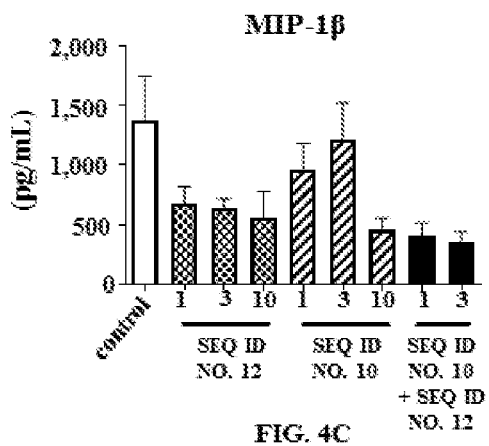
Figure 4D:
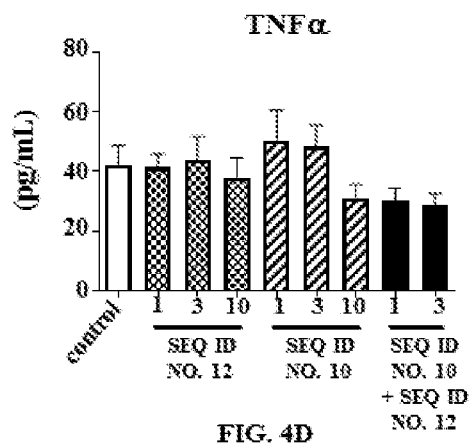
Figure 4E:
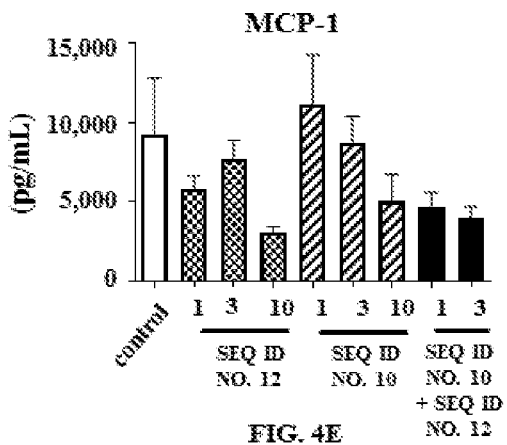
Figure 4F:
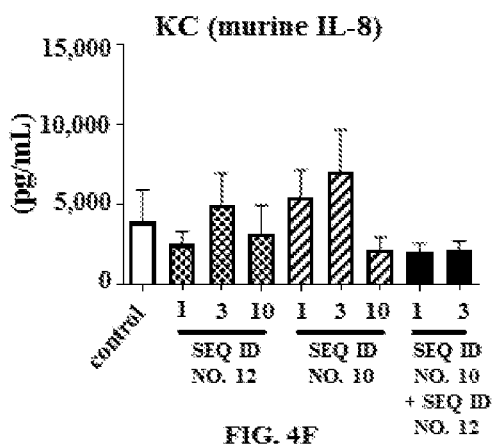

Neutrophil counts in collected exudate are shown in FIG. 1 and quantified in Tables 2 and 3. Table 2 provides the absolute neutrophil count. Table 3 provides the percent reduction in neutrophil count. WBC counts in collected exudate are shown in FIG. 2. Concentrations of IL-1β in collected exudate measured by ELISA are shown in FIG. 3. Concentrations of additional cytokines and chemokines involved in the inflammatory response (e.g., IL-6 (FIG. 4A), IL-la (FIG. 4B), MIP-1β (FIG. 4C), TNF-α (FIG. 4D), MCP-1 (FIG. 4E), and KC (FIG. 4F)) measured by Luminex (Biorad 23-Plex) are shown in FIG. 4.

TABLE 2

Quantification of absolute neutrophils count in collected exudate in murine models of gout treated with compositions disclosed herein
Absolute Number of Neutrophils (Number of Cells in Exudate)

| | | SEQ ID NO. 12 | | | SEQ ID NO. 10 | | | SEQ ID NO. 10 + SEQ ID NO. 12 | |
|---|---|---|---|---|---|---|---|---|---|
| | Vehicle | 1 nmole | 3 nmole | 10 nmole | 1 nmole | 3 nmole | 10 nmole | 1 nmole | 3 nmole |
| | 1666000 | 1692180 | 90720 | 184800 | 2110720 | 1632000 | 321300 | 156800 | 61500 |
| | 2597760 | 1632000 | 8000 | 24000 | 2295000 | 2361600 | 123000 | 161840 | 55200 |
| | 1638400 | 2320500 | 134400 | 58520 | 2724480 | 854400 | 1248320 | 140000 | 74100 |
| | 1101600 | 875160 | 246960 | 316800 | 1626900 | 342000 | 835200 | 144000 | 14000 |
| | 2065500 | 2497440 | 355740 | 82650 | 2456500 | 887400 | 361200 | 195840 | 49280 |
| | 1540800 | 1244400 | 213180 | 159600 | 1346400 | 1147500 | 239120 | 204120 | 86940 |
| | 2086920 | 1580800 | 579150 | 29450 | 2027520 | 2020480 | 1303680 | 318420 | 34800 |
| | 1377000 | 2035240 | 257400 | 122400 | 880640 | 2168100 | 190400 | 177940 | 31900 |
| Mean | 1759248 | 1734715 | 256404 | 122278 | 1933520 | 1426685 | 577778 | 187370 | 50965 |

TABLE 3

Quantification of percent reduction of total neutrophil counts
in murine models of gout treated with compositions disclosed herein
Percent Decrease in Neutrophils Relative to Vehicle

|  | SEQ ID NO. 12 | | | SEQ ID NO 10 | | | SEQ ID NO. 10 + SEQ ID NO.12 | |
| --- | --- | --- | --- | --- | --- | --- | --- | --- |
| Vehicle | 1 nmole | 3 nmole | 10 nmole | 1 nmole | 3 nmole | 10 nmole | 1 nmole | 3 nmole |
| 5 | 4 | 95 | 89 | −20 | 7 | 82 | 91 | 97 |
| −48 | 7 | 100 | 99 | −30 | −34 | 93 | 91 | 97 |
| 7 | −32 | 92 | 97 | −55 | 51 | 29 | 92 | 96 |
| 37 | 50 | 86 | 82 | 8 | 81 | 53 | 92 | 99 |
| −17 | −42 | 80 | 95 | −40 | 50 | 79 | 89 | 97 |
| 12 | 29 | 88 | 91 | 23 | 35 | 86 | 88 | 95 |
| −19 | 10 | 67 | 98 | −15 | −15 | 26 | 82 | 98 |
| 22 | −16 | 85 | 93 | 50 | −23 | 89 | 90 | 98 |
| Mean 0 | 1 | 87 | 93 | −10 | 19 | 67 | 89 | 97 |

Example 3

Administration of Compositions in Murine Air Pouch Models of Gout

An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The pouches settled for 3 days to permit healing of the wound. The pouch was then re-inflated with 3 mL of sterile air on Day 3. Three days after re-inflation on Day 6, compositions described herein were administered via subcutaneous injection 1 hour prior to the administration of 30 mg monosodium urate crystals (MSU) directly into the air pouch to drive an inflammatory response. Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include total white cell count, differential white blood cell population, and levels of cytokines and chemokines. The following treatment groups were tested:
1) Vehicle (control)
2) γ-MSH-ACTH, SEQ ID NO. 1 (administered at 10, 15, and 20 nmole/mouse for individual mice)
3) γ-MSH, SEQ ID NO. 9 (administered at 10, 15, and 20 nmole/mouse for individual mice)
4) ACTH$_{1-24}$, SEQ ID NO. 10 (administered at 10, 15, and 20 nmole/mouse for individual mice)
5) γ-MSH+ACTH$_{1-24}$ mixture, SEQ ID NO. 9 and SEQ ID NO. 10 (administered at two dosages, (a) [10 nmole γ-MSH+10 nmole ACTH$_{1-24}$]/mouse and (b) [15 nmole γ-MSH+15 nmole ACTH$_{1-24}$]/mouse)

Figure 5:
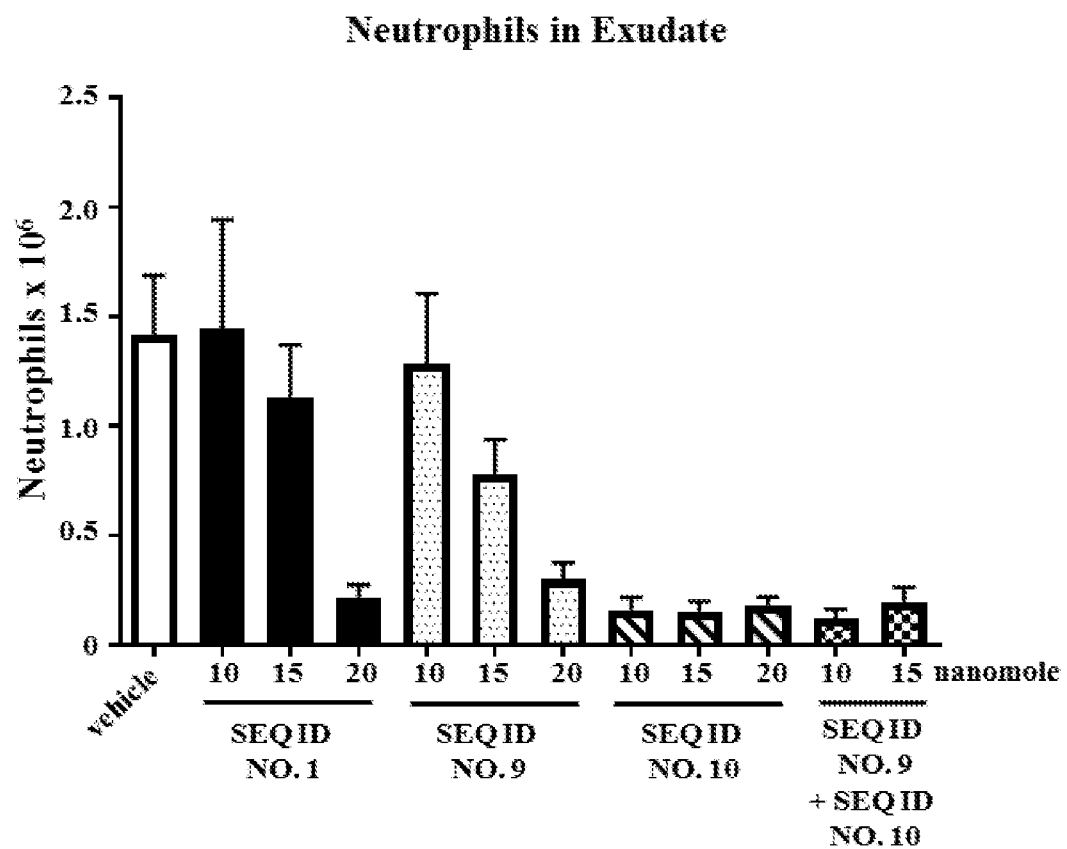
FIG. 5 shows neutrophil counts in collected exudate from murine models of gout treated with compositions disclosed herein.

Neutrophil counts in collected exudate are shown in FIG. 5.

Example 4

Administration of Compositions in Murine Air Pouch Models of Gout

An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The pouches settled for 3 days to permit healing of the wound. The pouch was then re-inflated with 3 mL of sterile air on Day 3. Three days after re-inflation on Day 6, compositions described herein were administered via subcutaneous injection 1 hour prior to the administration of 30 mg monosodium urate crystals (MSU) directly into the air pouch to drive an inflammatory response. Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include total white cell count, differential white blood cell population, and levels of cytokines and chemokines. The following treatment groups were tested:
1) Vehicle (control)
2) Colchicine (1 mg/kg)
3) γ-MSH, SEQ ID NO. 9 (administered at dosages of 2.5, 7.5 and 22.5 nmole/mouse)
4) γ-MSH-ACTH, SEQ ID NO. 1 (administered at dosages of 7.5 and 22.5 nmole/mouse)
5) γ-MSH-α-MSH, SEQ ID NO. 4 (administered at dosages of 7.5 and 22.5 nmole/mouse)
6) NDP-γ-MSH-α-MSH, SEQ ID NO. 6, (administered at dosages of 7.5 and 22.5 nmole/mouse)
7) NDP-α-MSH, SEQ ID NO. 12, (administered at a dosage of 7.5 nmole/mouse)

Figure 6:
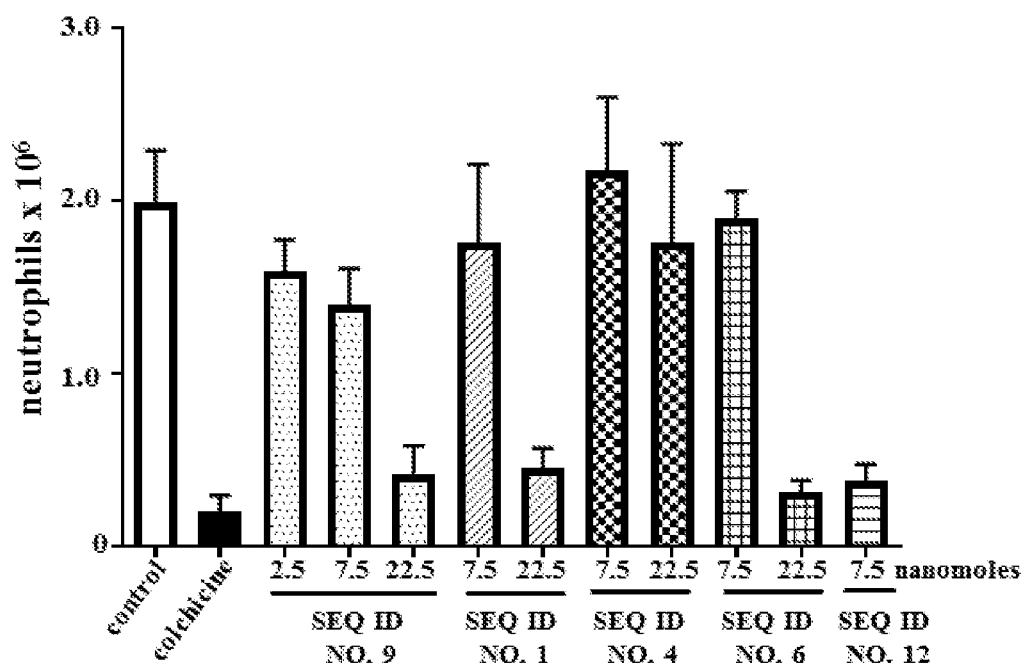
FIG. 6 shows neutrophil counts in collected exudate from murine models of gout treated with compositions disclosed herein.

Neutrophil counts in collected exudate are shown in FIG. 6.

Example 5

Administration of Compositions in Murine Air Pouch Models of Gout

An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The pouches settled for 3 days to permit healing of the wound. The pouch was then re-inflated with 3 mL of sterile air on Day 3. Three days after re-inflation on Day 6, compositions described herein were administered via subcutaneous injection 1-3 hours prior to the administration of 30 mg monosodium urate crystals (MSU) directly into the air pouch to drive an inflammatory response. Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include total white cell count, differential white blood cell population, and levels of cytokines and chemokines. The following treatment groups were tested:
1) Vehicle (control)
2) Colchicine (1 mg/kg)
3) ACTH$_{1-39}$, SEQ ID NO. 19 (administered at a dosage of 100 mg/mouse)
4) delta POMC glycopolymer, SEQ ID NO. 21 (administered at a dosage of 200 µg/mouse)
5) γ-MSH-ACTH$_{1-39}$, SEQ ID NO. 22, (administered at a dosage of 200 µg/mouse)

Figure 7:
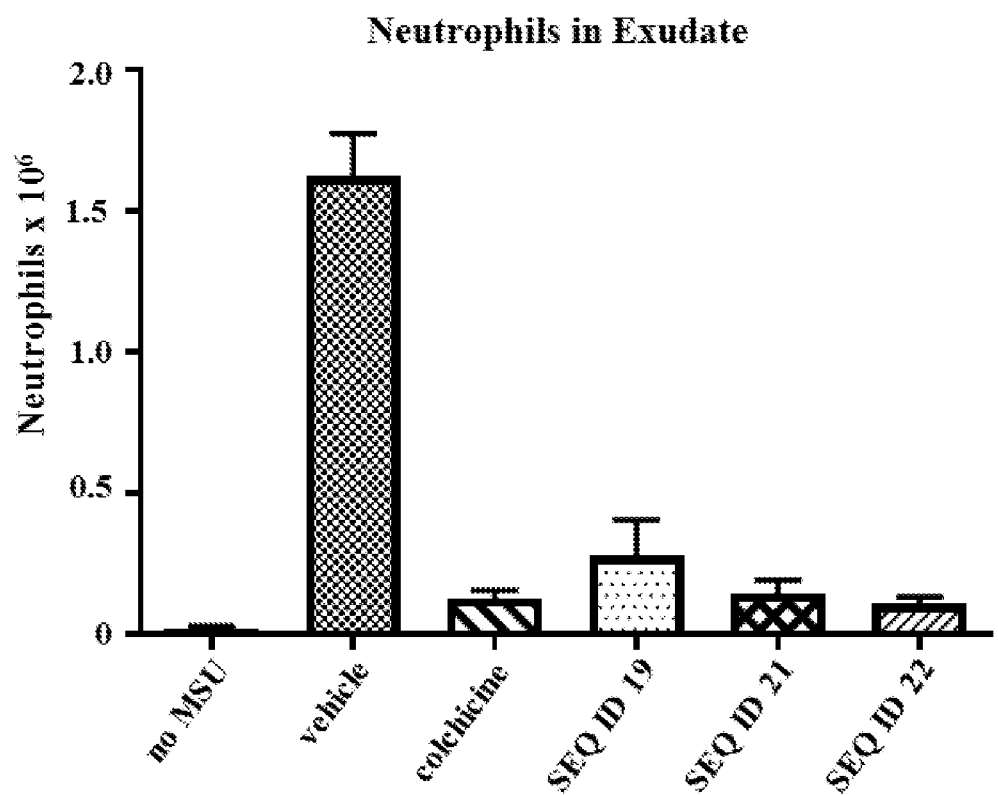
FIG. 7 shows neutrophil counts in collected exudate from murine models of gout treated with compositions disclosed herein.

Neutrophil counts in collected exudate are shown in FIG. 7.

Example 6

Administration of Compositions in Murine Air Pouch Models of Gout

An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The wound result from the pouch was allowed to heal for 3 days without any intervention. The pouch was then re-inflated with 3 mL of sterile air on Day 3. Three days after re-inflation on Day 6, compositions described herein were administered via subcutaneous injection 1 hour prior to the administration of 30 mg monosodium urate crystals (MSU) directly into the air pouch to induce an inflammatory response. Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include determining neutrophil counts and IL-1β cytokine concentrations. The following treatment groups were tested (n=8 animals per group, all animals of peptide groups administered peptides at dosages of 3 nmol/mouse and 10 nmol/mouse):

1) Vehicle (control)
2) ACTH$_{1-24}$, SEQ ID NO. 10
3) NDP-α-MSH-linker-linker-ACTH$_{1-24}$, SEQ ID NO. 23
4) ACTH$_{1-24}$-linker-linker-NDP-α-MSH, SEQ ID NO. 26

Figure 8:
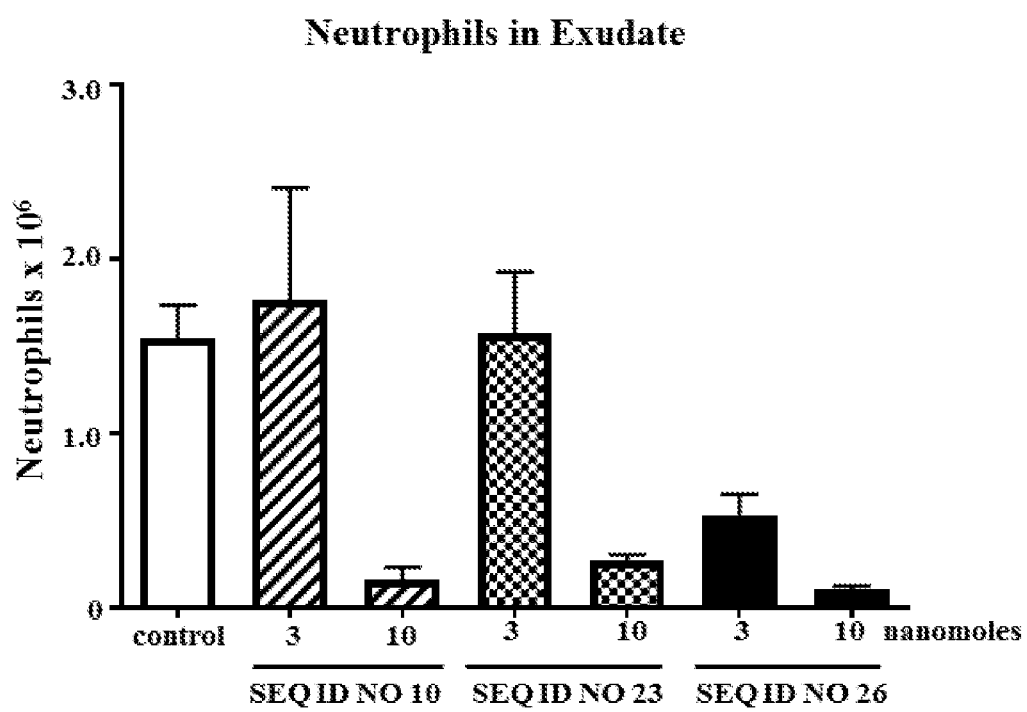
FIG. 8 shows neutrophil counts in collected exudate from murine models of gout treated with compositions disclosed herein.
Figure 9:
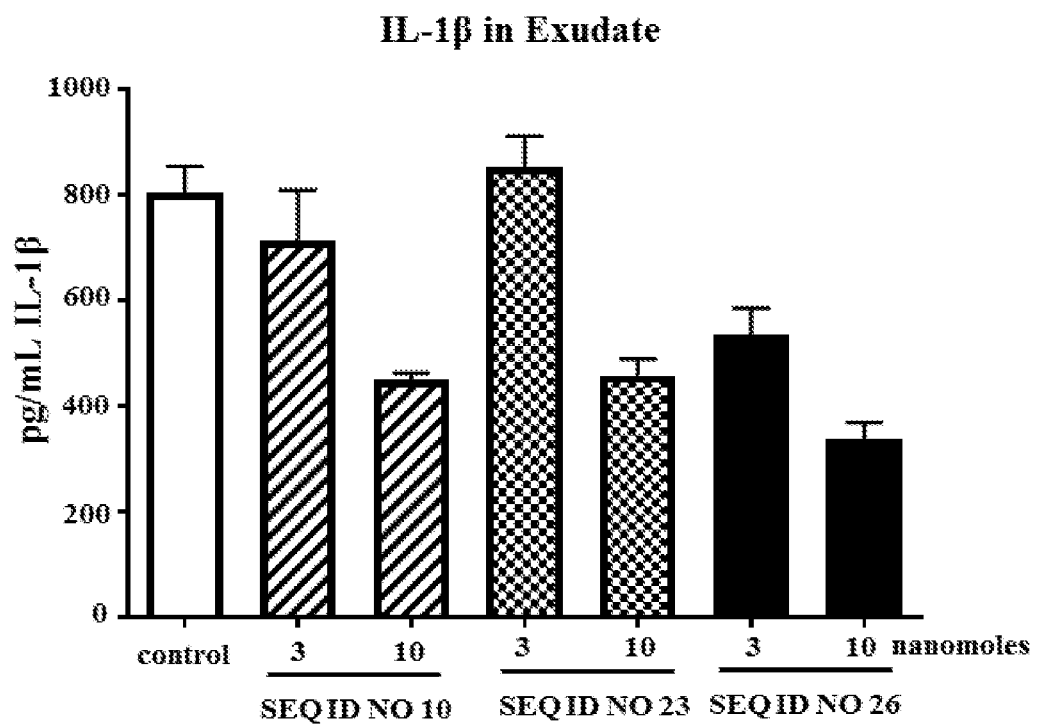
FIG. 9 shows concentrations of IL-1$\beta$ measured by ELISA in collected exudate from murine models of gout treated with compositions disclosed herein.

SEQ ID NOS. 23 and 26 are alternate arrangements of ACTH$_{1-24}$ and NDP-α-MSH. Neutrophil counts in collected exudate are shown in FIG. 8. IL-1β cytokine concentrations in collected exudate are shown in FIG. 9. SEQ ID NO. 23 and SEQ ID NO. 26 are more active than SEQ ID NO. 10 in reducing neutrophil counts and IL-1β cytokine concentrations in collected exudate, and the arrangement of SEQ ID NO. 26 is generally more active than that of SEQ ID NO. 23.

Example 7

Determination of EC50 Values

For each of MCR1, MCR2, MCR3, MCR4 and MCR5, human cDNA was subcloned into an expression vector and transfected into Chinese Hamster Ovary (CHO) cells to generate CHO-MCR1, CHO-MCR2, CHO-MCR3, CHO-MCR4 cells, and CHO-MCR5 cells. MCR stimulation in response to polypeptides added to cell culture media was measured by cAMP production via LANCE cAMP assay (Perkin Elmer cat #AD0263). In this example, experiments were performed using multiple lots of cells (e.g., cell pools).

The manufacturer's recommended protocol was followed. Briefly, for each polypeptide, 5 uL of polypeptide was added to 10 wells (10 serial dilutions) of a 384-well white, low volume, round bottom assay plate (Corning #4512). To each well was added 5 uL of cell suspension (10,000 CHO-MCR cells per well, with Alexa-labeled antibodies). The mixtures were incubated for 30 minutes at room temperature. Then, to each well was added 10 uL of Detection Mix. The mixtures were incubated for 120 minutes at room temperature. The plate was read on an EnVision reader (665 nm). This process was repeated for each of CHO-MCR1, CHO-MCR2, CHO-MCR3, CHO-MCR4 and CHO-MCR5 cells. Data was processed using GraphPad Prism v 6.03 (variable slope, four parameters) and is presented in Table 4.

TABLE 4

EC50 values for compositions of the present disclosure (* Cell pools A and B were partially enriched for MCR expression, whereas cell pool C was an optimized cell bank. ** ND denotes not determined)

| Description | SEQ ID NO. | MCR1 EC50 (nM) | MCR2 EC50 (nM) | MCR3 EC50 (nM) | MCR4 EC50 (nM) | MCR5 EC50 (nM) | Cell Pool* |
|---|---|---|---|---|---|---|---|
| γ-MSH - ACTH$_{1-24}$ | 1 | 22 | 26 | 38 | ND | ND** | A |
| γ-MSH with linker | 9 | 19 | >100 | 11 | >100 | ND | B |
| ACTH$_{1-24}$ | 10 | 0.34 | 0.13 | 7.3 | 34 | 190 | C |
| α-MSH | 11 | 0.37 | >100 | 6.8 | 92 | 130 | C |
| NDP-α-MSH | 12 | 0.11 | >100 | 0.17 | 0.18 | 1.1 | C |
| ATCH$_{1-39}$ | 19 | 0.55 | 0.14 | 18 | 31 | ND | B |
| γ-MSH - ACTH$_{1-24}$ linker without cleavable site | 14 | 11 | >100 | 16 | ND | ND | A |
| γ-MSH - ACTH$_{1-24}$ without linker and cleavage site | 15 | 12 | 5 | 33 | ND | ND | A |
| NDP-α-MSH - linker-linker - ACTH$_{1-24}$ | 23 | 0.46 | 100 | 1.8 | 2.2 | 9.8 | C |
| NDP-α-MSH - linker-Furin | 24 | 0.333 | 21 | 4 | 6.5 | ND | B |

TABLE 4-continued

EC50 values for compositions of the present disclosure (* Cell pools
A and B were partially enriched for MCR expression, whereas cell pool
C was an optimized cell bank. ** ND denotes not determined)

| Description | SEQ ID NO. | MCR1 EC50 (nM) | MCR2 EC50 (nM) | MCR3 EC50 (nM) | MCR4 EC50 (nM) | MCR5 EC50 (nM) | Cell Pool* |
|---|---|---|---|---|---|---|---|
| site-linker - ACTH$_{1-24}$ | | | | | | | |
| NDP-α-MSH - linker-MMP site-linker - ACTH$_{1-24}$ | 25 | 2.4 | 76 | 17 | 14 | ND | B |
| ACTH$_{1-24}$ - linker-linker - NDP-α-MSH | 26 | 0.39 | 0.21 | 0.8 | 1.8 | 9.6 | C |
| ACTH$_{1-24}$ - linker-Furin site-linker - NDP-α-MSH | 27 | 0.202 | 1 | 0.453 | 1.9 | ND | B |
| ACTH$_{1-24}$ - linker-MMP site-linker - NDP-α-MSH | 28 | 1.6 | 0.318 | 4.7 | 5.8 | ND | B |
| ACTH$_{1-24}$ - linker-MMP (broad) site-linker - NDP-α-MSH | 29 | 0.528 0.36 | 0.05 | 1 | 4.8 | ND | B |
| NDP-α-MSH - linker-MMP (broad) site-linker - ACTH$_1$ | 32 | 0.295 | 191 | 1.5 | 1.9 | ND | B |
| Acetylated α-MSH | 33 | 0.57 | >100 | 52 | >100 | >100 | C |
| ACTH$_{1-24}$ - proconvertase - NDP-α-MSH | 38 | 0.44 | 1.05 | 0.51 | 1.6 | ND | B |
| ACTH$_{1-24}$ - natural N-terminal spacer - NDP-α-MSH | 39 | 0.63 | 0.18 | 0.62 | 1.6 | ND | B |
| ACTH$_{1-24}$ - natural C-terminal spacer - NDP-α-MSH | 40 | 0.8 | 0.15 | 1.66 | 8.7 | ND | B |
| ACTH$_{1-24}$ - proconvertase - α-MSH | 41 | 0.92 | 1.08 | 6.1 | 26 | ND | B |
| ACTH$_{1-24}$ - natural N-terminal spacer - α-MSH | 42 | 0.82 | 0.15 | 6.2 | >20 | ND | B |
| ACTH$_{1-24}$ - natural C-terminal spacer - α-MSH | 43 | 1.02 | 0.18 | 22 | >20 | ND | B |
| NDP-ACTH$_{4-9}$ - βAla-G-βAla - NDP-ACTH$_{4-9}$ | 44 | 0.35 | >20 | 25 | 6.7 | ND | B |
| NDP-ACTH$_{4-9}$ - βAla-G-βAla - ACTH$_{1-24}$ | 45 | 0.16 | 18.5 | 5.5 | 2.4 | ND | B |
| NDP-ACTH$_{4-9}$ - ACTH$_{1-24}$ | 46 | 0.17 | >20 | 6.8 | 0.8 | ND | B |
| NDP-ACTH | 47 | 0.11 | 21 | 0.21 | 0.22 | 1.1 | C |
| ACTH$_{1-24}$-point-5 | 48 | 0.31 | 0.11 | 10 | 60 | >100 | C |
| ACTH$_{1-24}$-point-1-2 | 49 | 0.43 | 7.1 | 10 | 62 | 275 | C |
| ACTH$_{1-24}$-point-3-5 | 50 | 0.54 | 20 | 14 | 128 | >100 | C |
| ACTH$_{1-24}$ - NDP-α-MSH | 51 | 0.28 | 0.26 | 1.5 | 2.3 | 24 | C |
| ACTH$_{1-24}$-point-5 - NDP-α-MSH | 52 | 0.44 | 0.26 | 1.5 | 3.4 | 28 | C |

TABLE 4-continued

EC50 values for compositions of the present disclosure (* Cell pools
A and B were partially enriched for MCR expression, whereas cell pool
C was an optimized cell bank. ** ND denotes not determined)

| Description | SEQ ID NO. | MCR1 EC50 (nM) | MCR2 EC50 (nM) | MCR3 EC50 (nM) | MCR4 EC50 (nM) | MCR5 EC50 (nM) | Cell Pool* |
|---|---|---|---|---|---|---|---|
| $ACTH_{1-24}$-point-1-2-NDP-α-MSH | 53 | 0.28 | 20 | 0.72 | 1.4 | 21 | C |
| $ACTH_{1-24}$-point-3-5-NDP-α-MSH | 54 | 0.32 | 24 | 0.92 | 2.2 | 25 | C |
| $ACTH_{1-24}$-4aa-NDP-α-MSH | 55 | 0.41 | 0.13 | 0.92 | 1.9 | 9.3 | C |
| $ACTH_{1-24}$-point-5-4aa-NDP-α-MSH | 56 | 0.32 | 0.07 | 0.68 | 1.8 | 20 | C |
| $ACTH_{1-24}$-point-1-2-4aa-NDP-α-MSH | 57 | 0.25 | 4.2 | 0.42 | 1.7 | 11 | C |
| $ACTH_{1-24}$-point-3-5-4aa-NDP-α-MSH | 58 | 0.3 | 8.6 | 0.61 | 2.4 | 14 | C |
| $ACTH_{1-24}$-7aa-NDP-α-MSH | 59 | 0.24 | 0.18 | 0.85 | 1.5 | 13 | C |
| $ACTH_{1-24}$-point-5-7aa-NDP-α-MSH | 60 | 0.22 | 0.06 | 0.76 | 2.1 | 12 | C |
| $ACTH_{1-24}$-point-1-2-7aa-NDP-α-MSH | 61 | 0.3 | 4.1 | 0.47 | 2.3 | 10 | C |
| $ACTH_{1-24}$-point-3-5-7aa-NDP-α-MSH | 62 | 0.41 | 11 | 0.72 | 2.4 | 8.5 | C |
| $ACTH_{1-24}$-point-5-10aa-NDP-α-MSH | 63 | 0.69 | 0.13 | 1 | 2.8 | 11 | C |
| $ACTH_{1-24}$-point-1-2-10aa-NDP-α-MSH | 64 | 0.45 | 4.7 | 0.58 | 2.3 | 13 | C |
| $ACTH_{1-24}$-point-3-5-10aa-NDP-α-MSH | 65 | 0.78 | 15 | 1.1 | 3.8 | 16 | C |

Example 8

Administration of Compositions in Murine Air Pouch Models of Gout

An air pouch was formed by first injecting 6 mL of sterile air using a syringe filter with a 0.22 micron air filter and 23-gauge needle subcutaneously into a shaved skin site on the back of male Balb/c mice (age 6-8 weeks) on Day 0. The wounds resulting from the pouches were allowed to heal for 3 days without any intervention. The pouch was then re-inflated with 3 mL of sterile air on Day 3. Three days after re-inflation on Day 6, compositions described herein were administered via subcutaneous injection 1 hour prior to the administration of 30 mg monosodium urate crystals (MSU) directly into the air pouch to induce an inflammatory response. Four hours after injection of MSU, mice were anesthetized and exsanguinated. Exudate from the air pouch was collected by lavaging the air pouch of each animal with 3 ml of sterile PBS containing 10 Um' heparin. Analyses performed on exudates include total white cell count, differential white blood cell population, and levels of cytokines and chemokines. The following treatment groups were tested (n=8 animals per group, all animals in peptide groups were administered peptides at a dosage of 3 nmole/mouse):

1) Vehicle (PBS control, 0.2 mL/mouse)
2) $ACTH_{1-24}$, SEQ ID NO. 10
3) NDP-α-MSH, SEQ ID NO. 12
4) $ACTH_{1-24}$-linker-linker-NDP-α-MSH, SEQ ID NO. 26
5) $ACTH_{1-24}$-natural N-terminal spacer-NDP-MSH, SEQ ID NO. 39
6) $ACTH_{1-24}$-natural C-terminal spacer-NDP-MSH, SEQ ID NO. 40
7) $ACTH_{1-24}$-natural N-terminal spacer-alpha-MSH, SEQ ID NO. 42
8) $ACTH_{1-24}$-natural C-terminal spacer-alpha-MSH, SEQ ID NO. 43
9) NDP-$ACTH_{4-9}$-βAla-G-βAla-NDP-$ACTH_{4-9}$, SEQ ID NO. 44
10) NDP-$ACTH_{4-9}$-βAla-G-βAla-ACTH, SEQ ID NO. 45
11) NDP-$ACTH_{4-9}$-$ACTH_{1-24}$, SEQ ID NO. 46

Figure 10:
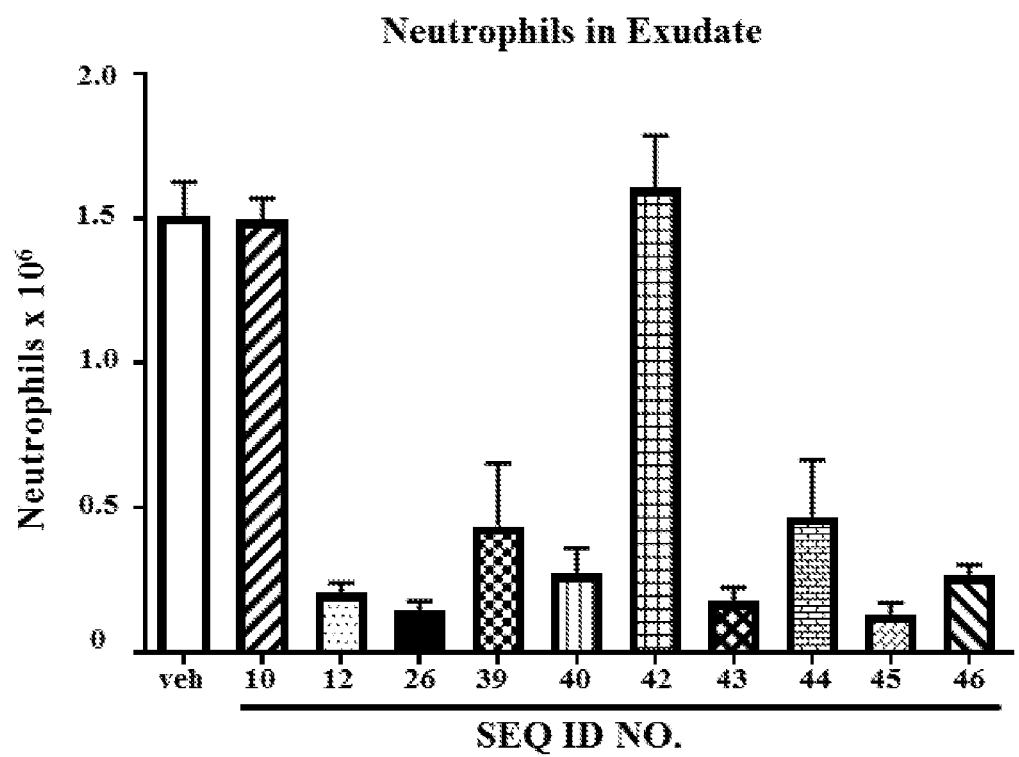
FIG. 10 shows neutrophil counts collected in exudate from murine models of gout treated with compositions disclosed herein.
Figure 11:
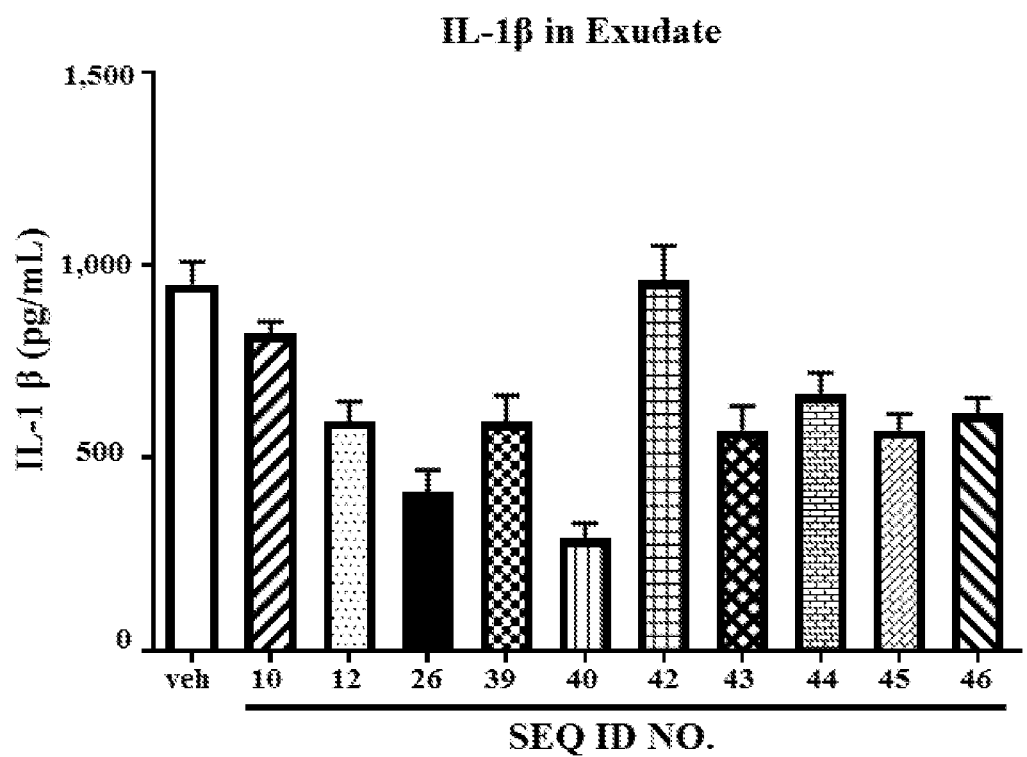
FIG. 11 shows concentrations of IL-1$\beta$ measured by ELISA in collected exudate from murine models of gout treated with compositions disclosed herein.
Figure 12A:
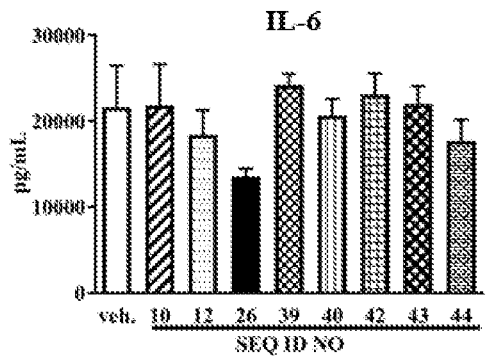
FIG. 12 shows concentrations of additional cytokines and chemokines in exudate involved in the inflammatory response as measured by Luminex (Biorad 23-Plex)
Figure 12B:
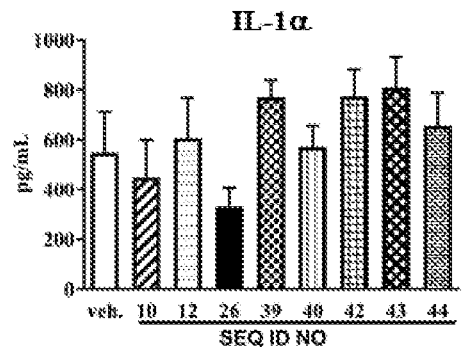
Figure 12C:
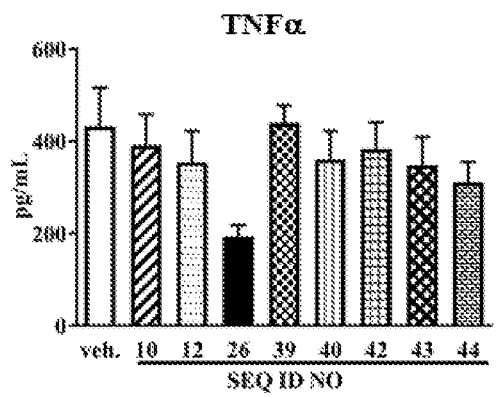
Figure 12D:
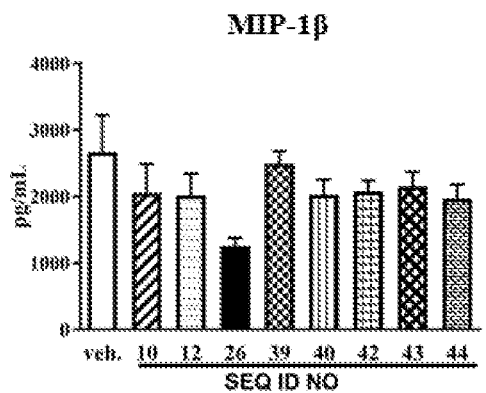
Figure 12E:
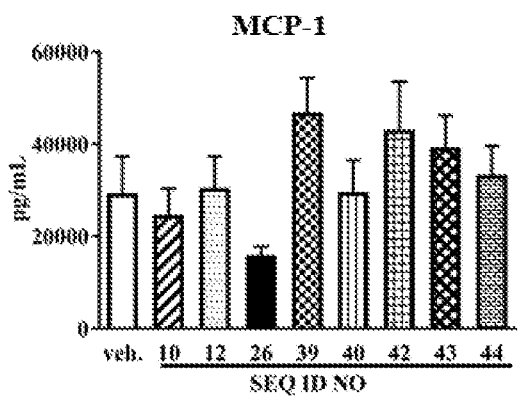
Figure 12F:
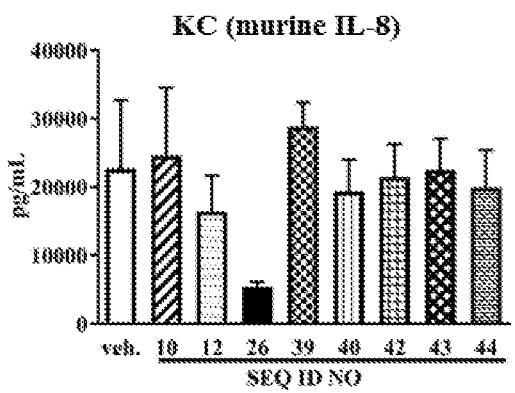
Figure 13A:
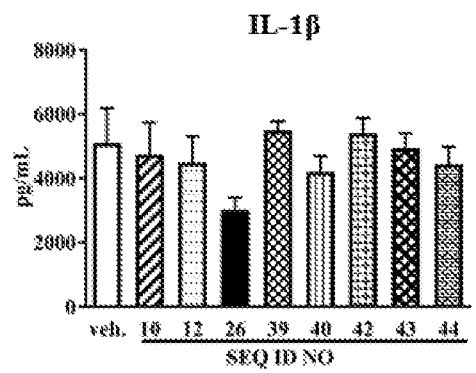
FIG. 13 shows concentrations of additional cytokines and chemokines in exudate involved in the inflammatory response as measured by Luminex (Biorad 23-Plex)
Figure 13B:
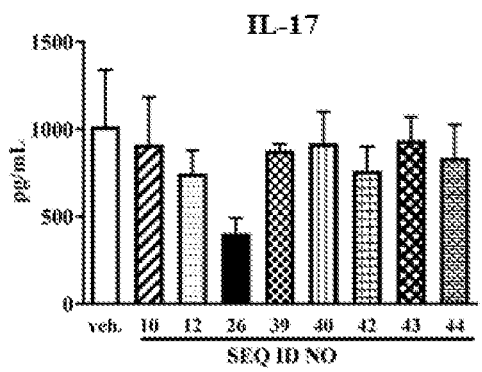
Figure 13C:
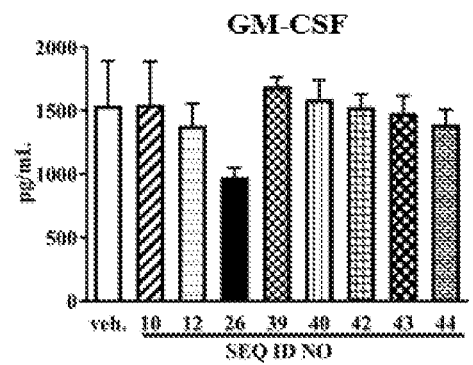
Figure 13D:
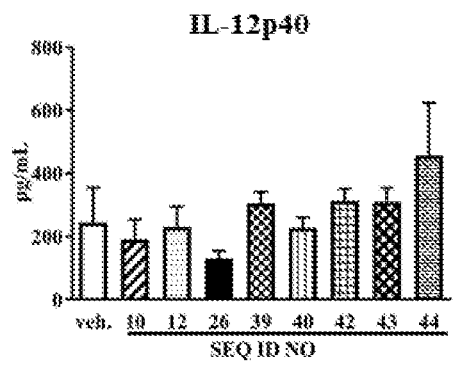
Figure 13E:
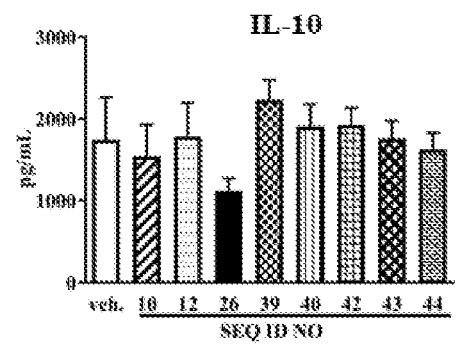

Neutrophil counts in collected exudate are shown in FIG. 10. IL-1β cytokine concentrations in collected exudate are shown in FIG. 11. Concentrations of additional cytokines and chemokines involved in the inflammatory response (e.g., IL-6 (FIG. 12A), IL-1a (FIG. 12B), TNF-α (FIG. 12C), MIP-1β (FIG. 12D), MCP-1 (FIG. 12E), and KC (murine IL-8) (FIG. 12F), IL-1β (FIG. 13A), IL-17 (FIG. 13B), GM-CSF (FIG. 13C), IL-12p40 (FIG. 13D), IL-10 (FIG. 13E)) measured by Luminex (Biorad 23-Plex) are shown in FIG. 12 and FIG. 13.

Example 9

Evaluation of Steroidogenic Effects

Compositions described herein were administered to Balb/c mice to determine the half-maximal effective concentrations for induction of corticosteroids in healthy mice. Balb/c mice were divided into 13 groups of 4 animals each (Groups 1-13), and each animal was administered a composition at a dosage as indicated in Table 5.

TABLE 5

Corticosterone Response to ACTH in Healthy Mice

| Group | No. mice | Treatment Group | Dose (µg/mouse) | Dose (nmol/mouse) | Mean corticosterone (pg/mL) | Fold change over baseline |
|---|---|---|---|---|---|---|
| 1 | 4 | PBS | 0.2 ml/mouse | 0.2 ml/mouse | | |
| 2 | 4 | SEQ ID NO. 10 | 0.009 | 0.003 | 149632 | 2.2 |
| 3 | 4 | SEQ ID NO. 10 | 0.09 | 0.03 | 336261 | 1.1 |
| 4 | 4 | SEQ ID NO. 10 | 0.9 | 0.3 | 164498 | 4.6 |
| 5 | 4 | SEQ ID NO. 10 | 2.9 | 1.0 | 690059 | 5.4 |
| 6 | 4 | SEQ ID NO. 10 | 8.8 | 3.0 | 806669 | 5.3 |
| 7 | 4 | SEQ ID NO. 10 | 29.3 | 10.0 | 799525 | 5.8 |
| 8 | 4 | SEQ ID NO. 26 | 0.015 | 0.003 | 863553 | 0.8 |
| 9 | 4 | SEQ ID NO. 26 | 0.15 | 0.03 | 116070 | 1.0 |
| 10 | 4 | SEQ ID NO. 26 | 1.5 | 0.3 | 149581 | 1.8 |
| 11 | 4 | SEQ ID NO. 26 | 5.2 | 1.0 | 264845 | 3.3 |
| 12 | 4 | SEQ ID NO. 26 | 15.5 | 3.0 | 488734 | 3.4 |
| 13 | 4 | SEQ ID NO. 26 | 51.5 | 10.0 | 514583 | 4.4 |

Each animal was injected subcutaneously at 0.2 ml/mouse as in Table 5. One hour after vehicle or test compositions were administered, the mice were anesthetized and exsanguinated into pre-chilled EDTA-treated microtainer tubes (Becton-Dickinson). The whole blood was processed to plasma and assayed by ELISA for corticosterone (Enzo Life Sciences).

Figure 14:
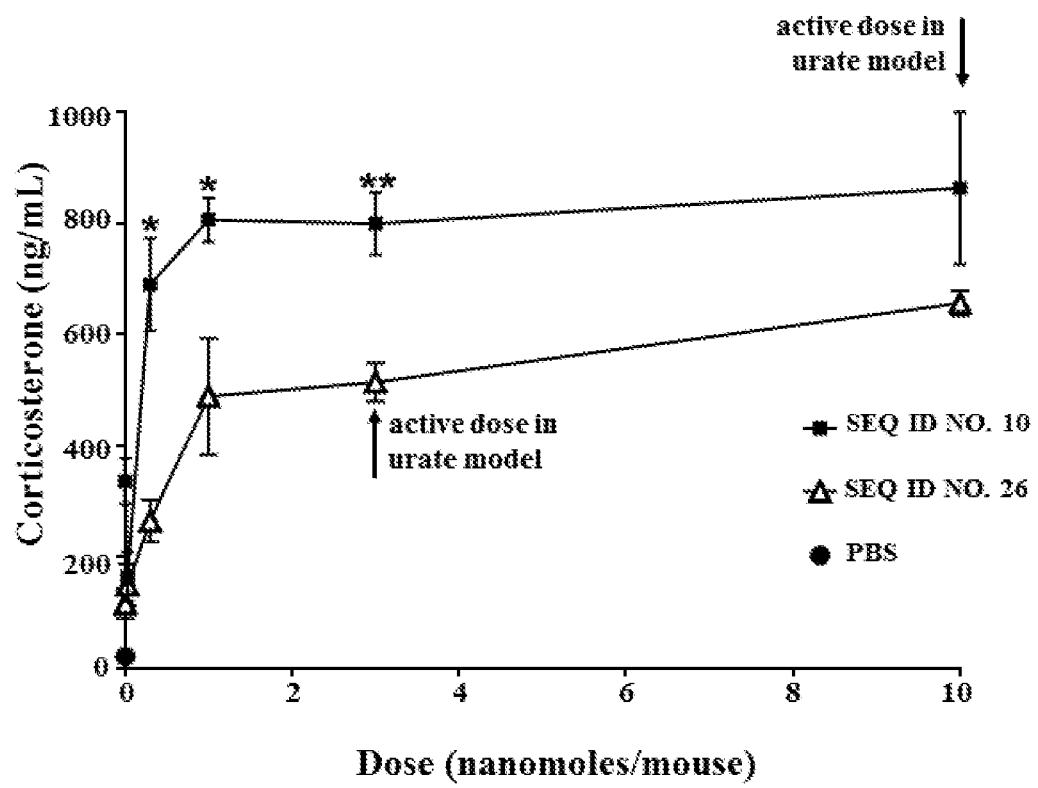
FIG. 14 shows steroid levels in Balb/c mice in response to administration of compositions disclosed herein.

As shown in FIG. 14, a single subcutaneous injection with 0.2 ml/mouse of sterile PBS resulted in a plasma corticosterone level of ~150 ng/ml. A single subcutaneous injection with 0.2 ml/mouse of SEQ ID NO. 10 resulted in a dose-dependent increase in plasma corticosterone. At 0.009 and 0.09 µg/mouse, no significant effect on plasma corticosterone was observed. At 0.9-30 µg/mouse, the plasma corticosterone levels were significantly increased, but were not significantly different from each other (~800 ng/ml). A single subcutaneous injection with 0.2 ml/mouse of SEQ ID NO. 26 resulted in a dose-dependent increase in plasma corticosterone. At 0.015, 0.15, and 1.5 µg/mouse, no significant effect on plasma corticosterone was observed. At 5.2-51.5 µg/mouse, the plasma corticosterone levels were significantly increased, but not significantly different from each other (~500 ng/ml). FIGS. 9 and 10 show that a 3 nanomole dose of SEQ ID NO. 26 was equipotent to a 10 nanomole dose of SEQ ID NO. 10 (ACTH$_{1-24}$) in decreasing inflammation in the mouse air-pouch model of gout. In this example using healthy mice, a 40% reduction in plasma corticosterone levels was observed at these equally active dose levels.

Example 10

Figure 15A:
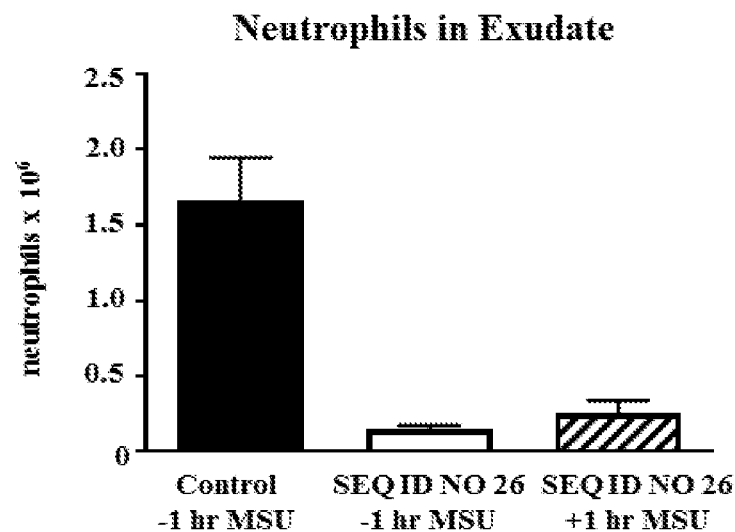
FIGS. 15A-15B shows the prophylactic and treatment effect of ACTH-linker-linker-NDP MSH (SEQ ID NO. 26) administered at 10 nmole per mouse SC at 1 hr before or 1 hour after urate injection. Exudate harvested at 4 hr after urate injection.
Figure 15B:
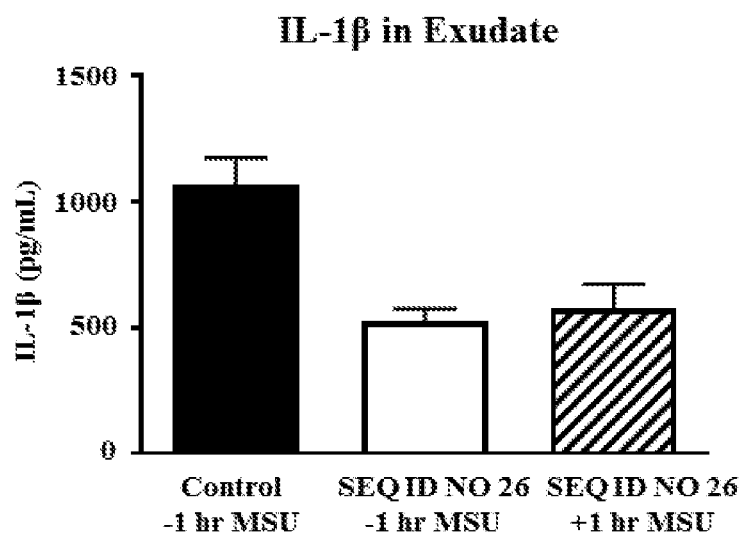

Prophylactic and Treatment Administration of Compositions in Murine Air Pouch Models of Gout An air pouch was formed by injecting 6 mL of sterile air using a syringe filter with a 0.22 micron air filter and 23-gauge needle subcutaneously into a shaved skin site on the back of male Balb/c mice (age 6-8 weeks) on Day 0. The pouches settled for 3 days to permit healing of the wound. The pouch was then re-inflated with 3 mL of sterile air on Day 3. Three days after re-inflation on Day 6, 30 mg monosodium urate crystals (MSU) directly into the air pouch to drive an inflammatory response. Compositions described herein were administered via subcutaneous injection either 1 hour prior to the administration of MSU (prevention model) or 1 hour after the administration of MSU (treatment model). Four hours after injection of MSU, mice were anesthetized and exsanguinated. Exudate from the air pouch was collected by lavaging the air pouch of each animal with 3 ml of sterile PBS containing 10 U/ml heparin. Analyses performed on exudates include total white cell count, differential white blood cell (WBC) population, and levels of cytokines and chemokines. The following treatment groups were tested:
 1) Vehicle (control)
 2) ACTH$_{1-24}$-linker-linker-NDP-α-MSH, SEQ ID NO. 26 administered at 10 nmole/mouse for individual mice at 1 hour prior to administration of MSU
 3) ACTH$_{1-24}$-linker-linker-NDP-α-MSH, SEQ ID NO. 26 administered at 10 nmole/mouse for individual mice at 1 hour after administration of MSU Total Neutrophils in collected exudate are shown in FIG. 15A. IL-1β cytokine concentrations in collected exudate are shown in FIG. 15B. SEQ ID NO. 26 significantly decreased inflammation relative to vehicle control either when administered prophylactically or as treatment after the inflammatory insult.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 11

Treatment of Infantile Spasms

An injectable formulation of ACTH$_{1-24}$—linker-linker—NDP-α-MSH (SEQ ID NO. 26) is administered via intramuscular injection to a human child subject, wherein the child is younger than two years in age. After administration, the symptoms of the infantile spasms in the subject are improved, including a reduction in the severity of the infantile spasms in the subject.

Separately, an injectable formulation of a peptide of any one of SEQ ID NOS. 1-25 or 27-72 are administered via intramuscular injection to a human child subject, wherein the child is younger than two years in age. After administration, the symptoms of the infantile spasms in the subject are improved, including a reduction in the severity of the infantile spasms in the subject.

What is claimed is:

1. A fusion polypeptide comprising:
a first polypeptide comprising a fragment of a proopiomelanocortin or a variant thereof; and
a second polypeptide comprising a fragment of a proopiomelanocortin or a variant thereof;
wherein at least one of the first polypeptide and the second polypeptide binds to a melanocortin receptor;
wherein the first polypeptide and second polypeptide are covalently linked by a peptide linker comprising (GGS)n, (GGGS)n (SEQ ID NO:89), (GGGGS)n (SEQ ID NO:90), or (GSG)n, wherein n=1-10;
wherein the variant for the first polypeptide and second polypeptide are each independently selected from an NDP variant of a fragment of proopiomelanocortin, adrenocorticotropic hormone (ACTH) comprising the amino acid substitution P19A, ACTH comprising amino acid substitutions K15A and K16A, or ACTH comprising amino acid substitutions R17A, R18A, and P19A.

2. The fusion polypeptide of claim 1, further comprising one or more additional polypeptides, wherein each additional polypeptide comprises a fragment of a proopiomelanocortin or a variant thereof,
wherein the variant is selected from an NDP variant of a fragment of proopiomelanocortin adrenocorticotropic hormone (ACTH) comprising the amino acid substitution P19A, ACTH comprising amino acid substitutions K15A and K16A, or ACTH comprising amino acid substitutions R17A, R18A, and P19A.

3. The fusion polypeptide of claim 1, wherein the first polypeptide comprises a melanocyte stimulating hormone (MSH), adrenocorticotropic hormone (ACTH), γ-lipotropin (γ-LPH), or β-endorphin.

4. The fusion polypeptide of claim 3, wherein the MSH is a MSH variant that is NDP-α-MSH.

5. The fusion polypeptide of claim 4, wherein the first polypeptide is at least 75%, 80%, 85%, 90%, 95%, or 100% identical to SEQ ID NO. 12 (NDP-α-MSH).

6. The fusion polypeptide of claim 1, wherein the first polypeptide comprises adrenocorticotropic hormone (ACTH) or a fragment thereof.

7. The fusion polypeptide of claim 6, wherein the first polypeptide is at least 75%, 80%, 85%, 90%, 95%, or 100% identical to SEQ ID NO. 10 ($ACTH_{1-24}$).

8. The fusion polypeptide of claim 6, wherein the first polypeptide is SEQ ID NO. 31.

9. The fusion polypeptide of claim 1, wherein the second polypeptide comprises an MSH, ACTH, γ-LPH, or β-endorphin.

10. The fusion polypeptide of claim 1, wherein the second polypeptide comprises adrenocorticotropic hormone (ACTH) or a fragment thereof.

11. The fusion polypeptide of claim 1, wherein the fusion polypeptide has an arrangement of formula (I):

first polypeptide—linker—second polypeptide    Formula (I).

12. The fusion polypeptide of claim 1, wherein the fusion polypeptide has an arrangement of formula (II):

second polypeptide —linker —first polypeptide    Formula (II).

13. The fusion polypeptide of claim 1, wherein the fusion polypeptide is at least 75%, 80%, 85%, 90%, 95%, of 100% identical to SEQ ID NO. 21, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 32, SEQ ID NO. 38, SEQ ID NO. 41, SEQ ID NO. 55, SEQ ID NO. 56, SEQ ID NO. 57, SEQ ID NO. 58, SEQ ID NO. 59, SEQ ID NO. 60, SEQ ID NO. 61, SEQ ID NO. 62, SEQ ID NO. 63, SEQ ID NO. 64, or SEQ ID NO. 65.

14. The fusion polypeptide of claim 9, wherein the MSH is a MSH variant that is NDP-α-MSH.

15. The fusion polypeptide of claim 14, wherein the second polypeptide is at least 75%, 80%, 85%, 90%, 95%, or 100% identical to SEQ ID NO. 12 (NDP-α-MSH).

16. The fusion polypeptide of claim 1, wherein the peptide linker covalently linking the first polypeptide and the second polypeptide is selected from GGGGS (SEQ ID NO:90), GGGGSGGGGS (SEQ ID NO:80), GGGS (SEQ ID NO:89), GGGGSGG (SEQ ID NO:93), or GGSGGSGGS (SEQ ID NO:94).

17. The fusion polypeptide of claim 1, wherein the linker peptide further comprises a cleavage site.

18. The fusion polypeptide of claim 17, wherein the cleavage site is cleavable by a protease.

19. The fusion polypeptide of claim 18, wherein the protease is a metalloproteinase, a proconvertase, a cathepsin, or an endoprotease.

20. The fusion polypeptide of claim 1, wherein the first polypeptide, second polypeptide, or both first and second polypeptides are acetylated.

21. The fusion protein of claim 1, wherein the first polypeptide comprises SEQ ID NO. 10 ($ACTH_{1-24}$), the second polypeptide comprises SEQ ID NO. 12 (NDP-α-MSH), and the linker comprises GGGGSGGGGS (SEQ ID NO:80).

22. The fusion polypeptide of claim 21, wherein the fusion polypeptide has the amino acid sequence of SEQ ID NO. 26.

* * * * *

```
                           SEQUENCE LISTING

<160> NUMBER OF SEQ ID NOS: 94

<210> SEQ ID NO 1
<211> LENGTH: 38
<212> TYPE: PRT
<213> ORGANISM: Artificial Sequence
<220> FEATURE:
<223> OTHER INFORMATION: Synthetic: Gamma-MSH  ACTH1-24

<400> SEQUENCE: 1

Tyr Val Met Gly His Phe Arg Trp Asp Arg Phe Gly Lys Arg Ser Tyr
1               5                   10                  15

Ser Met Glu His Phe Arg Trp Gly Lys Pro Val Gly Lys Lys Arg Arg
            20                  25                  30

Pro Val Lys Val Tyr Pro
        35

<210> SEQ ID NO 2
<211> LENGTH: 52
<212> TYPE: PRT
<213> ORGANISM: Artificial Sequence
<220> FEATURE:
<223> OTHER INFORMATION: Synthetic: Gamma-MSH  ACTH1-24 with natural
      linker

<400> SEQUENCE: 2

Tyr Val Met Gly His Phe Arg Trp Asp Arg Phe Gly Arg Arg Asn Ser
1               5                   10                  15

Ser Ser Ser Gly Ser Ser Gly Ala Gly Gln Lys Arg Ser Tyr Ser Met
            20                  25                  30

Glu His Phe Arg Trp Gly Lys Pro Val Gly Lys Lys Arg Arg Pro Val
        35                  40                  45

Lys Val Tyr Pro
    50

<210> SEQ ID NO 3
<211> LENGTH: 38
<212> TYPE: PRT
<213> ORGANISM: Artificial Sequence
<220> FEATURE:
<223> OTHER INFORMATION: Synthetic: NDP-Gamma-MSH  ACTH1-24
<220> FEATURE:
<221> NAME/KEY: misc_feature
<222> LOCATION: (3)..(3)
<223> OTHER INFORMATION: Xaa is Nle (norleucine)
<220> FEATURE:
<221> NAME/KEY: misc_feature
<222> LOCATION: (6)..(6)
<223> OTHER INFORMATION: Xaa is DPhe (D-phenylalanine)

<400> SEQUENCE: 3

Tyr Val Xaa Gly His Xaa Arg Trp Asp Arg Phe Gly Lys Arg Ser Tyr
1               5                   10                  15

Ser Met Glu His Phe Arg Trp Gly Lys Pro Val Gly Lys Lys Arg Arg
            20                  25                  30

Pro Val Lys Val Tyr Pro
```

<210> SEQ ID NO 4
<211> LENGTH: 27
<212> TYPE: PRT
<213> ORGANISM: Artificial Sequence
<220> FEATURE:
<223> OTHER INFORMATION: Synthetic: Gamma-MSH Alpha-MSH
<220> FEATURE:
<221> NAME/KEY: misc_feature
<223> OTHER INFORMATION: NH2 at 3' end

<400> SEQUENCE: 4

Tyr Val Met Gly His Phe Arg Trp Asp Arg Phe Gly Lys Arg Ser Tyr
1               5                   10                  15

Ser Met Glu His Phe Arg Trp Gly Lys Pro Val
            20                  25

<210> SEQ ID NO 5
<211> LENGTH: 41
<212> TYPE: PRT
<213> ORGANISM: Artificial Sequence
<220> FEATURE:
<223> OTHER INFORMATION: Synthetic: Gamma-MSH Alpha-MSH with natural
      linker
<220> FEATURE:
<221> NAME/KEY: misc_feature
<223> OTHER INFORMATION: NH2 at 3' end

<400> SEQUENCE: 5

Tyr Val Met Gly His Phe Arg Trp Asp Arg Phe Gly Arg Arg Asn Ser
1               5                   10                  15

Ser Ser Ser Gly Ser Ser Gly Ala Gly Gln Lys Arg Ser Tyr Ser Met
            20                  25                  30

Glu His Phe Arg Trp Gly Lys Pro Val
            35                  40

<210> SEQ ID NO 6
<211> LENGTH: 27
<212> TYPE: PRT
<213> ORGANISM: Artificial Sequence
<220> FEATURE:
<223> OTHER INFORMATION: Synthetic: NDP-Gamma-MSH Alpha-MSH
<220> FEATURE:
<221> NAME/KEY: misc_feature
<223> OTHER INFORMATION: NH2 at 3' end
<220> FEATURE:
<221> NAME/KEY: misc_feature
<222> LOCATION: (3)..(3)
<223> OTHER INFORMATION: Xaa is Nle (norleucine)
<220> FEATURE:
<221> NAME/KEY: misc_feature
<222> LOCATION: (6)..(6)
<223> OTHER INFORMATION: Xaa is DPhe (D-phenylalanine)

<400> SEQUENCE: 6

Tyr Val Xaa Gly His Xaa Arg Trp Asp Arg Phe Gly Lys Arg Ser Tyr
1               5                   10                  15

Ser Met Glu His Phe Arg Trp Gly Lys Pro Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic: Gamma-MSH NDP-Alpha-MSH
<220> FEATURE:

```
<221> NAME/KEY: misc_feature
<223> OTHER INFORMATION: NH2 at 3' end
<220> FEATURE:
<221> NAME/KEY: misc_feature
<222> LOCATION: (18)..(18)
<223> OTHER INFORMATION: Xaa is Nle (norleucine)
<220> FEATURE:
<221> NAME/KEY: misc_feature
<222> LOCATION: (21)..(21)
<223> OTHER INFORMATION: Xaa is DPhe (D-phenylalanine)

<400> SEQUENCE: 7

Tyr Val Met Gly His Phe Arg Trp Asp Arg Phe Gly Lys Arg Ser Tyr
1               5                   10                  15

Ser Xaa Glu His Xaa Arg Trp Gly Lys Pro Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic: NDP-Gamma-MSH  NDP-Alpha-MSH
<220> FEATURE:
<221> NAME/KEY: misc_feature
<223> OTHER INFORMATION: NH2 at 3' end
<220> FEATURE:
<221> NAME/KEY: misc_feature
<222> LOCATION: (3)..(3)
<223> OTHER INFORMATION: Xaa is Nle (norleucine)
<220> FEATURE:
<221> NAME/KEY: misc_feature
<222> LOCATION: (6)..(6)
<223> OTHER INFORMATION: Xaa is DPhe (D-phenylalanine)
<220> FEATURE:
<221> NAME/KEY: misc_feature
<222> LOCATION: (18)..(18)
<223> OTHER INFORMATION: Xaa is Nle (norleucine)
<220> FEATURE:
<221> NAME/KEY: misc_feature
<222> LOCATION: (21)..(21)
<223> OTHER INFORMATION: Xaa is DPhe (D-phenylalanine)

<400> SEQUENCE: 8

Tyr Val Xaa Gly His Xaa Arg Trp Asp Arg Phe Gly Lys Arg Ser Tyr
1               5                   10                  15

Ser Xaa Glu His Xaa Arg Trp Gly Lys Pro Val
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic: Gamma-MSH with linker

<400> SEQUENCE: 9

Tyr Val Met Gly His Phe Arg Trp Asp Arg Phe Gly Arg Arg Asn Ser
1               5                   10                  15

Ser Ser Ser Gly Ser Ser Gly Ala Gly Gln Lys Arg
            20                  25

<210> SEQ ID NO 10
<211> LENGTH: 24
<212> TYPE: PRT
<213> ORGANISM: Artificial Sequence
<220> FEATURE:
<223> OTHER INFORMATION: Synthetic: ACTH1-24

<400> SEQUENCE: 10
```

```
Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 11
<211> LENGTH: 13
<212> TYPE: PRT
<213> ORGANISM: Artificial Sequence
<220> FEATURE:
<223> OTHER INFORMATION: Synthetic: Alpha-MSH
<220> FEATURE:
<221> NAME/KEY: misc_feature
<223> OTHER INFORMATION: NH2 at 3' end

<400> SEQUENCE: 11

Ser Tyr Ser Met Glu His Phe Arg Trp Gly Lys Pro Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic: NDP-Alpha-MSH
<220> FEATURE:
<221> NAME/KEY: misc_feature
<223> OTHER INFORMATION: NH2 at 3' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 12

Ser Tyr Ser Xaa Glu His Xaa Arg Trp Gly Lys Pro Val
1               5                   10

<210> SEQ ID NO 13
<211> LENGTH: 55
<212> TYPE: PRT
<213> ORGANISM: Artificial Sequence
<220> FEATURE:
<223> OTHER INFORMATION: Synthetic: Gamma-MSH  ACTH1-39 without linker

<400> SEQUENCE: 13

Tyr Val Met Gly His Phe Arg Trp Asp Arg Phe Gly Lys Arg Ser Tyr
1               5                   10                  15

Ser Met Glu His Phe Arg Trp Gly Lys Pro Val Gly Lys Lys Arg Arg
            20                  25                  30

Pro Val Lys Val Tyr Pro Asn Gly Ala Glu Asp Glu Ser Ala Glu Ala
        35                  40                  45

Phe Pro Leu Glu Phe Lys Arg
    50                  55

<210> SEQ ID NO 14
<211> LENGTH: 50
<212> TYPE: PRT
<213> ORGANISM: Artificial Sequence
<220> FEATURE:
<223> OTHER INFORMATION: Synthetic: Gamma-MSH  ACTH1-24 linker without
      cleavable site

<400> SEQUENCE: 14
```

```
Tyr Val Met Gly His Phe Arg Trp Asp Arg Phe Gly Arg Arg Asn Ser
1               5                   10                  15

Ser Ser Ser Gly Ser Gly Ala Gly Gln Ser Tyr Ser Met Glu His
            20              25                  30

Phe Arg Trp Gly Lys Pro Val Gly Lys Lys Arg Arg Pro Val Lys Val
        35                  40                  45

Tyr Pro
    50

<210> SEQ ID NO 15
<211> LENGTH: 36
<212> TYPE: PRT
<213> ORGANISM: Artificial Sequence
<220> FEATURE:
<223> OTHER INFORMATION: Synthetic: Gamma-MSH  ACTH1-24 without linker
      and cleavage site

<400> SEQUENCE: 15

Tyr Val Met Gly His Phe Arg Trp Asp Arg Phe Gly Ser Tyr Ser Met
1               5                   10                  15

Glu His Phe Arg Trp Gly Lys Pro Val Gly Lys Lys Arg Arg Pro Val
            20                  25                  30

Lys Val Tyr Pro
        35

<210> SEQ ID NO 16
<211> LENGTH: 31
<212> TYPE: PRT
<213> ORGANISM: Artificial Sequence
<220> FEATURE:
<223> OTHER INFORMATION: Synthetic: Beta--endorphin

<400> SEQUENCE: 16

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 17
<211> LENGTH: 22
<212> TYPE: PRT
<213> ORGANISM: Artificial Sequence
<220> FEATURE:
<223> OTHER INFORMATION: Synthetic: Beta--MSH

<400> SEQUENCE: 17

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 18
<211> LENGTH: 12
<212> TYPE: PRT
<213> ORGANISM: Artificial Sequence
<220> FEATURE:
<223> OTHER INFORMATION: Synthetic: NDP-Gamma-MSH
<220> FEATURE:
<221> NAME/KEY: misc_feature
<222> LOCATION: (3)..(3)
<223> OTHER INFORMATION: Xaa is Nle (norleucine)
<220> FEATURE:
<221> NAME/KEY: misc_feature
<222> LOCATION: (6)..(6)
```

-continued

<223> OTHER INFORMATION: Xaa is DPhe (D-phenylalanine)

<400> SEQUENCE: 18

Tyr Val Xaa Gly His Xaa Arg Trp Asp Arg Phe Gly
1               5                   10

<210> SEQ ID NO 19
<211> LENGTH: 41
<212> TYPE: PRT
<213> ORGANISM: Artificial Sequence
<220> FEATURE:
<223> OTHER INFORMATION: Synthetic: ACTH1-39

<400> SEQUENCE: 19

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe Lys Arg
        35                  40

<210> SEQ ID NO 20
<211> LENGTH: 12
<212> TYPE: PRT
<213> ORGANISM: Artificial Sequence
<220> FEATURE:
<223> OTHER INFORMATION: Synthetic: Gamma-MSH

<400> SEQUENCE: 20

Tyr Val Met Gly His Phe Arg Trp Asp Arg Phe Gly
1               5                   10

<210> SEQ ID NO 21
<211> LENGTH: 290
<212> TYPE: PRT
<213> ORGANISM: Artificial Sequence
<220> FEATURE:
<223> OTHER INFORMATION: Synthetic: Delta POMC glycopolymer

<400> SEQUENCE: 21

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe Lys Arg Glu Leu Thr Gly Gln Arg Leu
        35                  40                  45

Arg Glu Gly Asp Gly Pro Asp Gly Pro Ala Asp Asp Gly Ala Gly Ala
    50                  55                  60

Gln Ala Asp Leu Glu His Ser Leu Leu Val Ala Ala Glu Lys Lys Asp
65                  70                  75                  80

Glu Gly Pro Tyr Arg Met Glu His Phe Arg Trp Gly Ser Pro Pro Lys
                85                  90                  95

Asp Lys Arg Tyr Gly Gly Phe Met Gly Gly Ser Gly Gly Ser Gly Gly
            100                 105                 110

Ser Asn Asn Thr Gly Gly Ser Gly Gly Ser Gly Gly Ser Asn Asn Thr
        115                 120                 125

Gly Gly Ser Gly Gly Ser Gly Gly Ser Asn Asn Thr Gly Gly Ser Gly
    130                 135                 140

Gly Ser Gly Gly Ser Asn Asn Thr Gly Gly Ser Gly Gly Ser Gly Gly
145                 150                 155                 160

```
Ser Asn Asn Thr Gly Gly Ser Gly Gly Ser Gly Gly Ser Asn Asn Thr
                165                 170                 175

Gly Gly Ser Gly Gly Ser Gly Gly Ser Asn Asn Thr Gly Gly Ser Gly
            180                 185                 190

Gly Ser Gly Gly Ser Asn Asn Thr Gly Gly Ser Gly Gly Ser Gly Gly
        195                 200                 205

Ser Asn Asn Thr Gly Gly Ser Gly Gly Ser Gly Gly Ser Asn Asn Thr
    210                 215                 220

Gly Gly Ser Gly Gly Ser Gly Gly Ser Asn Asn Thr Gly Gly Ser Gly
225                 230                 235                 240

Gly Ser Gly Gly Ser Asn Asn Thr Gly Gly Ser Gly Gly Ser Gly Gly
        245                 250                 255

Ser Asn Asn Thr Gly Gly Ser Gly Gly Ser Gly Gly Ser Asn Asn Thr
    260                 265                 270

Gly Gly Ser Gly Gly Ser Gly Gly Ser Asn Asn Thr Gly Gly Ser Gly
            275                 280                 285

Gly Ser
    290

<210> SEQ ID NO 22
<211> LENGTH: 184
<212> TYPE: PRT
<213> ORGANISM: Artificial Sequence
<220> FEATURE:
<223> OTHER INFORMATION: Synthetic: Gamma-MSH  ACTH1-39 fusion protein

<400> SEQUENCE: 22

Glu Val Arg Gly Trp Cys Leu Glu Ser Ser Gln Cys Gln Asp Leu Thr
1               5                   10                  15

Thr Glu Ser Asn Leu Leu Glu Cys Ile Arg Ala Cys Lys Pro Asp Leu
            20                  25                  30

Ser Ala Glu Thr Pro Met Phe Pro Gly Asn Gly Asp Glu Gln Pro Leu
        35                  40                  45

Thr Glu Asn Pro Arg Lys Tyr Val Met Gly His Phe Arg Trp Asp Arg
    50                  55                  60

Phe Gly Arg Arg Asn Ser Ser Ser Gly Ser Ser Gly Ala Gly Gln
65                  70                  75                  80

Lys Arg Glu Asp Val Ser Ala Gly Glu Asp Cys Gly Pro Leu Pro Glu
                85                  90                  95

Gly Gly Pro Glu Pro Arg Ser Asp Gly Ala Lys Pro Gly Pro Arg Glu
            100                 105                 110

Gly Lys Arg Ser Tyr Ser Met Glu His Phe Arg Trp Gly Lys Pro Val
        115                 120                 125

Gly Lys Lys Arg Arg Pro Val Lys Val Tyr Pro Asn Gly Ala Glu Asp
130                 135                 140

Glu Ser Ala Glu Ala Phe Pro Leu Glu Phe Lys Arg Ala Glu Lys Lys
145                 150                 155                 160

Asp Glu Gly Pro Tyr Arg Met Glu His Phe Arg Trp Gly Ser Pro Pro
                165                 170                 175

Lys Asp Gly Gly Ser Gly Gly Ser
            180

<210> SEQ ID NO 23
<211> LENGTH: 47
<212> TYPE: PRT
<213> ORGANISM: Artificial Sequence
<220> FEATURE:
```

```
<223> OTHER INFORMATION: Synthetic: NDP-Alpha-MSH  linker-linker
      ACTH1-24
<220> FEATURE:
<221> NAME/KEY: misc_feature
<223> OTHER INFORMATION: Acetylation on 5' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 23

Ser Tyr Ser Xaa Glu His Xaa Arg Trp Gly Lys Pro Val Gly Gly Gly
1               5                   10                  15

Gly Ser Gly Gly Gly Gly Ser Ser Tyr Ser Met Glu His Phe Arg Trp
            20                  25                  30

Gly Lys Pro Val Gly Lys Lys Arg Arg Pro Val Lys Val Tyr Pro
        35                  40                  45

<210> SEQ ID NO 24
<211> LENGTH: 51
<212> TYPE: PRT
<213> ORGANISM: Artificial Sequence
<220> FEATURE:
<223> OTHER INFORMATION: Synthetic: NDP-Alpha-MSH  linker-Furin
      site-linker  ACTH1-24
<220> FEATURE:
<221> NAME/KEY: misc_feature
<223> OTHER INFORMATION: Acetylation on 5' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 24

Ser Tyr Ser Xaa Glu His Xaa Arg Trp Gly Lys Pro Val Gly Gly Gly
1               5                   10                  15

Gly Ser Arg Arg Lys Arg Gly Gly Gly Ser Ser Tyr Ser Met Glu
            20                  25                  30

His Phe Arg Trp Gly Lys Pro Val Gly Lys Lys Arg Arg Pro Val Lys
            35                  40                  45

Val Tyr Pro
    50

<210> SEQ ID NO 25
<211> LENGTH: 53
<212> TYPE: PRT
<213> ORGANISM: Artificial Sequence
<220> FEATURE:
<223> OTHER INFORMATION: Synthetic: NDP-Alpha-MSH  linker-MMP
      site-linker  ACTH1-24
<220> FEATURE:
<221> NAME/KEY: misc_feature
<223> OTHER INFORMATION: Acetylation on 5' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)
```

-continued

<400> SEQUENCE: 25

Ser Tyr Ser Xaa Glu His Xaa Arg Trp Gly Lys Pro Val Gly Gly
1               5                   10                  15

Gly Ser Pro Leu Gly Leu Trp Ala Gly Gly Gly Ser Ser Tyr Ser
            20                  25                  30

Met Glu His Phe Arg Trp Gly Lys Pro Val Gly Lys Lys Arg Arg Pro
        35                  40                  45

Val Lys Val Tyr Pro
    50

<210> SEQ ID NO 26
<211> LENGTH: 47
<212> TYPE: PRT
<213> ORGANISM: Artificial Sequence
<220> FEATURE:
<223> OTHER INFORMATION: Synthetic: ACTH1-24 linker-linker
      NDP-Alpha-MSH
<220> FEATURE:
<221> NAME/KEY: misc_feature
<222> LOCATION: (38)..(38)
<223> OTHER INFORMATION: Xaa is Nle (norleucine)
<220> FEATURE:
<221> NAME/KEY: misc_feature
<222> LOCATION: (41)..(41)
<223> OTHER INFORMATION: Xaa is DPhe (D-phenylalanine)

<400> SEQUENCE: 26

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Gly Ser Gly Gly Gly
            20                  25                  30

Gly Ser Ser Tyr Ser Xaa Glu His Xaa Arg Trp Gly Lys Pro Val
        35                  40                  45

<210> SEQ ID NO 27
<211> LENGTH: 51
<212> TYPE: PRT
<213> ORGANISM: Artificial Sequence
<220> FEATURE:
<223> OTHER INFORMATION: Synthetic: ACTH1-24 linker-Furin site-linker
      NDP-Alpha-MSH
<220> FEATURE:
<221> NAME/KEY: misc_feature
<222> LOCATION: (42)..(42)
<223> OTHER INFORMATION: Xaa is Nle (norleucine)
<220> FEATURE:
<221> NAME/KEY: misc_feature
<222> LOCATION: (45)..(45)
<223> OTHER INFORMATION: Xaa is DPhe (D-phenylalanine)

<400> SEQUENCE: 27

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Gly Ser Arg Arg Lys
            20                  25                  30

Arg Gly Gly Gly Gly Ser Ser Tyr Ser Xaa Glu His Xaa Arg Trp Gly
        35                  40                  45

Lys Pro Val
    50

<210> SEQ ID NO 28
<211> LENGTH: 53
<212> TYPE: PRT
<213> ORGANISM: Artificial Sequence
<220> FEATURE:

```
<223> OTHER INFORMATION: Synthetic: ACTH1-24  linker-MMP site-linker
      NDP-Alpha-MSH
<220> FEATURE:
<221> NAME/KEY: misc_feature
<222> LOCATION: (44)..(44)
<223> OTHER INFORMATION: Xaa is Nle (norleucine)
<220> FEATURE:
<221> NAME/KEY: misc_feature
<222> LOCATION: (47)..(47)
<223> OTHER INFORMATION: Xaa is DPhe (D-phenylalanine)

<400> SEQUENCE: 28

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Pro Leu Gly
            20                  25                  30

Leu Trp Ala Gly Gly Gly Gly Ser Ser Tyr Ser Xaa Glu His Xaa Arg
        35                  40                  45

Trp Gly Lys Pro Val
        50

<210> SEQ ID NO 29
<211> LENGTH: 53
<212> TYPE: PRT
<213> ORGANISM: Artificial Sequence
<220> FEATURE:
<223> OTHER INFORMATION: Synthetic: ACTH1-24  linker-MMP (broad)
      site-linker NDP-Alpha-MSH
<220> FEATURE:
<221> NAME/KEY: misc_feature
<222> LOCATION: (44)..(44)
<223> OTHER INFORMATION: Xaa is Nle (norleucine)
<220> FEATURE:
<221> NAME/KEY: misc_feature
<222> LOCATION: (47)..(47)
<223> OTHER INFORMATION: Xaa is DPhe (D-phenylalanine)

<400> SEQUENCE: 29

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Pro Ala Gly
            20                  25                  30

Leu Val Ala Gly Gly Gly Gly Ser Ser Tyr Ser Xaa Glu His Xaa Arg
        35                  40                  45

Trp Gly Lys Pro Val
        50

<210> SEQ ID NO 30
<211> LENGTH: 6
<212> TYPE: PRT
<213> ORGANISM: Artificial Sequence
<220> FEATURE:
<223> OTHER INFORMATION: Synthetic: ACTH4-9

<400> SEQUENCE: 30

Met Glu His Phe Arg Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic: NDP-ACTH4-9
<220> FEATURE:
<221> NAME/KEY: misc_feature
<222> LOCATION: (1)..(1)
```

```
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)

<400> SEQUENCE: 31

Xaa Glu His Xaa Arg Trp
1               5

<210> SEQ ID NO 32
<211> LENGTH: 53
<212> TYPE: PRT
<213> ORGANISM: Artificial Sequence
<220> FEATURE:
<223> OTHER INFORMATION: Synthetic: NDP-Alpha-MSH  linker-MMP (broad)
      site-linker ACTH1-24
<220> FEATURE:
<221> NAME/KEY: misc_feature
<223> OTHER INFORMATION: Acetylation on 5' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 32

Ser Tyr Ser Xaa Glu His Xaa Arg Trp Gly Lys Pro Val Gly Gly Gly
1               5                   10                  15

Gly Ser Pro Ala Gly Leu Val Ala Gly Gly Gly Gly Ser Ser Tyr Ser
            20                  25                  30

Met Glu His Phe Arg Trp Gly Lys Pro Val Gly Lys Lys Arg Arg Pro
        35                  40                  45

Val Lys Val Tyr Pro
    50

<210> SEQ ID NO 33
<211> LENGTH: 13
<212> TYPE: PRT
<213> ORGANISM: Artificial Sequence
<220> FEATURE:
<223> OTHER INFORMATION: Synthetic: Acetylated Alpha-MSH
<220> FEATURE:
<221> NAME/KEY: misc_feature
<223> OTHER INFORMATION: Acetylation on 5' end and NH2 on 3' end

<400> SEQUENCE: 33

Ser Tyr Ser Met Glu His Phe Arg Trp Gly Lys Pro Val
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic: HFRWKPV-NH2
<220> FEATURE:
<221> NAME/KEY: misc_feature
<223> OTHER INFORMATION: NH2 at 3' end

<400> SEQUENCE: 34

His Phe Arg Trp Lys Pro Val
1               5

<210> SEQ ID NO 35
```

```
<211> LENGTH: 4
<212> TYPE: PRT
<213> ORGANISM: Artificial Sequence
<220> FEATURE:
<223> OTHER INFORMATION: Synthetic: HFRW

<400> SEQUENCE: 35

His Phe Arg Trp
1

<210> SEQ ID NO 36
<211> LENGTH: 3
<212> TYPE: PRT
<213> ORGANISM: Artificial Sequence
<220> FEATURE:
<223> OTHER INFORMATION: Synthetic: KPV-NH2
<220> FEATURE:
<221> NAME/KEY: misc_feature
<223> OTHER INFORMATION: NH2 at 3' end

<400> SEQUENCE: 36

Lys Pro Val
1

<210> SEQ ID NO 37
<211> LENGTH: 7
<212> TYPE: PRT
<213> ORGANISM: Artificial Sequence
<220> FEATURE:
<223> OTHER INFORMATION: Synthetic: KPVHFRW

<400> SEQUENCE: 37

Lys Pro Val His Phe Arg Trp
1               5

<210> SEQ ID NO 38
<211> LENGTH: 46
<212> TYPE: PRT
<213> ORGANISM: Artificial Sequence
<220> FEATURE:
<223> OTHER INFORMATION: Synthetic: ACTH1-24  proconvertase
      NDP-Alpha-MSH
<220> FEATURE:
<221> NAME/KEY: misc_feature
<222> LOCATION: (37)..(37)
<223> OTHER INFORMATION: Xaa is Nle (norleucine)
<220> FEATURE:
<221> NAME/KEY: misc_feature
<222> LOCATION: (40)..(40)
<223> OTHER INFORMATION: Xaa is DPhe (D-phenylalanine)

<400> SEQUENCE: 38

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Arg Arg Lys
            20                  25                  30

Arg Ser Tyr Ser Xaa Glu His Xaa Arg Trp Gly Lys Pro Val
            35                  40                  45

<210> SEQ ID NO 39
<211> LENGTH: 60
<212> TYPE: PRT
<213> ORGANISM: Artificial Sequence
<220> FEATURE:
<223> OTHER INFORMATION: Synthetic: ACTH1-24  natural N-terminal spacer
      NDP-Alpha-MSH
<220> FEATURE:
<221> NAME/KEY: misc_feature
<222> LOCATION: (51)..(51)
```

<223> OTHER INFORMATION: Xaa is Nle (norleucine)
<220> FEATURE:
<221> NAME/KEY: misc_feature
<222> LOCATION: (54)..(54)
<223> OTHER INFORMATION: Xaa is DPhe (D-phenylalanine)

<400> SEQUENCE: 39

Ser Tyr Ser Met Glu His Phe Arg Trp Gly Lys Pro Val Gly Lys Lys
1               5                   10                  15

Arg Arg Pro Val Lys Val Tyr Pro Pro Leu Pro Glu Gly Gly Pro Glu
            20                  25                  30

Pro Arg Ser Asp Gly Ala Lys Pro Gly Pro Arg Glu Gly Lys Arg Ser
        35                  40                  45

Tyr Ser Xaa Glu His Xaa Arg Trp Gly Lys Pro Val
    50                  55                  60

<210> SEQ ID NO 40
<211> LENGTH: 60
<212> TYPE: PRT
<213> ORGANISM: Artificial Sequence
<220> FEATURE:
<223> OTHER INFORMATION: Synthetic: ACTH1-24  natural C-terminal spacer
      NDP-Alpha-MSH
<220> FEATURE:
<221> NAME/KEY: misc_feature
<222> LOCATION: (51)..(51)
<223> OTHER INFORMATION: Xaa is Nle (norleucine)
<220> FEATURE:
<221> NAME/KEY: misc_feature
<222> LOCATION: (54)..(54)
<223> OTHER INFORMATION: Xaa is DPhe (D-phenylalanine)

<400> SEQUENCE: 40

Ser Tyr Ser Met Glu His Phe Arg Trp Gly Lys Pro Val Gly Lys Lys
1               5                   10                  15

Arg Arg Pro Val Lys Val Tyr Pro Glu Leu Thr Gly Gln Arg Leu Arg
            20                  25                  30

Glu Gly Asp Gly Pro Asp Gly Pro Ala Asp Asp Gly Ala Gly Ala Ser
        35                  40                  45

Tyr Ser Xaa Glu His Xaa Arg Trp Gly Lys Pro Val
    50                  55                  60

<210> SEQ ID NO 41
<211> LENGTH: 46
<212> TYPE: PRT
<213> ORGANISM: Artificial Sequence
<220> FEATURE:
<223> OTHER INFORMATION: Synthetic: ACTH1-24  proconvertase  Alpha-MSH

<400> SEQUENCE: 41

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Arg Arg Lys
            20                  25                  30

Arg Ser Tyr Ser Met Glu His Phe Arg Trp Gly Lys Pro Val
        35                  40                  45

<210> SEQ ID NO 42
<211> LENGTH: 60
<212> TYPE: PRT
<213> ORGANISM: Artificial Sequence
<220> FEATURE:
<223> OTHER INFORMATION: Synthetic: ACTH1-24  natural N-terminal spacer
      Alpha-MSH

<400> SEQUENCE: 42

Ser Tyr Ser Met Glu His Phe Arg Trp Gly Lys Pro Val Gly Lys Lys
1               5                   10                  15

Arg Arg Pro Val Lys Val Tyr Pro Pro Leu Pro Glu Gly Gly Pro Glu
            20                  25                  30

Pro Arg Ser Asp Gly Ala Lys Pro Gly Pro Arg Glu Gly Lys Arg Ser
            35                  40                  45

Tyr Ser Met Glu His Phe Arg Trp Gly Lys Pro Val
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: Synthetic: ACTH1-24 natural C-terminal spacer
      Alpha-MSH

<400> SEQUENCE: 43

Ser Tyr Ser Met Glu His Phe Arg Trp Gly Lys Pro Val Gly Lys Lys
1               5                   10                  15

Arg Arg Pro Val Lys Val Tyr Pro Glu Leu Thr Gly Gln Arg Leu Arg
            20                  25                  30

Glu Gly Asp Gly Pro Asp Gly Pro Ala Asp Asp Gly Ala Gly Ala Ser
            35                  40                  45

Tyr Ser Met Glu His Phe Arg Trp Gly Lys Pro Val
    50                  55                  60

<210> SEQ ID NO 44
<211> LENGTH: 15
<212> TYPE: PRT
<213> ORGANISM: Artificial Sequence
<220> FEATURE:
<223> OTHER INFORMATION: Synthetic: NDP-ACTH4-9 Beta-Ala-G Ala
      NDP-ACTH4-9
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala
<220> FEATURE:
<221> NAME/KEY: misc_feature
<222> LOCATION: (10)..(10)
<223> OTHER INFORMATION: Xaa is Nle (norleucine)
<220> FEATURE:
<221> NAME/KEY: misc_feature
<222> LOCATION: (13)..(13)
<223> OTHER INFORMATION: Xaa is DPhe (D-phenylalanine)

<400> SEQUENCE: 44

Xaa Glu His Xaa Arg Trp Ala Gly Ala Xaa Glu His Xaa Arg Trp
1               5                   10                  15

<210> SEQ ID NO 45
<211> LENGTH: 33
<212> TYPE: PRT

<213> ORGANISM: Artificial Sequence
<220> FEATURE:
<223> OTHER INFORMATION: Synthetic: NDP-ACTH4-9 Beta-Ala-G Ala ACTH1-24
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala

<400> SEQUENCE: 45

Xaa Glu His Xaa Arg Trp Ala Gly Ala Ser Tyr Ser Met Glu His Phe
1               5                   10                  15

Arg Trp Gly Lys Pro Val Gly Lys Lys Arg Arg Pro Val Lys Val Tyr
            20                  25                  30

Pro

<210> SEQ ID NO 46
<211> LENGTH: 30
<212> TYPE: PRT
<213> ORGANISM: Artificial Sequence
<220> FEATURE:
<223> OTHER INFORMATION: Synthetic: NDP-ACTH4-9  ACTH1-24
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)

<400> SEQUENCE: 46

Xaa Glu His Xaa Arg Trp Ser Tyr Ser Met Glu His Phe Arg Trp Gly
1               5                   10                  15

Lys Pro Val Gly Lys Lys Arg Arg Pro Val Lys Val Tyr Pro
            20                  25                  30

<210> SEQ ID NO 47
<211> LENGTH: 24
<212> TYPE: PRT
<213> ORGANISM: Artificial Sequence
<220> FEATURE:
<223> OTHER INFORMATION: Synthetic: NDP-ACTH
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 47

Ser Tyr Ser Xaa Glu His Xaa Arg Trp Gly Lys Pro Val Gly Lys Lys
1               5                   10                  15

Arg Arg Pro Val Lys Val Tyr Pro
            20

<210> SEQ ID NO 48
<211> LENGTH: 24
<212> TYPE: PRT
<213> ORGANISM: Artificial Sequence
<220> FEATURE:
<223> OTHER INFORMATION: Synthetic: ACTH1-24-point-5

<400> SEQUENCE: 48

Ser Tyr Ser Met Glu His Phe Arg Trp Gly Lys Pro Val Gly Lys Lys
1               5                   10                  15

Arg Arg Ala Val Lys Val Tyr Pro
            20

<210> SEQ ID NO 49
<211> LENGTH: 24
<212> TYPE: PRT
<213> ORGANISM: Artificial Sequence
<220> FEATURE:
<223> OTHER INFORMATION: Synthetic: ACTH1-24-point-1-2

<400> SEQUENCE: 49

Ser Tyr Ser Met Glu His Phe Arg Trp Gly Lys Pro Val Gly Ala Ala
1               5                   10                  15

Arg Arg Pro Val Lys Val Tyr Pro
            20

<210> SEQ ID NO 50
<211> LENGTH: 24
<212> TYPE: PRT
<213> ORGANISM: Artificial Sequence
<220> FEATURE:
<223> OTHER INFORMATION: Synthetic: ACTH1-24-point-3-5

<400> SEQUENCE: 50

Ser Tyr Ser Met Glu His Phe Arg Trp Gly Lys Pro Val Gly Lys Lys
1               5                   10                  15

Ala Ala Ala Val Lys Val Tyr Pro
            20

<210> SEQ ID NO 51
<211> LENGTH: 37
<212> TYPE: PRT
<213> ORGANISM: Artificial Sequence
<220> FEATURE:
<223> OTHER INFORMATION: Synthetic: ACTH1-24 NDP-Alpha-MSH
<220> FEATURE:
<221> NAME/KEY: misc_feature
<222> LOCATION: (28)..(28)
<223> OTHER INFORMATION: Xaa is Nle (norleucine)
<220> FEATURE:
<221> NAME/KEY: misc_feature
<222> LOCATION: (31)..(31)
<223> OTHER INFORMATION: Xaa is DPhe (D-phenylalanine)

<400> SEQUENCE: 51

Ser Tyr Ser Met Glu His Phe Arg Trp Gly Lys Pro Val Gly Lys Lys
1               5                   10                  15

Arg Arg Pro Val Lys Val Tyr Pro Ser Tyr Ser Xaa Glu His Xaa Arg
            20                  25                  30

Trp Gly Lys Pro Val
        35

<210> SEQ ID NO 52
<211> LENGTH: 37
<212> TYPE: PRT

<213> ORGANISM: Artificial Sequence
<220> FEATURE:
<223> OTHER INFORMATION: Synthetic: ACTH1-24-point-5  NDP-Alpha-MSH
<220> FEATURE:
<221> NAME/KEY: misc_feature
<222> LOCATION: (28)..(28)
<223> OTHER INFORMATION: Xaa is Nle (norleucine)
<220> FEATURE:
<221> NAME/KEY: misc_feature
<222> LOCATION: (31)..(31)
<223> OTHER INFORMATION: Xaa is DPhe (D-phenylalanine)

<400> SEQUENCE: 52

Ser Tyr Ser Met Glu His Phe Arg Trp Gly Lys Pro Val Gly Lys Lys
1               5                   10                  15

Arg Arg Ala Val Lys Val Tyr Pro Ser Tyr Ser Xaa Glu His Xaa Arg
            20                  25                  30

Trp Gly Lys Pro Val
        35

<210> SEQ ID NO 53
<211> LENGTH: 37
<212> TYPE: PRT
<213> ORGANISM: Artificial Sequence
<220> FEATURE:
<223> OTHER INFORMATION: Synthetic: ACTH1-24-point-1-2  NDP-Alpha-MSH
<220> FEATURE:
<221> NAME/KEY: misc_feature
<222> LOCATION: (28)..(28)
<223> OTHER INFORMATION: Xaa is Nle (norleucine)
<220> FEATURE:
<221> NAME/KEY: misc_feature
<222> LOCATION: (31)..(31)
<223> OTHER INFORMATION: Xaa is DPhe (D-phenylalanine)

<400> SEQUENCE: 53

Ser Tyr Ser Met Glu His Phe Arg Trp Gly Lys Pro Val Gly Ala Ala
1               5                   10                  15

Arg Arg Pro Val Lys Val Tyr Pro Ser Tyr Ser Xaa Glu His Xaa Arg
            20                  25                  30

Trp Gly Lys Pro Val
        35

<210> SEQ ID NO 54
<211> LENGTH: 37
<212> TYPE: PRT
<213> ORGANISM: Artificial Sequence
<220> FEATURE:
<223> OTHER INFORMATION: Synthetic: ACTH1-24-point-3-5  NDP-Alpha-MSH
<220> FEATURE:
<221> NAME/KEY: misc_feature
<222> LOCATION: (28)..(28)
<223> OTHER INFORMATION: Xaa is Nle (norleucine)
<220> FEATURE:
<221> NAME/KEY: misc_feature
<222> LOCATION: (31)..(31)
<223> OTHER INFORMATION: Xaa is DPhe (D-phenylalanine)

<400> SEQUENCE: 54

Ser Tyr Ser Met Glu His Phe Arg Trp Gly Lys Pro Val Gly Lys Lys
1               5                   10                  15

Ala Ala Ala Val Lys Val Tyr Pro Ser Tyr Ser Xaa Glu His Xaa Arg
            20                  25                  30

Trp Gly Lys Pro Val
        35

<210> SEQ ID NO 55

```
<211> LENGTH: 41
<212> TYPE: PRT
<213> ORGANISM: Artificial Sequence
<220> FEATURE:
<223> OTHER INFORMATION: Synthetic: ACTH1-24  4aa  NDP-Alpha-MSH
<220> FEATURE:
<221> NAME/KEY: misc_feature
<222> LOCATION: (32)..(32)
<223> OTHER INFORMATION: Xaa is Nle (norleucine)
<220> FEATURE:
<221> NAME/KEY: misc_feature
<222> LOCATION: (35)..(35)
<223> OTHER INFORMATION: Xaa is DPhe (D-phenylalanine)

<400> SEQUENCE: 55

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Ser Tyr Ser Xaa
            20                  25                  30

Glu His Xaa Arg Trp Gly Lys Pro Val
        35                  40

<210> SEQ ID NO 56
<211> LENGTH: 41
<212> TYPE: PRT
<213> ORGANISM: Artificial Sequence
<220> FEATURE:
<223> OTHER INFORMATION: Synthetic: ACTH1-24-point-5  4aa  NDP-Alpha-MSH
<220> FEATURE:
<221> NAME/KEY: misc_feature
<222> LOCATION: (32)..(32)
<223> OTHER INFORMATION: Xaa is Nle (norleucine)
<220> FEATURE:
<221> NAME/KEY: misc_feature
<222> LOCATION: (35)..(35)
<223> OTHER INFORMATION: Xaa is DPhe (D-phenylalanine)

<400> SEQUENCE: 56

Ser Tyr Ser Met Glu His Phe Arg Trp Gly Lys Pro Val Gly Lys Lys
1               5                   10                  15

Arg Arg Ala Val Lys Val Tyr Pro Gly Gly Gly Ser Ser Tyr Ser Xaa
            20                  25                  30

Glu His Xaa Arg Trp Gly Lys Pro Val
        35                  40

<210> SEQ ID NO 57
<211> LENGTH: 41
<212> TYPE: PRT
<213> ORGANISM: Artificial Sequence
<220> FEATURE:
<223> OTHER INFORMATION: Synthetic: ACTH1-24-point-1-2  4aa
    NDP-Alpha-MSH
<220> FEATURE:
<221> NAME/KEY: misc_feature
<222> LOCATION: (32)..(32)
<223> OTHER INFORMATION: Xaa is Nle (norleucine)
<220> FEATURE:
<221> NAME/KEY: misc_feature
<222> LOCATION: (35)..(35)
<223> OTHER INFORMATION: Xaa is DPhe (D-phenylalanine)

<400> SEQUENCE: 57

Ser Tyr Ser Met Glu His Phe Arg Trp Gly Lys Pro Val Gly Ala Ala
1               5                   10                  15

Arg Arg Pro Val Lys Val Tyr Pro Gly Gly Gly Ser Ser Tyr Ser Xaa
            20                  25                  30

Glu His Xaa Arg Trp Gly Lys Pro Val
        35                  40
```

<210> SEQ ID NO 58
<211> LENGTH: 41
<212> TYPE: PRT
<213> ORGANISM: Artificial Sequence
<220> FEATURE:
<223> OTHER INFORMATION: Synthetic: ACTH1-24-point-3-5  4aa
      NDP-Alpha-MSH
<220> FEATURE:
<221> NAME/KEY: misc_feature
<222> LOCATION: (32)..(32)
<223> OTHER INFORMATION: Xaa is Nle (norleucine)
<220> FEATURE:
<221> NAME/KEY: misc_feature
<222> LOCATION: (35)..(35)
<223> OTHER INFORMATION: Xaa is DPhe (D-phenylalanine)

<400> SEQUENCE: 58

Ser Tyr Ser Met Glu His Phe Arg Trp Gly Lys Pro Val Gly Lys Lys
1               5                   10                  15

Ala Ala Ala Val Lys Val Tyr Pro Gly Gly Gly Ser Ser Tyr Ser Xaa
            20                  25                  30

Glu His Xaa Arg Trp Gly Lys Pro Val
            35                  40

<210> SEQ ID NO 59
<211> LENGTH: 44
<212> TYPE: PRT
<213> ORGANISM: Artificial Sequence
<220> FEATURE:
<223> OTHER INFORMATION: Synthetic: ACTH1-24  7aa  NDP-Alpha-MSH
<220> FEATURE:
<221> NAME/KEY: misc_feature
<222> LOCATION: (35)..(35)
<223> OTHER INFORMATION: Xaa is Nle (norleucine)
<220> FEATURE:
<221> NAME/KEY: misc_feature
<222> LOCATION: (38)..(38)
<223> OTHER INFORMATION: Xaa is DPhe (D-phenylalanine)

<400> SEQUENCE: 59

Ser Tyr Ser Met Glu His Phe Arg Trp Gly Lys Pro Val Gly Lys Lys
1               5                   10                  15

Arg Arg Pro Val Lys Val Tyr Pro Gly Gly Gly Ser Gly Gly Ser
            20                  25                  30

Tyr Ser Xaa Glu His Xaa Arg Trp Gly Lys Pro Val
            35                  40

<210> SEQ ID NO 60
<211> LENGTH: 44
<212> TYPE: PRT
<213> ORGANISM: Artificial Sequence
<220> FEATURE:
<223> OTHER INFORMATION: Synthetic: ACTH1-24-point-5  7aa  NDP-Alpha-MSH
<220> FEATURE:
<221> NAME/KEY: misc_feature
<222> LOCATION: (35)..(35)
<223> OTHER INFORMATION: Xaa is Nle (norleucine)
<220> FEATURE:
<221> NAME/KEY: misc_feature
<222> LOCATION: (38)..(38)
<223> OTHER INFORMATION: Xaa is DPhe (D-phenylalanine)

<400> SEQUENCE: 60

Ser Tyr Ser Met Glu His Phe Arg Trp Gly Lys Pro Val Gly Lys Lys
1               5                   10                  15

Arg Arg Ala Val Lys Val Tyr Pro Gly Gly Gly Ser Gly Gly Ser
            20                  25                  30

Tyr Ser Xaa Glu His Xaa Arg Trp Gly Lys Pro Val
            35                  40

<210> SEQ ID NO 61
<211> LENGTH: 44
<212> TYPE: PRT
<213> ORGANISM: Artificial Sequence
<220> FEATURE:
<223> OTHER INFORMATION: Synthetic: ACTH1-24-point-1-2  7aa
      NDP-Alpha-MSH
<220> FEATURE:
<221> NAME/KEY: misc_feature
<222> LOCATION: (35)..(35)
<223> OTHER INFORMATION: Xaa is Nle (norleucine)
<220> FEATURE:
<221> NAME/KEY: misc_feature
<222> LOCATION: (38)..(38)
<223> OTHER INFORMATION: Xaa is DPhe (D-phenylalanine)

<400> SEQUENCE: 61

Ser Tyr Ser Met Glu His Phe Arg Trp Gly Lys Pro Val Gly Ala Ala
1               5                   10                  15

Arg Arg Pro Val Lys Val Tyr Pro Gly Gly Gly Gly Ser Gly Gly Ser
            20                  25                  30

Tyr Ser Xaa Glu His Xaa Arg Trp Gly Lys Pro Val
            35                  40

<210> SEQ ID NO 62
<211> LENGTH: 44
<212> TYPE: PRT
<213> ORGANISM: Artificial Sequence
<220> FEATURE:
<223> OTHER INFORMATION: Synthetic: ACTH1-24-point-3-5  7aa
      NDP-Alpha-MSH
<220> FEATURE:
<221> NAME/KEY: misc_feature
<222> LOCATION: (35)..(35)
<223> OTHER INFORMATION: Xaa is Nle (norleucine)
<220> FEATURE:
<221> NAME/KEY: misc_feature
<222> LOCATION: (38)..(38)
<223> OTHER INFORMATION: Xaa is DPhe (D-phenylalanine)

<400> SEQUENCE: 62

Ser Tyr Ser Met Glu His Phe Arg Trp Gly Lys Pro Val Gly Lys Lys
1               5                   10                  15

Ala Ala Ala Val Lys Val Tyr Pro Gly Gly Gly Gly Ser Gly Gly Ser
            20                  25                  30

Tyr Ser Xaa Glu His Xaa Arg Trp Gly Lys Pro Val
            35                  40

<210> SEQ ID NO 63
<211> LENGTH: 47
<212> TYPE: PRT
<213> ORGANISM: Artificial Sequence
<220> FEATURE:
<223> OTHER INFORMATION: Synthetic: ACTH1-24-point-5  10aa
      NDP-Alpha-MSH
<220> FEATURE:
<221> NAME/KEY: misc_feature
<222> LOCATION: (38)..(38)
<223> OTHER INFORMATION: Xaa is Nle (norleucine)
<220> FEATURE:
<221> NAME/KEY: misc_feature
<222> LOCATION: (41)..(41)
<223> OTHER INFORMATION: Xaa is DPhe (D-phenylalanine)

<400> SEQUENCE: 63

```
Ser Tyr Ser Met Glu His Phe Arg Trp Gly Lys Pro Val Gly Lys Lys
1               5                   10                  15

Arg Arg Ala Val Lys Val Tyr Pro Gly Gly Gly Ser Gly Gly Gly
            20                  25                  30

Gly Ser Ser Tyr Ser Xaa Glu His Xaa Arg Trp Gly Lys Pro Val
        35                  40                  45

<210> SEQ ID NO 64
<211> LENGTH: 47
<212> TYPE: PRT
<213> ORGANISM: Artificial Sequence
<220> FEATURE:
<223> OTHER INFORMATION: Synthetic: ACTH1-24-point-1-2  10aa
      NDP-Alpha-MSH
<220> FEATURE:
<221> NAME/KEY: misc_feature
<222> LOCATION: (38)..(38)
<223> OTHER INFORMATION: Xaa is Nle (norleucine)
<220> FEATURE:
<221> NAME/KEY: misc_feature
<222> LOCATION: (41)..(41)
<223> OTHER INFORMATION: Xaa is DPhe (D-phenylalanine)

<400> SEQUENCE: 64

Ser Tyr Ser Met Glu His Phe Arg Trp Gly Lys Pro Val Gly Ala Ala
1               5                   10                  15

Arg Arg Pro Val Lys Val Tyr Pro Gly Gly Gly Ser Gly Gly Gly
            20                  25                  30

Gly Ser Ser Tyr Ser Xaa Glu His Xaa Arg Trp Gly Lys Pro Val
        35                  40                  45

<210> SEQ ID NO 65
<211> LENGTH: 47
<212> TYPE: PRT
<213> ORGANISM: Artificial Sequence
<220> FEATURE:
<223> OTHER INFORMATION: Synthetic: ACTH1-24-point-3-5  10aa
      NDP-Alpha-MSH
<220> FEATURE:
<221> NAME/KEY: misc_feature
<222> LOCATION: (38)..(38)
<223> OTHER INFORMATION: Xaa is Nle (norleucine)
<220> FEATURE:
<221> NAME/KEY: misc_feature
<222> LOCATION: (41)..(41)
<223> OTHER INFORMATION: Xaa is DPhe (D-phenylalanine)

<400> SEQUENCE: 65

Ser Tyr Ser Met Glu His Phe Arg Trp Gly Lys Pro Val Gly Lys Lys
1               5                   10                  15

Ala Ala Ala Val Lys Val Tyr Pro Gly Gly Gly Ser Gly Gly Gly
            20                  25                  30

Gly Ser Ser Tyr Ser Xaa Glu His Xaa Arg Trp Gly Lys Pro Val
        35                  40                  45

<210> SEQ ID NO 66
<211> LENGTH: 42
<212> TYPE: PRT
<213> ORGANISM: Artificial Sequence
<220> FEATURE:
<223> OTHER INFORMATION: Synthetic: NDP-ACTH4-9   Beta-Ala-G Ala
      ACTH1-24 Beta-Ala-G Ala   NDP-ACTH4-9
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
```

```
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala
<220> FEATURE:
<221> NAME/KEY: misc_feature
<222> LOCATION: (34)..(34)
<223> OTHER INFORMATION: Ala is Beta Ala
<220> FEATURE:
<221> NAME/KEY: misc_feature
<222> LOCATION: (36)..(36)
<223> OTHER INFORMATION: Ala is Beta Ala
<220> FEATURE:
<221> NAME/KEY: misc_feature
<222> LOCATION: (37)..(37)
<223> OTHER INFORMATION: Xaa is Nle (norleucine)
<220> FEATURE:
<221> NAME/KEY: misc_feature
<222> LOCATION: (40)..(40)
<223> OTHER INFORMATION: Xaa is DPhe (D-phenylalanine)

<400> SEQUENCE: 66

Xaa Glu His Xaa Arg Trp Ala Gly Ala Ser Tyr Ser Met Glu His Phe
1               5                   10                  15

Arg Trp Gly Lys Pro Val Gly Lys Lys Arg Arg Pro Val Lys Val Tyr
            20                  25                  30

Pro Ala Gly Ala Xaa Glu His Xaa Arg Trp
        35                  40

<210> SEQ ID NO 67
<211> LENGTH: 60
<212> TYPE: PRT
<213> ORGANISM: Artificial Sequence
<220> FEATURE:
<223> OTHER INFORMATION: Synthetic: NDP-ACTH4-9  Beta-Ala-G Ala
      NDP-ACTH4-9  Beta-Ala-G Ala   ACTH1-24  Beta-Ala-G Ala
      NDP-ACTH4-9    Beta-Ala-G Ala NDP-ACTH4-9
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala
<220> FEATURE:
<221> NAME/KEY: misc_feature
<222> LOCATION: (10)..(10)
<223> OTHER INFORMATION: Xaa is Nle (norleucine)
<220> FEATURE:
<221> NAME/KEY: misc_feature
<222> LOCATION: (13)..(13)
<223> OTHER INFORMATION: Xaa is DPhe (D-phenylalanine)
<220> FEATURE:
<221> NAME/KEY: misc_feature
<222> LOCATION: (16)..(16)
<223> OTHER INFORMATION: Ala is Beta Ala
<220> FEATURE:
<221> NAME/KEY: misc_feature
<222> LOCATION: (18)..(18)
<223> OTHER INFORMATION: Ala is Beta Ala
```

-continued

```
<220> FEATURE:
<221> NAME/KEY: misc_feature
<222> LOCATION: (43)..(43)
<223> OTHER INFORMATION: Ala is Beta Ala
<220> FEATURE:
<221> NAME/KEY: misc_feature
<222> LOCATION: (45)..(45)
<223> OTHER INFORMATION: Ala is Beta Ala
<220> FEATURE:
<221> NAME/KEY: misc_feature
<222> LOCATION: (46)..(46)
<223> OTHER INFORMATION: Xaa is Nle (norleucine)
<220> FEATURE:
<221> NAME/KEY: misc_feature
<222> LOCATION: (49)..(49)
<223> OTHER INFORMATION: Xaa is DPhe (D-phenylalanine)
<220> FEATURE:
<221> NAME/KEY: misc_feature
<222> LOCATION: (52)..(52)
<223> OTHER INFORMATION: Ala is Beta Ala
<220> FEATURE:
<221> NAME/KEY: misc_feature
<222> LOCATION: (54)..(54)
<223> OTHER INFORMATION: Ala is Beta Ala
<220> FEATURE:
<221> NAME/KEY: misc_feature
<222> LOCATION: (55)..(55)
<223> OTHER INFORMATION: Xaa is Nle (norleucine)
<220> FEATURE:
<221> NAME/KEY: misc_feature
<222> LOCATION: (58)..(58)
<223> OTHER INFORMATION: Xaa is DPhe (D-phenylalanine)

<400> SEQUENCE: 67

Xaa Glu His Xaa Arg Trp Ala Gly Ala Xaa Glu His Xaa Arg Trp Ala
1               5                   10                  15

Gly Ala Ser Tyr Ser Met Glu His Phe Arg Trp Gly Lys Pro Val Gly
            20                  25                  30

Lys Lys Arg Arg Pro Val Lys Val Tyr Pro Ala Gly Ala Xaa Glu His
        35                  40                  45

Xaa Arg Trp Ala Gly Ala Xaa Glu His Xaa Arg Trp
    50                  55                  60

<210> SEQ ID NO 68
<211> LENGTH: 51
<212> TYPE: PRT
<213> ORGANISM: Artificial Sequence
<220> FEATURE:
<223> OTHER INFORMATION: Synthetic: NDP-ACTH4-9 Beta-Ala-G Ala
      ACTH1-24 Beta-Ala-G Ala NDP-ACTH4-9 Beta-Ala-G Ala  NDP-ACTH4-9
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala
<220> FEATURE:
<221> NAME/KEY: misc_feature
<222> LOCATION: (34)..(34)
<223> OTHER INFORMATION: Ala is Beta Ala
<220> FEATURE:
<221> NAME/KEY: misc_feature
<222> LOCATION: (36)..(36)
<223> OTHER INFORMATION: Ala is Beta Ala
```

```
<220> FEATURE:
<221> NAME/KEY: misc_feature
<222> LOCATION: (37)..(37)
<223> OTHER INFORMATION: Xaa is Nle (norleucine)
<220> FEATURE:
<221> NAME/KEY: misc_feature
<222> LOCATION: (40)..(40)
<223> OTHER INFORMATION: Xaa is DPhe (D-phenylalanine)
<220> FEATURE:
<221> NAME/KEY: misc_feature
<222> LOCATION: (43)..(43)
<223> OTHER INFORMATION: Ala is Beta Ala
<220> FEATURE:
<221> NAME/KEY: misc_feature
<222> LOCATION: (45)..(45)
<223> OTHER INFORMATION: Ala is Beta Ala
<220> FEATURE:
<221> NAME/KEY: misc_feature
<222> LOCATION: (46)..(46)
<223> OTHER INFORMATION: Xaa is Nle (norleucine)
<220> FEATURE:
<221> NAME/KEY: misc_feature
<222> LOCATION: (49)..(49)
<223> OTHER INFORMATION: Xaa is DPhe (D-phenylalanine)

<400> SEQUENCE: 68

Xaa Glu His Xaa Arg Trp Ala Gly Ala Ser Tyr Ser Met Glu His Phe
 1               5                  10                  15

Arg Trp Gly Lys Pro Val Gly Lys Lys Arg Arg Pro Val Lys Val Tyr
            20                  25                  30

Pro Ala Gly Ala Xaa Glu His Xaa Arg Trp Ala Gly Ala Xaa Glu His
         35                  40                  45

Xaa Arg Trp
    50

<210> SEQ ID NO 69
<211> LENGTH: 51
<212> TYPE: PRT
<213> ORGANISM: Artificial Sequence
<220> FEATURE:
<223> OTHER INFORMATION: Synthetic: NDP-ACTH4-9  Beta-Ala-G Ala
      NDP-ACTH4-9  Beta-Ala-G Ala   ACTH1-24  Beta-Ala-G Ala
      NDP-ACTH4-9
<220> FEATURE:
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala
<220> FEATURE:
<221> NAME/KEY: misc_feature
<222> LOCATION: (10)..(10)
<223> OTHER INFORMATION: Xaa is Nle (norleucine)
<220> FEATURE:
<221> NAME/KEY: misc_feature
<222> LOCATION: (13)..(13)
<223> OTHER INFORMATION: Xaa is DPhe (D-phenylalanine)
<220> FEATURE:
<221> NAME/KEY: misc_feature
<222> LOCATION: (16)..(16)
<223> OTHER INFORMATION: Ala is Beta Ala
<220> FEATURE:
<221> NAME/KEY: misc_feature
<222> LOCATION: (18)..(18)
```

```
<223> OTHER INFORMATION: Ala is Beta Ala
<220> FEATURE:
<221> NAME/KEY: misc_feature
<222> LOCATION: (43)..(43)
<223> OTHER INFORMATION: Ala is Beta Ala
<220> FEATURE:
<221> NAME/KEY: misc_feature
<222> LOCATION: (45)..(45)
<223> OTHER INFORMATION: Ala is Beta Ala
<220> FEATURE:
<221> NAME/KEY: misc_feature
<222> LOCATION: (46)..(46)
<223> OTHER INFORMATION: Xaa is Nle (norleucine)
<220> FEATURE:
<221> NAME/KEY: misc_feature
<222> LOCATION: (49)..(49)
<223> OTHER INFORMATION: Xaa is DPhe (D-phenylalanine)

<400> SEQUENCE: 69

Xaa Glu His Xaa Arg Trp Ala Gly Ala Xaa Glu His Xaa Arg Trp Ala
1               5                   10                  15

Gly Ala Ser Tyr Ser Met Glu His Phe Arg Trp Gly Lys Pro Val Gly
            20                  25                  30

Lys Lys Arg Arg Pro Val Lys Val Tyr Pro Ala Gly Ala Xaa Glu His
        35                  40                  45

Xaa Arg Trp
    50

<210> SEQ ID NO 70
<211> LENGTH: 33
<212> TYPE: PRT
<213> ORGANISM: Artificial Sequence
<220> FEATURE:
<223> OTHER INFORMATION: Synthetic: ACTH1-24  Beta-Ala-G Ala
      NDP-ACTH4-9
<220> FEATURE:
<221> NAME/KEY: misc_feature
<222> LOCATION: (25)..(25)
<223> OTHER INFORMATION: Ala is Beta Ala
<220> FEATURE:
<221> NAME/KEY: misc_feature
<222> LOCATION: (27)..(27)
<223> OTHER INFORMATION: Ala is Beta Ala
<220> FEATURE:
<221> NAME/KEY: misc_feature
<222> LOCATION: (28)..(28)
<223> OTHER INFORMATION: Xaa is Nle (norleucine)
<220> FEATURE:
<221> NAME/KEY: misc_feature
<222> LOCATION: (31)..(31)
<223> OTHER INFORMATION: Xaa is DPhe (D-phenylalanine)

<400> SEQUENCE: 70

Ser Tyr Ser Met Glu His Phe Arg Trp Gly Lys Pro Val Gly Lys Lys
1               5                   10                  15

Arg Arg Pro Val Lys Val Tyr Pro Ala Gly Ala Xaa Glu His Xaa Arg
            20                  25                  30

Trp

<210> SEQ ID NO 71
<211> LENGTH: 33
<212> TYPE: PRT
<213> ORGANISM: Artificial Sequence
<220> FEATURE:
<223> OTHER INFORMATION: Synthetic: NDP-ACTH4-9  Beta-Ala-G Ala
      ACTH1-24
<220> FEATURE:
<221> NAME/KEY: misc_feature
<223> OTHER INFORMATION: Acetylation on 5' end
<220> FEATURE:
```

```
<221> NAME/KEY: misc_feature
<222> LOCATION: (1)..(1)
<223> OTHER INFORMATION: Xaa is Nle (norleucine)
<220> FEATURE:
<221> NAME/KEY: misc_feature
<222> LOCATION: (4)..(4)
<223> OTHER INFORMATION: Xaa is DPhe (D-phenylalanine)
<220> FEATURE:
<221> NAME/KEY: misc_feature
<222> LOCATION: (7)..(7)
<223> OTHER INFORMATION: Ala is Beta Ala
<220> FEATURE:
<221> NAME/KEY: misc_feature
<222> LOCATION: (9)..(9)
<223> OTHER INFORMATION: Ala is Beta Ala

<400> SEQUENCE: 71

Xaa Glu His Xaa Arg Trp Ala Gly Ala Ser Tyr Ser Met Glu His Phe
1               5                   10                  15

Arg Trp Gly Lys Pro Val Gly Lys Lys Arg Arg Pro Val Lys Val Tyr
            20                  25                  30

Pro

<210> SEQ ID NO 72
<211> LENGTH: 13
<212> TYPE: PRT
<213> ORGANISM: Artificial Sequence
<220> FEATURE:
<223> OTHER INFORMATION: Synthetic: NDP-Alpha-MSH
<220> FEATURE:
<221> NAME/KEY: misc_feature
<223> OTHER INFORMATION: Acetylation on 5' end
<220> FEATURE:
<221> NAME/KEY: misc_feature
<222> LOCATION: (4)..(4)
<223> OTHER INFORMATION: Xaa is Nle (norleucine)
<220> FEATURE:
<221> NAME/KEY: misc_feature
<222> LOCATION: (7)..(7)
<223> OTHER INFORMATION: Xaa is DPhe (D-phenylalanine)

<400> SEQUENCE: 72

Ser Tyr Ser Xaa Glu His Xaa Arg Trp Gly Lys Pro Val
1               5                   10

<210> SEQ ID NO 73
<211> LENGTH: 4
<212> TYPE: PRT
<213> ORGANISM: Artificial Sequence
<220> FEATURE:
<223> OTHER INFORMATION: Synthetic linker

<400> SEQUENCE: 73

Arg Arg Lys Arg
1

<210> SEQ ID NO 74
<211> LENGTH: 4
<212> TYPE: PRT
<213> ORGANISM: Artificial Sequence
<220> FEATURE:
<223> OTHER INFORMATION: Synthetic linker

<400> SEQUENCE: 74

Lys Lys Arg Arg
1

<210> SEQ ID NO 75
<211> LENGTH: 16
```

```
<212> TYPE: PRT
<213> ORGANISM: Artificial Sequence
<220> FEATURE:
<223> OTHER INFORMATION: Synthetic linker

<400> SEQUENCE: 75

Arg Arg Asn Ser Ser Ser Ser Gly Ser Ser Gly Ala Gly Gln Lys Arg
1               5                   10                  15

<210> SEQ ID NO 76
<211> LENGTH: 9
<212> TYPE: PRT
<213> ORGANISM: Artificial Sequence
<220> FEATURE:
<223> OTHER INFORMATION: Synthetic linker

<400> SEQUENCE: 76

Glu Arg Leu Lys Arg Ala Val Gly Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic linker

<400> SEQUENCE: 77

Ser Arg Ser Arg Arg Ser Ala Gly Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic linker

<400> SEQUENCE: 78

Glu Arg Ser Lys Arg Ala Val Gly Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic linker

<400> SEQUENCE: 79

Glu Arg Leu Lys Arg Ala Ala Gly Ser
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic linker

<400> SEQUENCE: 80

Gly Gly Gly Gly Ser Gly Gly Gly Gly Ser
1               5                   10

<210> SEQ ID NO 81
<211> LENGTH: 6
<212> TYPE: PRT
```

```
<213> ORGANISM: Artificial Sequence
<220> FEATURE:
<223> OTHER INFORMATION: Synthetic linker

<400> SEQUENCE: 81

Pro Leu Gly Leu Trp Ala
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic linker

<400> SEQUENCE: 82

Pro Gln Ala Leu Val Ala
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic linker

<400> SEQUENCE: 83

Pro Ala Asn Leu Val Gly
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic linker

<400> SEQUENCE: 84

Pro Ala Glu Leu Ile Gly
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic linker

<400> SEQUENCE: 85

Pro Ala Asn Leu Val Ala
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic linker

<400> SEQUENCE: 86

Pro Ala Gly Leu Val Gly
1               5

<210> SEQ ID NO 87
<211> LENGTH: 6
<212> TYPE: PRT
<213> ORGANISM: Artificial Sequence
```

```
<220> FEATURE:
<223> OTHER INFORMATION: Synthetic linker

<400> SEQUENCE: 87

Pro Ala Gly Leu Val Ala
1               5

<210> SEQ ID NO 88
<211> LENGTH: 11
<212> TYPE: PRT
<213> ORGANISM: Artificial Sequence
<220> FEATURE:
<223> OTHER INFORMATION: Synthetic: Gamma2-MSH

<400> SEQUENCE: 88

Tyr Val Met Gly His Phe Arg Trp Asp Arg Phe
1               5                   10

<210> SEQ ID NO 89
<211> LENGTH: 4
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (1)..(4)
<223> OTHER INFORMATION: "GGGS" may repeat any number of times

<400> SEQUENCE: 89

Gly Gly Gly Ser
1

<210> SEQ ID NO 90
<211> LENGTH: 5
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (1)..(5)
<223> OTHER INFORMATION: "GGGGS" may repeat any number of times

<400> SEQUENCE: 90

Gly Gly Gly Gly Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic linker

<400> SEQUENCE: 91

Glu Ala Ala Ala Lys
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic linker

<400> SEQUENCE: 92

Gly Gly Gly Ser
```

```
<210> SEQ ID NO 93
<211> LENGTH: 7
<212> TYPE: PRT
<213> ORGANISM: Artificial Sequence
<220> FEATURE:
<223> OTHER INFORMATION: Synthetic linker

<400> SEQUENCE: 93

Gly Gly Gly Gly Ser Gly Gly
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic linker

<400> SEQUENCE: 94

Gly Gly Ser Gly Gly Ser Gly Gly Ser
1               5
```